(12) United States Patent
Pei et al.

(10) Patent No.: US 8,828,990 B2
(45) Date of Patent: Sep. 9, 2014

(54) N-7 SUBSTITUTED PURINE AND PYRAZOLOPYRIMINE COMPOUNDS, COMPOSITIONS AND METHODS OF USE

(75) Inventors: Zhonghua Pei, Burlingame, CA (US); Joseph P. Lyssikatos, Piedmont, CA (US); Wendy Lee, San Ramon, CA (US); Kirk D. Robarge, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 437 days.

(21) Appl. No.: 12/943,225

(22) Filed: Nov. 10, 2010

(65) Prior Publication Data

US 2011/0086840 A1    Apr. 14, 2011

Related U.S. Application Data

(60) Provisional application No. 61/260,628, filed on Nov. 12, 2009.

(51) Int. Cl.

| | |
|---|---|
| *C07D 473/04* | (2006.01) |
| *A61K 31/52* | (2006.01) |
| *C07D 473/34* | (2006.01) |
| *C07D 519/00* | (2006.01) |
| *C07D 487/04* | (2006.01) |
| *A61K 31/519* | (2006.01) |

(52) U.S. Cl.
CPC ............ *C07D 473/34* (2013.01); *C07D 519/00* (2013.01); *C07D 487/04* (2013.01)
USPC ................ 514/211.15; 514/234.2; 514/230.5; 544/118; 544/105; 540/544

(58) Field of Classification Search
CPC .. C07D 471/04; C07D 473/32; A61K 31/519; A61K 31/52
USPC .................... 544/122, 118; 514/263.1, 234.2, 514/211.15; 540/544
See application file for complete search history.

(56) References Cited

U.S. PATENT DOCUMENTS

| | | | |
|---|---|---|---|
| 3,248,395 A | 4/1966 | Ohnacker et al. | |
| 5,338,740 A | 8/1994 | Carpino et al. | |
| 5,942,508 A | 8/1999 | Sawa | |
| 6,583,154 B1 | 6/2003 | Norman et al. | |
| 6,608,053 B2 | 8/2003 | Hayakawa et al. | |
| 6,608,056 B1 | 8/2003 | Hayakawa et al. | |
| 6,770,641 B2 | 8/2004 | Hayakawa et al. | |
| 6,800,633 B2 | 10/2004 | Castelhano et al. | |
| 6,838,457 B2 | 1/2005 | Hayakawa et al. | |
| 6,838,559 B2 | 1/2005 | Vaccaro et al. | |
| 7,037,915 B2 | 5/2006 | Hayakawa et al. | |
| 7,091,343 B2 | 8/2006 | Bebbington et al. | |
| 7,105,667 B2 | 9/2006 | Pitts et al. | |
| 7,115,739 B2 | 10/2006 | Bebbington et al. | |
| 7,173,029 B2 | 2/2007 | Hayakawa et al. | |
| 7,208,498 B2 | 4/2007 | Mathvink et al. | |
| 7,223,766 B2 | 5/2007 | Dugar et al. | |
| 7,429,574 B2 | 9/2008 | Castelhano et al. | |
| 2003/0199526 A1 | 10/2003 | Choquette et al. | |
| 2004/0043986 A1 | 3/2004 | Nahra et al. | |
| 2005/0059687 A1 | 3/2005 | Makings et al. | |
| 2005/0153989 A1 | 7/2005 | Grotzfeld et al. | |
| 2005/0187217 A1 | 8/2005 | Wilson et al. | |
| 2005/0277643 A1 | 12/2005 | Kelly et al. | |
| 2006/0128710 A1 | 6/2006 | Lee et al. | |
| 2006/0258658 A1 | 11/2006 | Bebbington et al. | |
| 2007/0037805 A1 | 2/2007 | Hayakawa et al. | |
| 2007/0037834 A1 | 2/2007 | Arai et al. | |
| 2007/0225275 A1 | 9/2007 | Allison et al. | |
| 2008/0039459 A1 | 2/2008 | Folkes et al. | |
| 2008/0070896 A1 | 3/2008 | Yonetoku et al. | |
| 2008/0076758 A1 | 3/2008 | Folkes et al. | |
| 2008/0076768 A1 | 3/2008 | Chuckowree et al. | |
| 2008/0081809 A1 | 4/2008 | Duggan et al. | |
| 2008/0113946 A1 | 5/2008 | Zhang et al. | |

(Continued)

FOREIGN PATENT DOCUMENTS

| | | |
|---|---|---|
| EP | 0 168 500 A1 | 1/1986 |
| EP | 1 277 738 A1 | 1/2003 |

(Continued)

OTHER PUBLICATIONS

"Copy of International Search Report and Written Opinion for International Patent Application No. PCT/EP2010/067159" mailing date Feb. 2, 2011.
Chiang and Abraham, "Targeting the mTOR signaling network in cancer" *Trends in Mol. Med.* 13(10):433-442 (2007).
Guertin and Sabatini, "An expanding role for mTOR in cancer" *Trends in Mol. Med.* 11(8):353-361 (Aug. 2005).
Guertin and Sabatini, "Defining the role of mTOR in cancer" *Cancer Cell* 12:9-22 (Jul. 2007).
Huang and Houghton, "Targeting mTOR signaling for cancer therapy" *Current Opinion in Pharm.* 3:371-377 (2003).

(Continued)

*Primary Examiner* — Susanna Moore
(74) *Attorney, Agent, or Firm* — Lily Ackerman

(57) ABSTRACT

The present invention relates to compounds of Formula I:

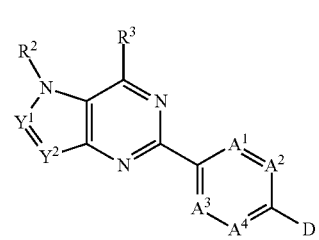

(I)

wherein $R^1$, $R^2$, $R^3$, $A^1$, $A^2$, $A^3$, $A^4$, $Y^1$ and $Y^2$ and D have the meaning described herein. The present invention also relates to pharmaceutical compositions comprising such compounds and therapeutic uses thereof.

11 Claims, 2 Drawing Sheets

(56) References Cited

U.S. PATENT DOCUMENTS

| | | |
|---|---|---|
| 2008/0171743 A1 | 7/2008 | Finlay et al. |
| 2008/0207609 A1 | 8/2008 | Shuttleworth et al. |
| 2008/0207611 A1 | 8/2008 | Shuttleworth et al. |
| 2008/0233127 A1 | 9/2008 | Bursavich et al. |
| 2008/0234262 A1 | 9/2008 | Zask et al. |
| 2008/0242665 A1 | 10/2008 | Bayliss et al. |
| 2008/0267887 A1 | 10/2008 | Yuan et al. |
| 2008/0269210 A1 | 10/2008 | Castanedo et al. |
| 2009/0042884 A1 | 2/2009 | McDonald et al. |
| 2009/0098086 A1 | 4/2009 | Zask et al. |
| 2009/0118275 A1 | 5/2009 | Castanedo et al. |
| 2009/0131429 A1 | 5/2009 | Shutteleworth |
| 2009/0149458 A1 | 6/2009 | Chen et al. |
| 2009/0156601 A1 | 6/2009 | McDonald et al. |
| 2009/0192176 A1* | 7/2009 | Zask et al. .............. 514/260.1 |
| 2010/0069357 A1 | 3/2010 | Bergeron et al. |

FOREIGN PATENT DOCUMENTS

| | | |
|---|---|---|
| FR | 2.450 M | 3/1963 |
| GB | 2 431 156 A | 4/2007 |
| JP | 04-224580 | 8/1992 |
| WO | WO 96/40142 | 12/1996 |
| WO | WO 02/22601 | 3/2002 |
| WO | WO 02/22602 A2 | 3/2002 |
| WO | WO 02/22604 A1 | 3/2002 |
| WO | WO 02/22606 A1 | 3/2002 |
| WO | WO 02/088079 A2 | 11/2002 |
| WO | WO 2005/066171 A1 | 7/2005 |
| WO | WO 2006/035061 A1 | 4/2006 |
| WO | WO 2006/067614 A2 | 6/2006 |
| WO | 2006/073610 A2 | 7/2006 |
| WO | WO 2006/090169 A1 | 8/2006 |
| WO | WO 2006/118598 A1 | 11/2006 |
| WO | WO 2007/080382 A1 | 7/2007 |
| WO | WO 2007/106503 A2 | 9/2007 |
| WO | WO 2007/122410 A1 | 11/2007 |
| WO | WO 2007/132171 A1 | 11/2007 |
| WO | WO 2008/006025 A1 | 1/2008 |
| WO | WO 2008/023159 A1 | 2/2008 |
| WO | WO 2008/023161 A1 | 2/2008 |
| WO | WO 2008/032028 A1 | 3/2008 |
| WO | WO 2008/032033 A1 | 3/2008 |
| WO | WO 2008/032036 A1 | 3/2008 |
| WO | WO 2008/032060 A1 | 3/2008 |
| WO | WO 2008/032072 A1 | 3/2008 |
| WO | WO 2008/032086 A1 | 3/2008 |
| WO | WO 2008/032089 A1 | 3/2008 |
| WO | 2008/115974 A2 | 9/2008 |
| WO | WO 2008/116129 A2 | 9/2008 |
| WO | WO 2008/125833 A1 | 10/2008 |
| WO | WO 2008/125835 A1 | 10/2008 |
| WO | WO 2008/125839 A2 | 10/2008 |
| WO | WO 2008/152387 A1 | 12/2008 |
| WO | WO 2008/152390 A1 | 12/2008 |
| WO | WO 2008/152394 A1 | 12/2008 |
| WO | 2009/052145 A1 | 4/2009 |
| WO | WO 2009/070524 A1 | 6/2009 |
| WO | WO 2009/097490 A1 | 8/2009 |
| WO | 2011/058027 A2 | 5/2011 |

OTHER PUBLICATIONS

Jacinto and Hall, "TOR signalling in bugs, brain and brawn" *Nature Reviews/Mol. Cell Biol.* 4:117-126 (Feb. 2003)

Malagu, K. et al., "The discovery and optimisation of pyrido[2,3,-d]pyrimidine-2,4-diamines as potent and selective inhibitors of mTOR kinase" *Bioorg. Medicinal Chem. Lett.* (doi: 10.1016/j.bmcl.2009.08.038) (2009).

Menear. K.A. et al., "Identification and optimization of novel and selective small molecular weight kinase inhibitors of mTOR" *Bioorg. Medicinal Chem. Lett.* (doi: 10.101006/j.bmcl.2009.08.069) (2009).

Richard, D.J. et al., "Incorporation of water-solubilizing groups in pyrazolopyrimidine mTOR inhibitors: discovery of highly potent and selective analogs with improved human microsomal stability" *Bioorg. & Chem. Let.* 19:6830-6835 (2009).

Zask, A. et al., "ATP-competitive inhibitors of the mammalian target of rapamycin: design and synthesis of highly potent and selective pyrazolopyrimidines" *J. Med. Chem. Let.* 52:5013-5016 (2009).

* cited by examiner

N-7 SUBSTITUTED PURINE AND PYRAZOLOPYRIMINE COMPOUNDS, COMPOSITIONS AND METHODS OF USE

CROSS-REFERENCE TO RELATED APPLICATIONS

This application claims priority to U.S. provisional application 61/260,628 filed on Nov. 12, 2009, and is incorporated herein by reference for all purposes.

BACKGROUND OF INVENTION

The mammalian target of rapamycin (mTOR) is a 289 kDa serine/threonine kinase that is considered a member of the phosphoinositide-3-kinase-like kinase (PIKK) family, because it contains a carboxyl terminal kinase domain that has significant sequence homology to the catalytic domain of phosphoinositide 3-kinase (PI3K) lipid kinases. In addition to the catalytic domain at the C-terminus, mTOR kinase also contains a FKBP12-Rapamycin binding (FRB) domain, a putative repressor domain near the C-terminus and up to 20 tandemly-repeated HEAT motifs at the N-terminus as well as a FRAP-ATM-TRRAP (FAT) and FAT C-terminus domain. See, Huang and Houghton, *Current Opinion in Pharmacology,* 2003, 3, 371-377.) In the literature, mTOR kinase is also referred to as FRAP (FKBP12 and rapamycin associated protein), RAFT1 (rapamycin and FKBP12 target 1), RAPT1 (rapamycin target 1)).

mTOR kinase can be activated by growth factors through the PI3K-Akt pathway or by cellular stresses, such as deprivation of nutrients or hypoxia. The activation of mTOR kinase is thought to play a central role in regulating cell growth and cell survival via a wide range of cellular functions including translation, transcription, mRNA turnover, protein stability, actin cytoskeleton reorganization and autophagy. For a detailed review of mTOR cell signaling biology and potential therapeutic effects of modulating the mTOR signaling interactions, see Sabatini, D. M. and Guertin, D. A. (2005) An Expanding Role for mTOR in Cancer *TRENDS in Molecular Medicine,* 11, 353-361; Chiang, G. C. and Abraham, R. T. (2007) Targeting the mTOR signaling network in cancer TRENDS 13, 433-442; Jacinto and Hall (2005) Tor signaling in bugs, brain and brawn *Nature Reviews Molecular and Cell Biology,* 4, 117-126; and Sabatini, D. M. and Guertin, D. A. (2007) Defining the Role of mTOR in Cancer *Cancer Cell,* 12, 9-22.

Researchers studying mTOR kinase biology have discovered a pathological connection between the dysregulation of mTOR cell signaling and a number of diseases including immunological disorders, cancer, metabolic diseases, cardiovascular diseases and neurological disorders.

For example, there is evidence to show that PI3K-AKT signaling pathway, which lies upstream of mTOR kinase, is frequently overactivated in cancer cells, which subsequently results in the hyperactivation of downstream targets like mTOR kinase. More specifically, the components of the PI3K-AKT pathway that are mutated in different human tumors include, activation mutations of growth factor receptors and the amplification and overexpression of PI3K and AKT. In addition, there is evidence which shows that many tumor types, including glioblastoma, hepatocellular carcinoma, lung carcinoma, melanoma, endometrial carcinomas, and prostate cancer, contain loss-of-function mutations of negative regulators of the PI3K-AKT pathways, such as phosphatases and tensin homolog deleted on chromosome 10 (PTEN) and tuberous sclerosis complex (TSC1/TSC2), which also results in hyperactive signaling of mTOR kinase. The above suggests that inhibitors of mTOR kinase can be effective therapeutics for the treatment of diseases caused, at least in part, by the hyperactivity of the mTOR kinase signaling.

mTOR kinase exists as two physically and functionally distinct signaling complexes (i.e., mTORC1 and mTORC2). mTORC1, also known as the "mTOR-Raptor complex" or the "rapamycin-sensitive complex" because it binds to and is inhibited by the small molecule inhibitor rapamycin. mTORC1 is defined by the presence of the proteins mTOR, Raptor and mLST8. Rapamycin, itself, is a macrolide and was discovered as the first small molecule inhibitor of mTOR kinase. To be biologically active, rapamycin forms a ternary complex with mTOR and FKBP12, which is a cytosolic binding protein collectively called immunophilin. Rapamycin acts to induce the dimerization of mTOR and FKBP12. The formation of rapamycin-FKBP12 complex results in a gain-of-function, because the complex binds directly to mTOR and inhibits the function of mTOR.

A second, more recently discovered mTORC complex, mTORC2, is characterized by the presence of the proteins mTOR, Rictor, Protor-1, mLST8 and mSIN1. mTORC2 is also referred to as the "mTOR-Rictor complex" or the "rapamycin-insensitive" complex because it does not bind to rapamycin.

Both mTOR complexes play important roles in intracellular signaling pathways that affect a cell's growth, and proliferation, and survival. For example, the downstream target proteins of mTORC1 include Ribosomal S6 kinases (e.g., S6K1, S6K2) and eukaryotic initiation factor 4E binding protein (4E-BP 1), which are key regulators of protein translation in cells. Also, mTORC2 is responsible for the phosphorylation of AKT (S473); and studies have shown that uncontrolled cell proliferation due to hyperactivation of AKT to be a hallmark of several cancer types.

Currently, several rapamycin analogues are in clinical development for cancer (e.g., Wyeth's CCI-779, Novartis' RAD001 and Ariad Pharmaceuticals' AP23573). Interestingly, the clinical data shows that the rapamycin analogs appear to be effective for certain cancer types, such as mantle-cell lymphoma, endometrial cancer, and renal cell carcinoma.

The discovery of a second mTOR protein complex (mTORC2) that is not inhibited by rapamycin or its analogs suggest that inhibition of mTOR by rapamycin is incomplete and that a direct mTOR kinase inhibitor which can inhibit both mTORC 1 and mTORC2 at the catalytic ATP binding site can be more efficacious and have broader anti-tumor activity than rapamycin and its analogs.

Recently, small molecule mTOR inhibitors have been disclosed, including in U.S. patent application Ser. Nos. 11/599,663 and 11/657,156 to OSI Pharmaceuticals Inc.; in International Applications WO/2008/023161 and WO/2006/090169 to Kudos Pharmaceuticals; in International Applications WO/2008/032060, WO/2008/032086, WO/2008032033, WO/2008/032028, WO/2008/032036, WO/2008/032089, WO/2008/032072, WO/2008/031091 to AstraZeneca; International publication WO/2008/116129 and U.S. patent application Ser. No. 12/276,459 to Wyeth.

U.S. Provisional Application 61/085,309 discloses a class of N-heterocyclic fused pyrimidine compounds with mTOR activity.

In view of the increased knowledge of the role of mTOR signaling in diseases (e.g., cancer), it is desirable to have small molecule inhibitors of mTOR (including mTORC1 and mTORC2) that can be used to treat diseases wherein aberrant mTOR activity is observed, such as, for example, in cancer. In addition, it can be desirable to have small molecule inhibitors of related enzymes (e.g., PI3K, AKT) that functions upstream or downstream of the mTOR signaling pathway.

SUMMARY OF INVENTION

In one aspect, the present invention provides for a compound of Formula I:

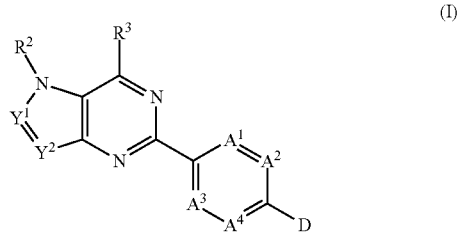

(I)

In Formula I, $Y^1$ and $Y^2$ is each independently N or $C(R^1)$, but $Y^1$ and $Y^2$ are not both N or are not both $C(R^1)$, wherein $R^1$ is selected from the group consisting of hydrogen, $C_{1-6}$ alkyl, $C_{2-6}$ alkenyl, $C_{2-6}$ alkynyl, $C_{1-6}$ heteroalkyl, 6- to 10-membered aryl, 5- to 9-membered heteroaryl, 3- to 12-membered heterocycloalkyl, 3- to 12-membered cycloalkyl, wherein $R^1$ is substituted with from 0 to 5 $R^{R1}$ substituents selected from the group consisting of halogen, F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O, —CN, $R^{c1}$, —$X^1$—$NR^aR^b$, —$X^1$—$SR^a$, —$X^1$—$OR^a$, —$X^1$—$C(O)OR^a$, —$X^1$—$C(O)NR^aR^b$, —$X^1$—$C(O)R^a$, —$X^1$—$NR^aC(O)R^b$, —$X^1$—$OC(O)R^a$, —$X^1$—$NR^aC(O)NR^aR^b$, —$X^1$—$OC(O)NR^aR^b$, —$X^1$—$NR^aS(O)_2NR^aR^b$, —$X^1$—$S(O)_2R^a$, —$X^1$—$S(O)_2NR^aR^b$, —$X^1$—$NO_2$, —$X^1$—$N_3$, —$X^1$—$CN$, and $X^1$—$R^{c1}$; wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^a$ and $R^b$, when attached to the same nitrogen atom are combined to form a 3- to 6-membered heterocyclic ring comprising 1 to 2 heteroatoms selected from N, O and S; $R^c$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; $X^1$ is selected from the group consisting of $C_{1-4}$ alkylene, $C_{2-4}$ alkenylene and $C_{2-4}$ alkynylene; and $R^{c1}$ is selected from the group consisting of phenyl, 2-pyridyl, 3-pyridyl, 4-pyridyl, 2-imidazolyl, 2-indolyl, 1-naphthyl, 2-naphthyl, 2-thienyl, 3-thienyl, 2-pyrrolyl, 2-furanyl and 3-furanyl, and wherein $R^{c1}$ is substituted with from 0 to 3 substituents selected from F, Cl, Br, I, —$NR^aR^b$, —$SR^a$, —$OR^a$, —$S(O)_2R^a$, —$S(O)_2NR^aR^b$, —$NO_2$, —$N_3$, =O, —CN, pyridyl, $C_{1-6}$ alkyl, $C_{2-6}$ alkenyl, $C_{2-6}$ alkynyl and $C_{1-6}$ heteroalkyl. In Formula I, $R^2$ is selected from the group consisting of hydrogen, $C_{1-6}$ alkyl, $C_{2-6}$ alkenyl, $C_{2-6}$ alkynyl, $C_{1-6}$ heteroalkyl, -L-$C_{6-10}$ aryl, -L-$C_{1-9}$ heteroaryl, -L-$C_{3-12}$ cycloalkyl and -L-$C_{2-12}$ heterocycloalkyl, wherein L is selected from $C_{1-6}$ alkylene, $C_{2-6}$ alkenylene, $C_{2-6}$ alkynylene and $C_{1-6}$ heteroalkylene, and wherein $R^2$ is substituted with from 0 to 5 $R^{R2}$ substituents selected from the group consisting of halogen, F, Cl, Br, I, —$NR^dR^e$, —$SR^d$, —$OR^d$, —$C(O)OR^d$, —$C(O)NR^dR^e$, —$C(O)R^d$, —$NR^dC(O)R^e$, —$OC(O)R^f$, —$NR^dC(O)NR^dR^e$, —$OC(O)NR^dR^e$, —$NR^dS(O)_2NR^dR^e$, —$S(O)_2R^d$, —$S(O)_2NR^dR^e$, —$R^f$, —$NO_2$, —$N_3$, =O, —CN, —$X^2$—$NR^dR^e$, —$X^2$—$SR^d$, —$X^2$—$OR^d$, —$X^2$—$C(O)OR^d$, —$X^2$—$C(O)NR^dR^e$, —$X^2$—$C(O)R^d$, —$X^2$—$NR^dC(O)R^e$, —$X^2$—$OC(O)R^f$, —$X^2$—$NR^dC(O)NR^dR^e$, —$X^2$—$OC(O)NR^dR^e$, —$X^2$—$NR^dS(O)_2NR^dR^e$, —$X^2$—$S(O)_2R^d$, —$X^2$—$S(O)_2NR^dR^e$, —$X^2$—$NO_2$, —$X^2$—$N_3$ and —$X^2$—CN; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^d$ and $R^e$, when attached to the same nitrogen atom are combined to form a 3- to 6-membered heterocyclic ring comprising 1 to 2 heteroatoms selected from N, O and S; $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; and $X^2$ is selected from the group consisting of $C_{1-4}$ alkylene, $C_{2-4}$ alkenylene and $C_{2-4}$ alkynylene. $R^3$ is a 5- to 12-membered monocyclic or bridged heterocycloalkyl ring, wherein the $R^3$ group is substituted with from 0 to 3 $R^{R3}$ substituents selected from the group consisting of —$C(O)OR^g$, —$C(O)NR^gR^h$, —$NR^gR^h$, —$OR^g$, —$SR^g$, —$S(O)_2R^i$, —$S(O)R^i$, —$R^i$, halogen, F, Cl, Br, I, —$NO_2$, —CN and —$N_3$, wherein $R^g$ and $R^h$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^g$ and $R^h$, together with the nitrogen atom to which each is attached, are combined to form a 3- to 6-membered heterocyclic ring comprising 1 to 2 heteroatoms selected from N, O and S, and $R^i$ is selected from $C_{1-6}$ alkyl, $C_{1-6}$ haloalkyl, $C_{2-6}$ alkenyl, $C_{3-6}$ cycloalkyl; and when $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S as ring vertices. $A^1$, $A^2$, $A^3$ and $A^4$ are each a member independently selected from N, $C(R^4)$ or C(H), wherein at least three of $A^1$, $A^2$, $A^3$ and $A^4$ is each independently C(H) or $C(R^4)$, wherein $R^4$ at each occurrence is independently selected from the group consisting of F, Cl, Br, I, —$NO_2$, —CN, $C_{1-4}$ alkyl, $C_{2-4}$ alkenyl, $C_{2-4}$ alkynyl, or any two $R^4$ groups attached to adjacent atoms are optionally combined to form a $C_{2-6}$ heterocyclic ring comprising from 1 to 2 heteroatoms selected from N, O and S as ring vertices, $C_{3-7}$ cycloalkyl ring, a $C_{1-5}$ heteroaryl ring comprising from 1 to 4 heteroatoms selected from N, O and S as ring vertices, or phenyl ring. D is a member selected from the group consisting of —$NR^4C(O)NR^5R^6$, —$NR^5R^6$, —$C(O)NR^5R^6$, —$OC(O)OR^5$, —$OC(O)NR^5R^6$, —$NR^4C(=N—CN)NR^5R^6$, —$NR^4C(=N—OR^5)NR^5R^6$, —$NR^4C(=N—NR^5)NR^5R^6$, —$NR^4C(O)R^5$, —$NR^4C(O)OR^5$, —$NR^4S(O)_2NR^5R^6NR^4S(O)_2NR^5R^6$ and —$NR^4S(O)_2R^5$, wherein $R^4$ is selected from the group consisting of hydrogen, $C_{1-6}$ alkyl, $C_{1-6}$ haloalkyl and $C_{2-6}$ alkenyl; $R^5$ and $R^6$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{2-10}$ heterocycloalkyl, $C_{6-10}$ aryl and $C_{1-9}$ heteroaryl, and $R^5$ and $R^6$, when attached to the same nitrogen atom, are optionally combined to form a 5- to 7-membered heterocyclic or a 5- to 9-membered heteroaryl ring comprising 1 to 3 heteroatoms selected from N, O and S as ring vertices and substituted with 0-3 $R^D$ substituents; and wherein $R^4$, $R^5$ and $R^6$ are further substituted with from 0 to 3 $R^D$ substituents, wherein $R^D$ is independently selected from the group consisting of halogen, F, Cl, Br, I, —$NO_2$, —CN, —$NR^jR^k$, —$OR^j$, —$SR^j$, —$C(O)OR^j$, —$C(O)NR^jR^k$, —$NR^jC(O)R^k$, —$NR^jC(O)OR^m$, —$X^3$—$NR^jR^k$, —$X^3$—$OR^j$, —$X^3$—$SR^j$, —$X^3$—$C(O)OR^j$, —$X^3$—$C(O)NR^jR^k$, —$X^3$—$NR^jC(O)R^k$, —$X^3$—$NR^jC(O)OR^k$, —$X^3$—CN, —$X^3$—$NO_2$, —$S(O)R^m$, —$S(O)_2R^m$, =O, and —$R^m$; wherein $R^j$ and $R^k$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{1-9}$ heteroaryl; and $R^m$, at each occurrence, is independently selected from $C_{1-6}$ alkyl, $C_{1-6}$ haloalkyl, $C_{3-7}$ cycloalkyl, $C_{3-7}$ heterocycloalkyl, $C_{6-10}$ aryl and $C_{1-9}$ heteroaryl; $X^3$ is selected from the group consisting of $C_{1-4}$ alkylene, $C_{2-4}$ alkenylene and $C_{2-4}$ alkynylene; and wherein D and a $R^A$ substituent attached to an atom that is adjacent to the atom to which D is attached are optionally combined to form an optionally substituted 5- to 6-membered heterocyclic or heteroaryl ring substituted with from 0 to 4 $R^D$ substituents.

In another aspect, the present invention provides for pharmaceutical compositions comprising at least one pharmaceutically acceptable diluent, carrier or excipient and a compound of Formula I.

In another aspect the present invention provides for methods of using compounds of Formula I, for the treatment of disease or disorders that can be treated by the inhibition of mTOR kinase.

DETAILED DESCRIPTION OF THE INVENTION

Definitions

Figure 1:
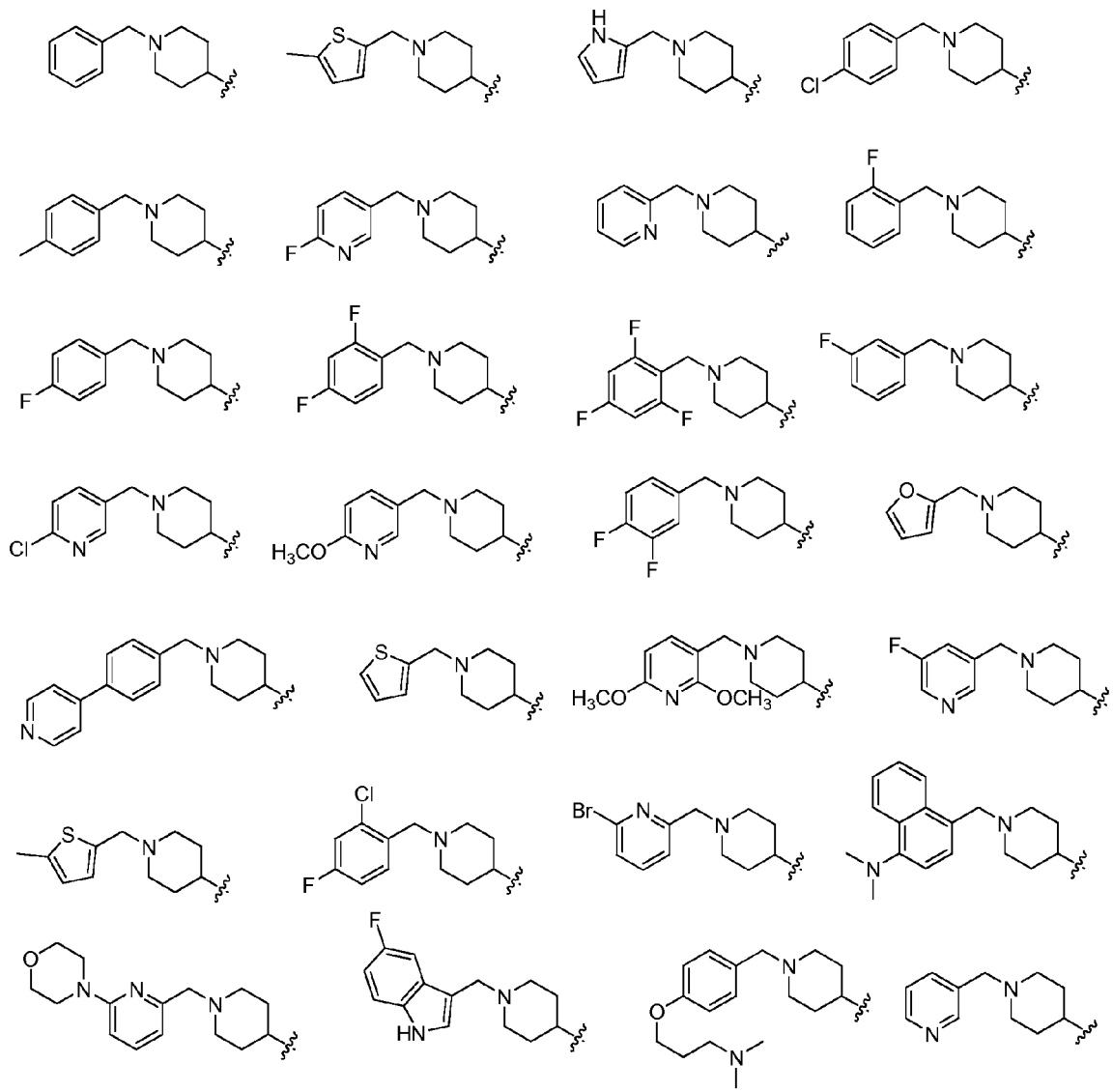
FIG. 1 illustrates certain $R^1$ substituents in compounds of Formula I.

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. The term "cycloalkyl," "carbocyclic," or "carbocycle" refers to hydrocarbon rings having the indicated number of ring atoms (e.g., $C_{3-6}$ cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include $-CH_2-CH_2-O-CH_3$, $-CH_2-CH_2-O-CF_3$, $-CH_2-CH_2-NH-CH_3$, $-CH_2-CH_2-N(CH_3)-CH_3$, $-CH_2-S-CH_2-CH_3$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms can be consecutive, such as, for example, $-CH_2-NH-OCH_3$ and $-CH_2-O-Si(CH_3)_3$.

The term "heterocycloalkyl," "heterocyclic," or "heterocycle" refers to a cycloalkane group that contain from one to five heteroatoms selected from N, O, and S, wherein the nitrogen and sulfur atoms are optionally oxidized, and the nitrogen atom(s) are optionally quaternized. Unless otherwise stated, a "heterocycloalkyl," "heterocyclic," or "heterocycle" ring can be a monocyclic, a bicyclic, spirocyclic or a polycyclic ring system. Non limiting examples of "heterocycloalkyl," "heterocyclic," or "heterocycle" rings include pyrrolidine, piperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and poly-halogenated variants thereof.

The term "alkylene" by itself or as part of another substituent means a divalent radical derived from an alkane, as exemplified by $-CH_2CH_2CH_2CH_2-$. Typically, an alkyl (or alkylene) group will have from 1 to 24 carbon atoms, with those groups having 10 or fewer carbon atoms being preferred in the present invention. "Haloalkylene" refers to mono and poly halogenated variant of alkylene. "Alkenylene" and "alkynylene" refer to the unsaturated forms of "alkylene" having double or triple bonds, respectively and are also meant to include mono and poly-halogenated variants.

The term "heteroalkylene" by itself or as part of another substituent means a divalent radical, saturated or unsaturated or polyunsaturated, derived from heteroalkyl, as exemplified by $-CH_2-CH_2-S-CH_2CH_2-$ and $-CH_2-S-CH_2-CH_2-NH-CH_2-$, $-O-CH_2-CH=CH-$, $-CH_2-CH=C(H)CH_2-O-CH_2-$ and $-S-CH_2-C\equiv C-$. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as $-NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon group, which can be a single ring or multiple rings (up to three rings) which are fused together. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, —OR', —NR'R", —SR', —SiR'R"R"', —OC(O)R', —C(O)R', —CO$_2$R', —CONR'R", —OC(O)NR'R", —NR"C(O)R', —NR'''C(O)NR'R", —NR"C(O)$_2$R', —NHC(NH$_2$)=NH, —NRC(NH$_2$)=NH, —NHC(NH$_2$)=NR', —NR"C(NR'R")=N—CN, —NR"C(NR'R")=NOR', —NHC(NH$_2$)=NR', —S(O)R', —S(O)$_2$R', —S(O)$_2$NR'R", —NR'S(O)$_2$R", —NR'''S(O)$_2$NR'R", —CN, —NO$_2$, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R"', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to (2 m'+1), where m' is the total number of carbon atoms in such radical. R', R" and R''' each independently refer groups including, for example, hydrogen, unsubstituted C$_{1-6}$ alkyl, unsubstituted heteroalkyl, unsubstituted aryl, aryl substituted with 1-3 halogens, unsubstituted C$_{1-6}$ alkyl, C$_{1-6}$ alkoxy or C$_{1-6}$ thioalkoxy groups, or unsubstituted aryl-C$_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substitutents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene linker (e.g., —(CH$_2$)$_{1-4}$—NR'R"), the alkylene linker includes halo variants as well. For example, the linker "—(CH$_2$)$_{1-4}$—" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R''', —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-C$_{1-4}$ alkoxy, and perfluoro-C$_{1-4}$ alkyl, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R"', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to the total number of open valences on the aromatic ring system; and where R', R" and R''' are independently selected from hydrogen, C$_{1-6}$ alkyl, C$_{3-6}$ cycloalkyl, C$_{2-6}$ alkenyl, C$_{2-6}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —(CH$_2$)$_{1-4}$—NR'R"), the alkylene linker includes halo variants as well. For example, the linker "—(CH$_2$)$_{1-4}$-" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a squiggly line "〰" that intersects a bond in a chemical structure indicate the point of attachment of the atom to which the bond is connected in the chemical structure to the remainder of a molecule, or to the remainder of a fragment of a molecule.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino ($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug can reduce the number of cancer cells; reduce the tumor size; inhibit (i.e., slow to some extent and preferably stop)

cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used herein, the term "adjunct" relates to the use of active compounds in conjunction with known therapeutic means. Such means include cytotoxic regimes of drugs and/or ionising radiation as used in the treatment of different cancer types. Examples of chemotherapeutic agents that can be combined with compounds of the invention include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole;

Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors, for example a PI3K inhibitor, a MEK inhibitor, etc; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Active compounds can also be used as cell culture additives to inhibit mTOR, for example, in order to sensitize cells to known chemotherapeutic agents or ionising radiation treatments in vitro.

I.A COMPOUNDS

In one aspect, the present invention provides for a compound of Formula I:

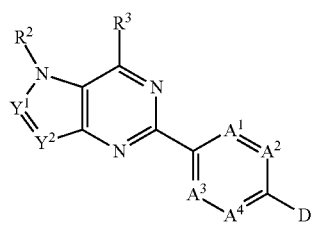

(I)

In Formula I, $Y^1$ and $Y^2$ is each independently N or $C(R^1)$, but $Y^1$ and $Y^2$ are not both N or are not both $C(R^1)$, wherein $R^1$ is selected from the group consisting of hydrogen, $C_{1-6}$ alkyl, $C_{2-6}$ alkenyl, $C_{2-6}$ alkynyl, $C_{1-6}$ heteroalkyl, 6- to 10-membered aryl, 5- to 9-membered heteroaryl, 3- to 12-membered heterocycloalkyl, wherein $R^1$ is substituted with from 0 to 5 $R^{R1}$ substituents selected from the group consisting of halogen, F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O, —CN, $R^{c1}$, —$X^1$—$NR^aR^b$, —$X^1$—$SR^a$, —$X^1$—$OR^a$, —$X^1$—$C(O)OR^a$, —$X^1$—$C(O)NR^aR^b$, —$X^1$—$C(O)R^a$, —$X^1$—$NR^aC(O)R^b$, —$X^1$—$OC(O)R^a$, —$X^1$—$NR^aC(O)NR^aR^b$, —$X^1$—$OC(O)NR^aR^b$, —$X^1$—$NR^aS(O)_2NR^aR^b$, —$X^1$—$S(O)_2R^a$, —$X^1$—$S(O)_2NR^aR^b$, —$X^1$—$NO_2$, —$X^1$—$N_3$, —$X^1$—CN, and $X^1$—$R^{c1}$; wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^a$ and $R^b$, when attached to the same nitrogen atom are combined to form a 3- to 6-membered heterocyclic ring comprising 1 to 2 heteroatoms selected from N, O and S; $R^c$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; $X^1$ is selected from the group consisting of $C_{1-4}$ alkylene, $C_{2-4}$ alkenylene and $C_{2-4}$ alkynylene; and $R^{c1}$ is selected from the group consisting of phenyl, 2-pyridyl, 3-pyridyl, 4-pyridyl, 2-imidazolyl, 2-indolyl, 1-naphthyl, 2-naphthyl, 2-thienyl, 3-thienyl, 2-pyrrolyl, 2-furanyl and 3-furanyl, and wherein $R^{c1}$ is substituted with from 0 to 3 substituents selected from F, Cl, Br, I, —$NR^aR^b$, —$SR^a$, —$OR^a$, —$S(O)_2R^a$, —$S(O)_2NR^aR^b$, —$NO_2$, —$N_3$, =O, —CN, pyridyl, $C_{1-6}$ alkyl, $C_{2-6}$ alkenyl, $C_{2-6}$ alkynyl and $C_{1-6}$ heteroalkyl. In Formula I, $R^2$ is selected from the group consisting of hydrogen, $C_{1-6}$ alkyl, $C_{2-6}$ alkenyl, $C_{2-6}$ alkynyl, $C_{1-6}$ heteroalkyl, -L-$C_{6-10}$ aryl, -L-$C_{1-9}$ heteroaryl, -L-$C_{3-12}$ cycloalkyl and -L-$C_{2-12}$ heterocycloalkyl, wherein L is selected from $C_{1-6}$ alkylene, $C_{2-6}$ alkenylene, $C_{2-6}$ alkynylene and $C_{1-6}$ heteroalkylene, and wherein $R^2$ is substituted with from 0 to 5 $R^{R2}$ substituents selected from the group consisting of halogen, F, Cl, Br, I, —$NR^dR^e$, —$SR^d$, —$OR^d$, —$C(O)OR^d$, —$C(O)NR^dR^e$, —$C(O)R^d$, —$NR^dC(O)R^e$, —$OC(O)R^f$, —$NR^dC(O)NR^dR^e$, —$OC(O)NR^dR^e$, —$NR^dS(O)_2NR^dR^e$, —$S(O)_2R^d$, —$S(O)_2NR^dR^e$, —$R^f$, —$NO_2$, —$N_3$, =O, —CN, —$X^2$—$NR^dR^e$, —$X^2$—$SR^d$, —$X^2$—$OR^d$, —$X^2$—$C(O)OR^d$, —$X^2$—$C(O)NR^dR^e$, —$X^2$—$C(O)R^d$, —$X^2$—$NR^dC(O)R^e$, —$X^2$—$OC(O)R^d$, —$X^2$—$NR^dC(O)NR^dR^e$, —$X^2$—$OC(O)NR^dR^e$, —$X^2$—$NR^dS(O)_2NR^dR^e$, —$X^2$—$S(O)_2R^d$, —$X^2$—$S(O)_2NR^dR^e$, —$X^2$—$NO_2$, —$X^2$—$N_3$ and —$X^2$—CN; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^d$ and $R^e$, when attached to the same nitrogen atom are combined to form a 3- to 6-membered heterocyclic ring comprising 1 to 2 heteroatoms selected from N, O and S; $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; and $X^2$ is selected from the group consisting of $C_{1-4}$ alkylene, $C_{2-4}$ alkenylene and $C_{2-4}$ alkynylene. $R^3$ is a 5- to 12-membered monocyclic or bridged heterocycloalkyl ring, wherein the $R^3$ group is substituted with from 0 to 3 $R^{R3}$ substituents selected from the group consisting of —$C(O)OR^g$, —$C(O)NR^gR^h$, —$NR^gR^h$, —$OR^g$, —$SR^g$, —$S(O)_2R^i$, —$S(O)R^i$, —$R^i$, halogen, F, Cl, Br, I, —$NO_2$, —CN and —$N_3$, wherein $R^g$ and $R^h$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^g$ and $R^h$, together with the nitrogen atom to which each is attached, are combined to form a 3- to 6-membered heterocyclic ring comprising 1 to 2 heteroatoms selected from N, O and S, and $R^i$ is selected from $C_{1-6}$ alkyl, $C_{1-6}$ haloalkyl, $C_{2-6}$ alkenyl, $C_{3-6}$ cycloalkyl; and when $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S as ring vertices. $A^1$, $A^2$, $A^3$ and $A^4$ are each a member independently selected from N, $C(R^4)$ or C(H), wherein at least three of $A^1$, $A^2$, $A^3$ and $A^4$ is each independently C(H) or $C(R^4)$, wherein $R^4$ at each occurrence is independently selected from the group consisting of F, Cl, Br, I, —$NO_2$, —CN, $C_{1-4}$ alkyl, $C_{2-4}$ alkenyl, $C_{2-4}$ alkynyl, or any two $R^4$ groups attached to adjacent atoms are optionally combined to form a $C_{2-6}$ heterocyclic ring comprising from 1 to 2 heteroatoms selected from N, O and S as ring vertices, $C_{3-7}$ cycloalkyl ring, a $C_{1-5}$ heteroaryl ring comprising from 1 to 4 heteroatoms selected from N, O and S as ring vertices, or phenyl ring. D is a member selected from the group consisting of —$NR^4C(O)NR^5R^6$, —$NR^5R^6$, —$C(O)NR^5R^6$, —$OC(O)OR^5$, —$OC(O)NR^5R^6$, —$NR^4C(=N—CN)NR^5R^6$, —$NR^4C(=N—OR^5)NR^5R^6$, —$NR^4C(=N—NR^5)NR^5R^6$, —$NR^4C(O)R^5$, —$NR^4C(O)OR^5$, —$NR^4S(O)_2NR^5R^6$ and —$NR^4S(O)_2R^5$, wherein $R^4$ is selected from the group consisting of hydrogen, $C_{1-6}$ alkyl, $C_{1-6}$ haloalkyl and $C_{2-6}$ alkenyl; $R^5$ and $R^6$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{2-10}$ heterocycloalkyl, $C_{6-10}$ aryl and $C_{1-9}$ heteroaryl, and $R^5$ and $R^6$, when attached to the same nitrogen atom, are optionally combined to form a 5- to 7-membered heterocyclic or a 5- to 9-membered heteroaryl ring comprising 1 to 3 heteroatoms selected from N, O and S as ring vertices and substituted with 0-3 $R^D$ substituents; and wherein $R^4$, $R^5$ and $R^6$ are further substituted with from 0 to 3 $R^D$ substituents, wherein $R^D$ is independently selected from the group consisting of halogen, F, Cl, Br, I, $-NO_2$, $-CN$, $-NR^jR^k$, $-OR^j$, $-SR^j$, $-C(O)OR^j$, $-C(O)NR^jR^k$, $-NR^jC(O)R^k$, $-NR^jC(O)OR^m$, $-X^3-NR^jR^k$, $-X^3-OR^j$, $-X^3-SR^j$, $-X^3-C(O)OR^j$, $-X^3-C(O)NR^jR^k$, $-X^3-NR^jC(O)R^k$, $-X^3-NR^jC(O)OR^k$, $-X^3-CN$, $-X^3-NO_2$, $-S(O)R^m$, $-S(O)_2R^m$, $=O$, and $-R^m$; wherein $R^j$ and $R^k$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{1-9}$ heteroaryl; and $R^m$, at each occurrence, is independently selected from $C_{1-6}$ alkyl, $C_{1-6}$ haloalkyl, $C_{3-7}$ cycloalkyl, $C_{3-7}$ heterocycloalkyl, $C_{6-10}$ aryl and $C_{1-9}$ heteroaryl; and $X^3$ is selected from the group consisting of $C_{1-4}$ alkylene, $C_{2-4}$ alkenylene and $C_{2-4}$ alkynylene, and wherein D and a $R^A$ substituent attached to an atom that is adjacent to the atom to which D is attached are optionally combined to form an optionally substituted 5- to 6-membered heterocyclic or heteroaryl ring substituted with from 0 to 4 $R^D$ substituents.

In one embodiment, compounds of Formula I are of Formula I-A:

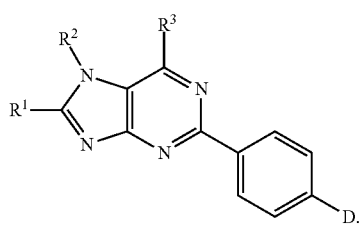

(I-A)

In another embodiment, compounds of Formula I are of Formula I-B:

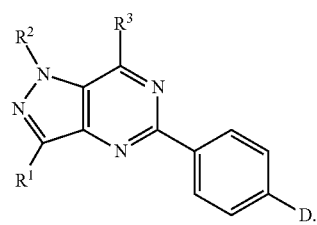

(I-B)

In another embodiment, in compounds of Formula I, I-A and I-B, $R^3$ is selected from the group consisting of morpholin-4-yl, 3,4-dihydro-2H-pyran-4-yl, 3,6-dihydro-2H-pyran-4-yl, tetrahydro-2H-pyran-4-yl, 1,4-oxazepan-4-yl, 2-oxa-5-azabicyclo[2.2.1]heptan-5-yl, 3-oxa-8-azabicyclo[3.2.1]octan-8-yl, piperidin-1-yl and 8-oxa-3-azabicyclo[3.2.1]octan-3-yl, wherein the $R^3$ group is substituted with from 0 to 3 $R^{R3}$ substituents selected from the group consisting of $-C(O)OR^g$, $-C(O)NR^gR^h$, $-NR^gR^h$, $-OR^g$, $-SR^g$, $-S(O)_2R^i$, $-S(O)R^i$, $-R^i$, halogen, F, Cl, Br, I, $-NO_2$, $-CN$ and $-N_3$, wherein $R^g$ and $R^h$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^g$ and $R^h$, together with the nitrogen atom to which each is attached, are combined to form a 3- to 6-membered heterocyclic ring comprising 1 to 2 heteroatoms selected from N, O and S, and $R^i$ is selected from $C_{1-6}$ alkyl, $C_{1-6}$ haloalkyl, $C_{2-6}$ alkenyl, $C_{3-6}$ cycloalkyl; and if $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S as ring vertices. In certain aspects of this embodiment, $R^3$ is substituted with from 0 to 2 $R^{R3}$ substituents selected from $-NR^gR^h$, $-OR^9$, and $R^i$, and if $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S as ring vertices. In certain aspects of this embodiment, $R^3$ is selected from the group consisting of morpholin-4-yl, 3(R)-methyl-morpholin-4-yl, 3(S)-methyl-morpholin-4-yl, 3(R)-ethyl-morpholin-4-yl, 3(S)-ethyl-morpholin-4-yl, 3(R)-isopropyl-morpholin-4-yl, 3(S)-isopropyl-morpholin-4-yl, 3,3-dimethyl-morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, 2-oxa-5-azabicyclo[2.2.1]heptan-5-yl, 3-oxa-8-azabicyclo[3.2.1]octan-8-yl, 4-methoxy-piperidin-1-yl and 8-oxa-3-azabicyclo[3.2.1]octan-3-yl.

In another embodiment, compounds of Formula I are selected from the group consisting of

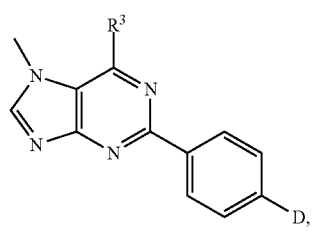

II-A

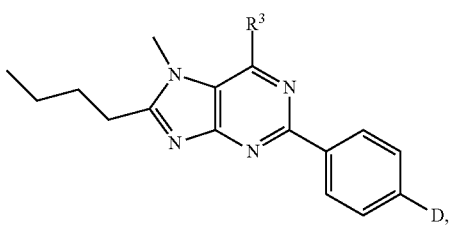

II-B

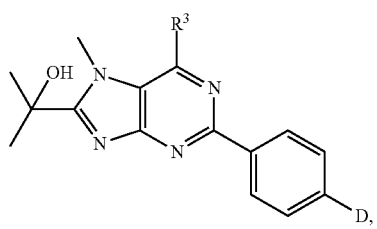

II-C

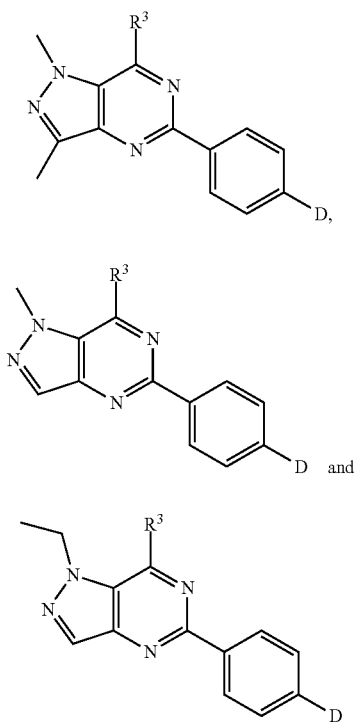

In another embodiment, in compounds of Formula I, I-A or I-B, D is selected from the group consisting of —NR⁴C(O)NR⁵R⁶, —NR⁵R⁶, —C(O)NR⁵R⁶, —NR⁴C(=N—CN)NR⁵R⁶, —NR⁴C(O)R⁵, —NR⁴C(O)OR⁵, —NR⁴S(O)₂NR⁵R⁶ and —NR⁴S(O)₂R⁵.

In another embodiment, in compounds of Formula I, D is —NR⁴C(O)NR⁵R⁶ or —NR⁵R⁶, wherein R⁴ is hydrogen, R⁵ and R⁶ are each independently an optionally substituted group selected from the group consisting of hydrogen, C₁₋₆ alkyl, C₁₋₆ heteroalkyl, C₁₋₆ haloalkyl, C₃₋₇ cycloalkyl, C₂₋₇ heterocycloalkyl, C₆₋₁₀ aryl, and C₁₋₉ heteroaryl, and R⁵ and R⁶, when attached to the same nitrogen atom, are optionally combined to form an a 5- to 7-heterocyclic ring or a 5- to 9-membered heteroaryl ring comprising 1 to 3 heteroatoms selected from N, O and S as ring vertices and is substituted with from 0 to 3 R^D substituents. In certain aspects of this embodiment, D is —NR⁵R⁶, wherein R⁵ is hydrogen or C₁₋₃ alkyl, and R⁶ is an optionally substituted C₆₋₁₀ aryl, C₁₋₉ heteroaryl or C₃₋₇ heterocycloalkyl. In certain aspects of this embodiment, D is —NR⁵R⁶, wherein R⁵ is hydrogen or C₁₋₃ alkyl, and R⁶ is an optionally substituted C₃₋₇ heterocycloalkyl selected from the group consisting of:

wherein a hydrogen atom attached to one or more nitrogen or carbon ring vertices in the C₃₋₇ heterocycloalkyl ring is optionally replaced with a R^D substituent selected from the group consisting of F, Cl, Br, I, —NR^jR^k, —OR^j and R^s. In certain aspects of this embodiment, D is selected from the group consisting of

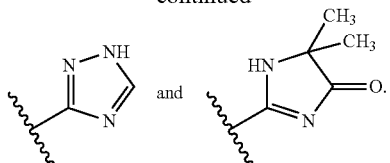

In another embodiment, in compounds of Formula I, D is —NR⁵R⁶, wherein R⁵ and R⁶ are combined to form an optionally substituted 5-membered heteroaryl ring selected from the group consisting of pyrrolyl, pyrazolyl, imidazolyl and triazolyl.

In another embodiment, in compounds of Formula I, D is —NR⁴C(O)NR⁵R⁶, wherein R⁴ is hydrogen; R⁵ and R⁶ are each independently an optionally substituted group selected from the group consisting of hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, a 5- to 6-membered heteroaryl, and optionally substituted phenyl. In certain aspects of this embodiment, one of R⁵ and R⁶ is hydrogen. In certain aspects of this embodiment, R⁴ and R⁵ are each hydrogen and R⁶ is an optionally substituted group selected from $C_{1-6}$ alkyl and $C_{1-6}$ haloalkyl. In certain aspects of the embodiment, R⁶ is selected from the group consisting of

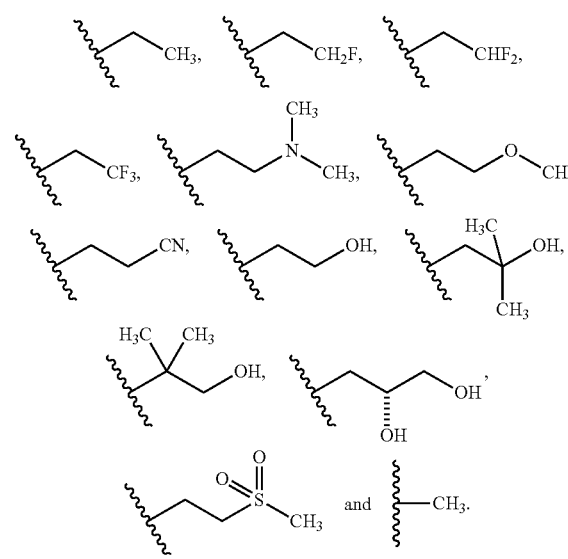

In certain aspects of this embodiment, R⁶ is ethyl.

In another embodiment, in compounds of Formula I, D is —NR⁴C(O)NR⁵R⁶, wherein R⁴ is hydrogen and R⁵ is hydrogen or $C_{1-3}$ alkyl and R⁶ is an optionally substituted group selected from the group consisting of optionally substituted isoxazol-3-yl, isoxazol-4-yl isoxazol-5-yl, oxazol-2-yl, oxazol-4-yl, oxazol-5-yl, pyrazol-3-yl, pyrazol-4-yl, pyrazol-5-yl, 1,2,3-oxadiazol-4-yl, 1,2,3-oxadiazol-5-yl, 1,3,4-oxadiazol-2-yl, 1,3,4-oxadiazol-5-yl, 2-pyridyl, 3-pyridyl, 4-pyridyl, 5-pyridyl, cyclobutyl, cyclopentyl, cyclohexyl, 2-oxepanyl, 3-oxepanyl, 2-tetrahydrofuranyl, 3-tetrahydrofuranyl and phenyl. In certain aspects of this embodiment, R⁶ is independently substituted with from 0 to 3 substituents selected from F, Cl, Br, I, —CN, —NR$^j$R$^k$ and —OR$^j$. In certain aspects of this embodiment, R⁶ is selected from the group consisting of

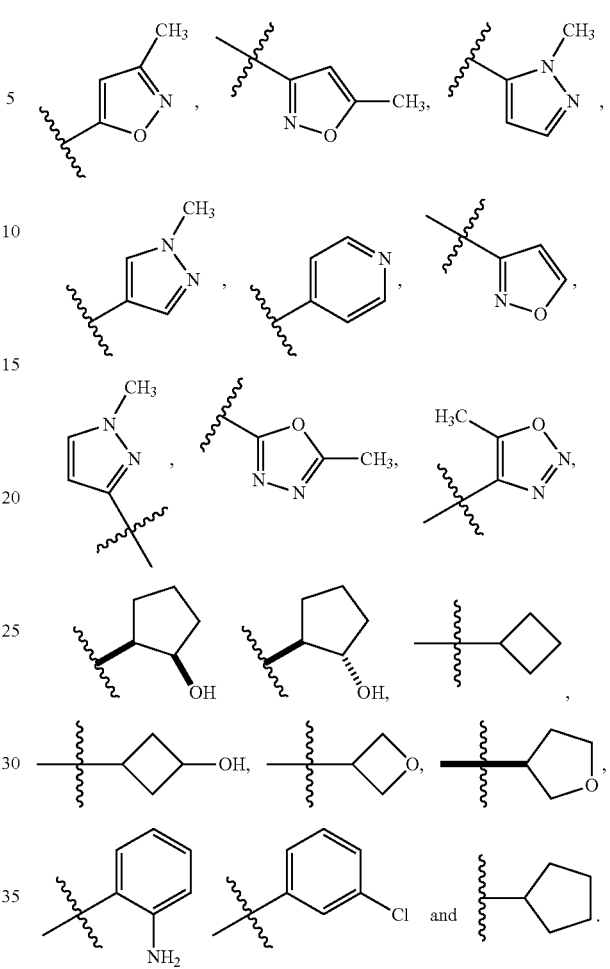

Figure 2:
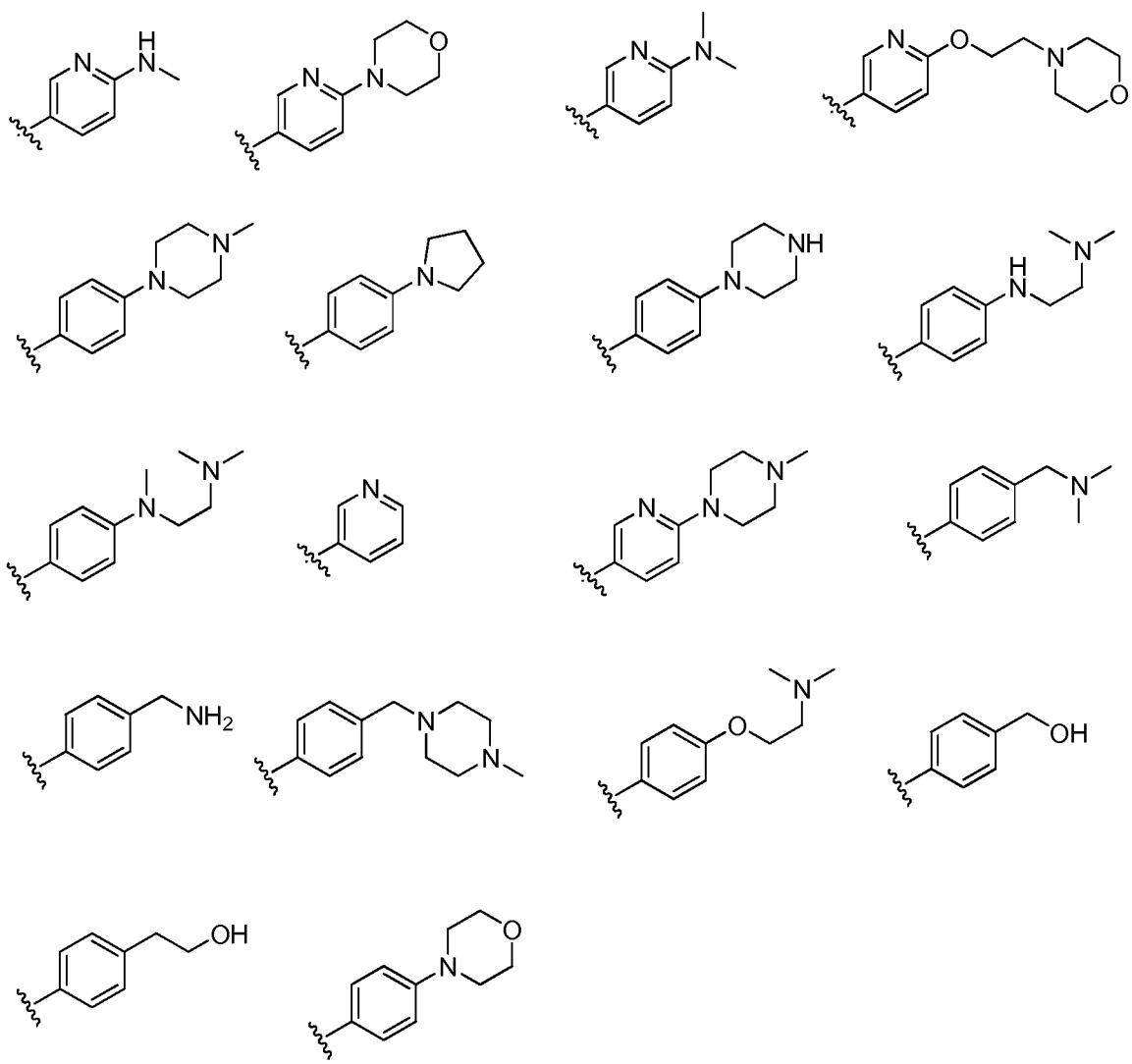
FIG. 2 illustrates certain $R^5$ or $R^6$ groups when D in Formula I is $-NR^4C(O)NR^5R^6$.

In another embodiment, in compounds of Formula I, D is —NR⁴C(O)NR⁵R⁶, wherein R⁴ is hydrogen, R⁵ is hydrogen or $C_{1-3}$ alkyl and R⁶ is selected from the group set forth in FIG. 2.

In another embodiment, in compounds of Formula I, D and a R$^A$ substituent attached to an atom that is adjacent to the atom to which D is attached are optionally combined to form an optionally substituted 5- to 6-membered heterocyclic or heteroaryl ring substituted with from 0 to 4 R$^D$ substituentsand. Within certain aspects of this embodiment, the 5- to 6-membered heterocyclic or heteroaryl ring formed is selected from the group consisting of optionally substituted imidazolidinone, pyrazole, imidazole, pyrrolidinone and pyrimidine. Within another aspect of this embodiment, D and a R$^A$ substituent attached to an atom that is adjacent to the atom to which D is attached are optionally combined to form an optionally substituted 5- to 6-membered heterocyclic or heteroaryl ring selected from the group consisting of:

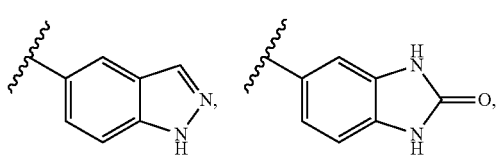

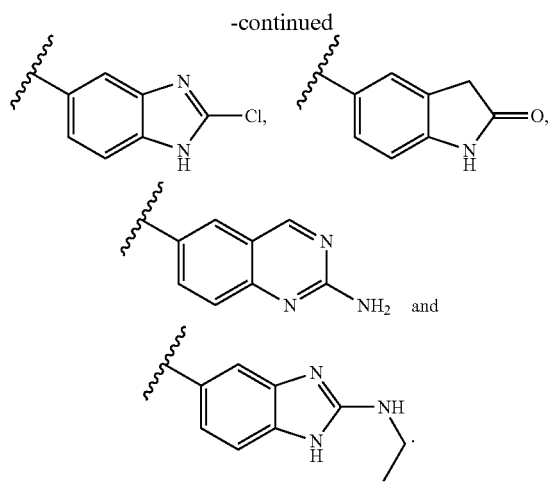

In another embodiment, in compounds of Formula I, I-A or I-B, $R^1$ is selected from the group consisting of hydrogen, $C_{1-6}$ alkyl, $C_{2-6}$ alkenyl, $C_{2-6}$ alkynyl, $C_{1-6}$ heteroalkyl, phenyl, 5- to 6-membered heteroaryl, 3- to 7-membered heterocycloalkyl, 3- to 7-membered cycloalkyl, wherein $R^1$ is substituted with from 0 to 5 $R^{R1}$ substituents selected from the group consisting of halogen, F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O, —CN, $R^{c1}$, —$X^1$—$NR^aR^b$, —$S^1$—$SR^a$, —$X^1$—$OR^a$, —$X^1$—$C(O)OR^a$, —$X^1$—$C(O)NR^aR^b$, —$X^1$—$C(O)R^a$, —$X^1$—$NR^aC(O)R^b$, —$X^1$—$OC(O)R^a$, —$X^1$—$NR^aC(O)_2NR^aR^b$, —$X^1$—$NR^aS(O)_2NR^aR^b$, —$X^1$—$S(O)_2R^a$, —X—$S(O)_2NR^aR^b$, —$X^1$—$NO_2$, —$X^1$—CN, and $X^1$—$R^{c1}$; wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^a$ and $R^b$, when attached to the same nitrogen atom are combined to form a 3- to 6-membered heterocyclic ring comprising 1 to 2 heteroatoms selected from N, O and S; $R^c$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; $X^1$ is selected from the group consisting of $C_{1-4}$ alkylene, $C_{2-4}$ alkenylene and $C_{2-4}$ alkynylene, and $R^{c1}$ is selected from the group consisting of phenyl, 2-pyridyl, 3-pyridyl, 4-pyridyl, 2-imidazolyl, 2-indolyl, 1-naphthyl, 2-naphthyl, 2-thienyl, 3-thienyl, 2-pyrrolyl, 2-furanyl and 3-furanyl, and wherein $R^{c1}$ is substituted with from 0 to 3 substituents selected from F, Cl, Br, I, —$NR^aR^b$, —$SR^a$, —$OR^a$, —$S(O)_2R^a$, —$S(O)_2NR^aR^b$, —$NO_2$, —$N_3$, =O, —CN, $C_{1-6}$ alkyl, $C_{2-6}$ alkenyl, $C_{2-6}$ alkynyl and $C_{1-6}$ heteroalkyl. $R^2$ is selected from the group consisting of hydrogen, $C_{1-6}$ alkyl, $C_{2-6}$ alkenyl, $C_{2-6}$ alkynyl and $C_{1-6}$ heteroalkyl, and wherein $R^2$ is substituted with from 0 to 3 $R^{R2}$ substituents selected from the group consisting of halogen, F, Cl, Br, I, —$NR^dR^e$, —$SR^d$, —$OR^d$, —$C(O)OR^d$, —$C(O)NR^dR^e$, —$C(O)R^d$, —$NR^dC(O)R^e$, —$OC(O)R^f$, —$NR^dC(O)NR^dR^e$, —$OC(O)NR^dR^e$, —$NR^dS(O)_2NR^dR^e$, —$S(O)_2R^d$, —$S(O)_2NR^dR^e$, —$R^f$, —$NO_2$, —$N_3$, =O and —CN; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^d$ and $R^e$, when attached to the same nitrogen atom are combined to form a 3- to 6-membered heterocyclic ring comprising 1 to 2 heteroatoms selected from N, O and S; and $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl. In certain aspects of this embodiment, $R^1$ is selected from the group consisting of hydrogen, $C_{1-6}$ alkyl, $C_{2-6}$ alkenyl, $C_{2-6}$ alkynyl, $C_{1-6}$ heteroalkyl, wherein $R^1$ is substituted with from 0 to 5 $R^{R1}$ substituents selected from the group consisting of halogen, F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O—CN and $X^1$-$R^{c1}$; and $R^2$ is selected from the group consisting of hydrogen, $C_{1-6}$ alkyl, $C_{2-6}$ alkenyl, $C_{2-6}$ alkynyl, $C_{1-6}$ heteroalkyl and is substituted with from 0 to 3 $R^{R2}$ substituents. In certain aspects of this embodiment, $R^1$ is selected from the group consisting of hydrogen, methyl, ethyl, propyl, isopropyl, 2-hydroxyprop-2-yl, butyl, sec-butyl, tert-butyl, isobutyl, pentyl, dimethylaminomethyl and hexyl. In certain aspects of this embodiment, $R^1$ is selected from the group consisting of cyclopropyl, cyclobutyl, cyclopentyl, cyclohexyl, azetidin-1-yl, azetidin-2-yl, azetidin-3-yl, pyrrolidin-1-yl, pyrrolidin-2-yl, pyrrolidin-3-yl, piperidin-1-yl, piperidin-2-yl, piperidin-3-yl, piperidin-4-yl, oxetan-2-yl, oxetan-3-yl, tetrahydrofuran-2-yl, tetrahydrofuran-3-yl, tetrahydropyran-2-yl, tetrahydropyran-3-yl and tetrahydropyran-4-yl, oxepan-2-yl, oxepan-3-yl, oxepan-4-yl, phenyl, pyrrol-2-yl, pyrrol-3-yl, pyrazol-3-yl, pyrazol-4-yl, pyrazol-5-yl, furan-2-yl, furan-3-yl, thien-2-yl, thien-3-yl, thiazol-2-yl, thiazol-3-yl, thiazol-4-yl, imiazol-1-yl, imidazol-4-yl, pyrid-2-yl, pyrid-3-yl, pyrid-4$Y^1$, pyrimidin-1-yl, pyrimidin-2-yl, pyrimidin-3-yl, pyrazin-2-yl, pyridazin-2-yl, pyridazin-3-yl and triazin-2-yl, wherein $R^1$ is substituted with from 0 to 3 $R^{R1}$ substituents; and $R^2$ is selected from the group consisting of hydrogen, $C_{1-6}$ alkyl, $C_{2-6}$ alkenyl, $C_{2-6}$ alkynyl, $C_{1-6}$ heteroalkyl and is substituted with from 0 to 3 $R^{R2}$ substituents. In certain aspects of this embodiment, $R^1$ is selected from the group consisting of:

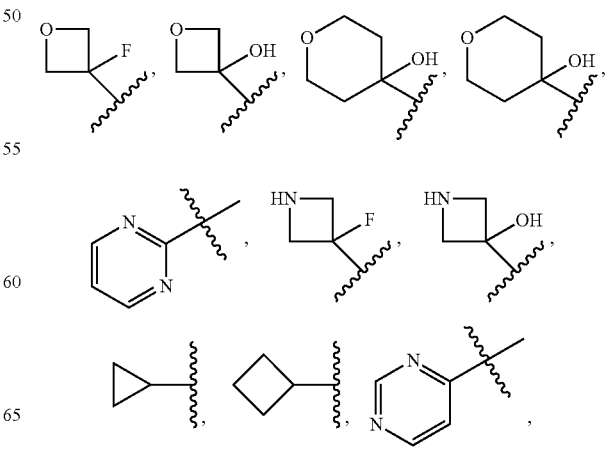

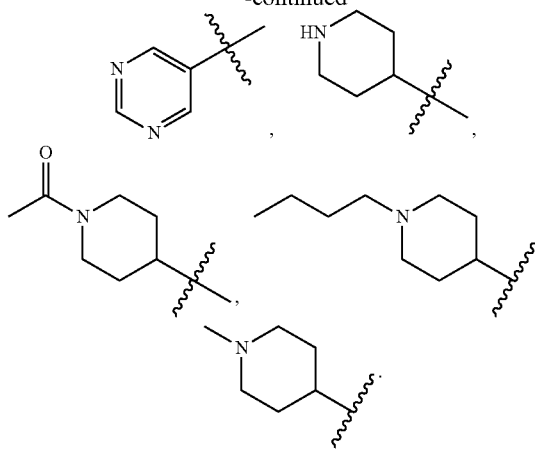

In certain aspects of this embodiment, $R^1$ is selected from the group set forth in FIG. 1.

In another embodiment, in compounds of Formula I, $R^1$ is selected from the group consisting of hydrogen, $C_{1-6}$ alkyl, $C_{2-6}$ alkenyl, $C_{2-6}$ alkynyl, $C_{1-6}$ heteroalkyl, wherein $R^1$ is substituted with from 0 to 5 $R^{R1}$ substituents selected from the group consisting of halogen, F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O—CN and $X^1$—$R^{c1}$; and $R^2$ is selected from the group consisting of hydrogen,

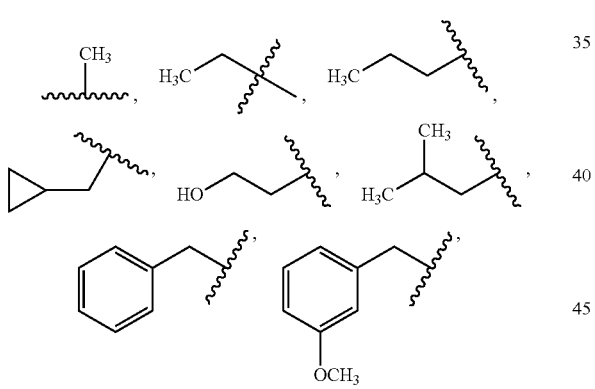

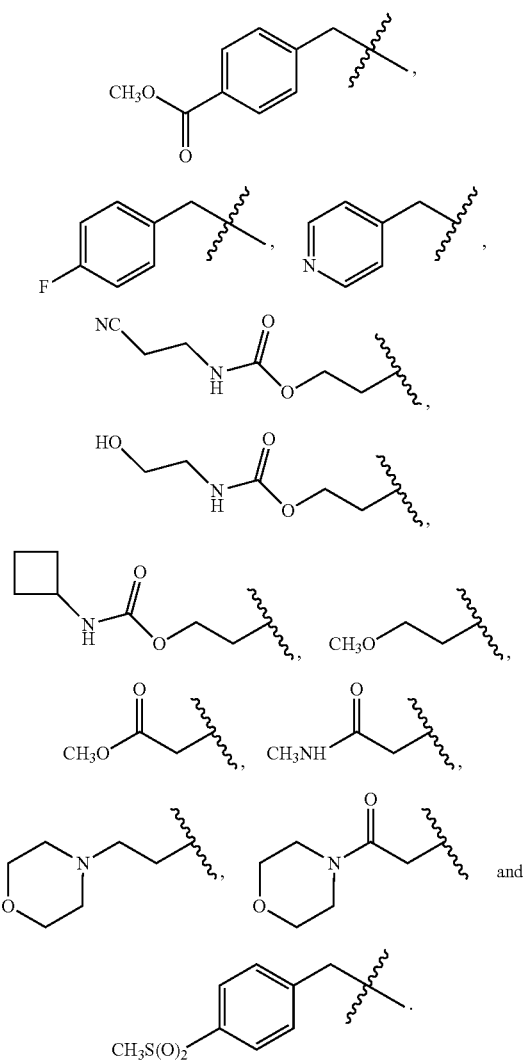

In certain aspect of this embodiment, $R^2$ is selected from the group consisting of hydrogen, methyl, ethyl, propyl, isopropyl, cyclopropylmethyl, and methoxyethyl.

In another embodiment, compounds of Formula I are selected from Table 1.

TABLE 1

| No | Structure | Name |
|---|---|---|
| 101 | 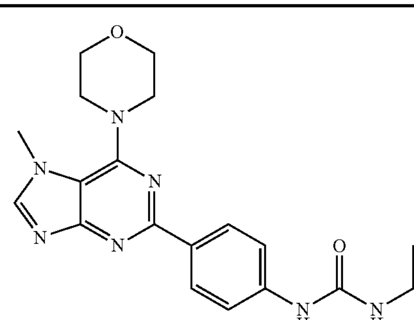 | 1-ethyl-3-(4-(7-methyl-6-morpholino-7H-purin-2-yl)phenyl)urea |

TABLE 1-continued

| No | Structure | Name |
|---|---|---|
| 102 | 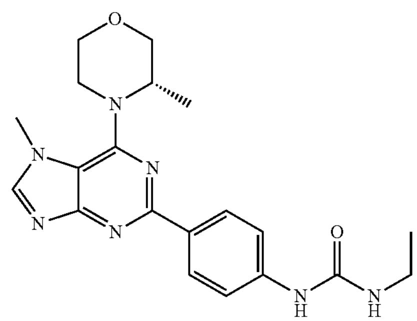 [SMILES: CCNC(=O)Nc1ccc(-c2nc(N3CCOC[C@@H]3C)c3c(ncn3C)n2)cc1] | (S)-1-ethyl-3-(4-(7-methyl-6-(3-methylmorpholino)-7H-purin-2-yl)phenyl)urea |
| 103 | 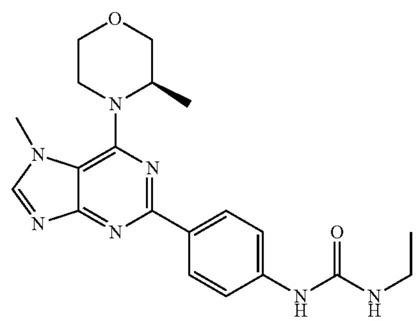 [SMILES: CCNC(=O)Nc1ccc(-c2nc(N3CCOC[C@H]3C)c3c(ncn3C)n2)cc1] | (R)-1-ethyl-3-(4-(7-methyl-6-(3-methylmorpholino)-7H-purin-2-yl)phenyl)urea |
| 104 | 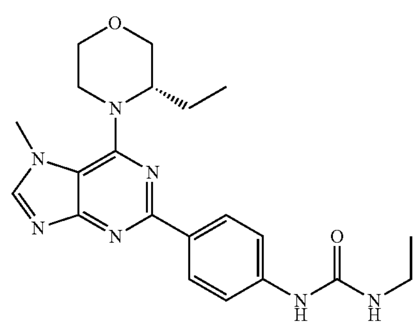 [SMILES: CCNC(=O)Nc1ccc(-c2nc(N3CCOC[C@@H]3CC)c3c(ncn3C)n2)cc1] | (S)-1-ethyl-3-(4-(6-(3-ethylmorpholino)-7-methyl-7H-purin-2-yl)phenyl)urea |
| 105 | 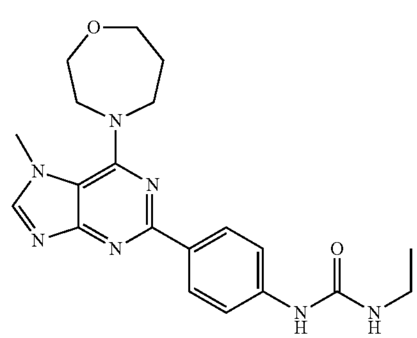 [SMILES: CCNC(=O)Nc1ccc(-c2nc(N3CCCOCC3)c3c(ncn3C)n2)cc1] | 1-ethyl-3-(4-(7-methyl-6-(1,4-oxazepan-4-yl)-7H-purin-2-yl)phenyl)urea |
| 106 | 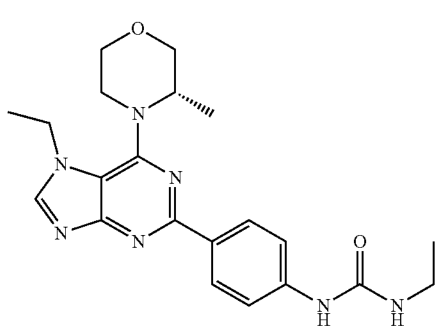 [SMILES: CCNC(=O)Nc1ccc(-c2nc(N3CCOC[C@@H]3C)c3c(ncn3CC)n2)cc1] | (S)-1-ethyl-3-(4-(7-ethyl-6-(3-methylmorpholino)-7H-purin-2-yl)phenyl)urea |

TABLE 1-continued
| No | Structure | Name |
|---|---|---|
| 107 | 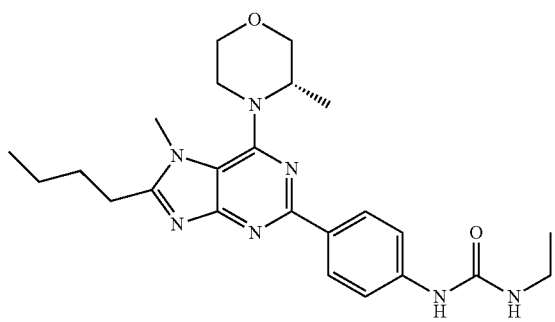 [SMILES: CCCCc1nc2nc(-c3ccc(NC(=O)NCC)cc3)nc(N3CCOC[C@@H]3C)c2n1C] | (S)-1-(4-(8-butyl-7-methyl-6-(3-methylmorpholino)-7H-purin-2-yl)phenyl)-3-ethylurea |
| 108 | 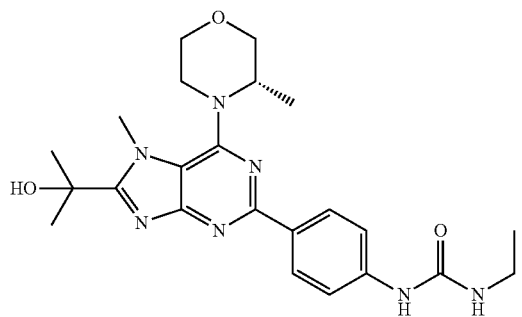 [SMILES: CCNC(=O)Nc1ccc(-c2nc(N3CCOC[C@@H]3C)c3c(n2)nc(C(C)(C)O)n3C)cc1] | (S)-1-ethyl-3-(4-(8-(2-hydroxypropan-2-yl)-7-methyl-6-(3-methylmorpholino)-7H-purin-2-yl)phenyl)urea |
| 109 | 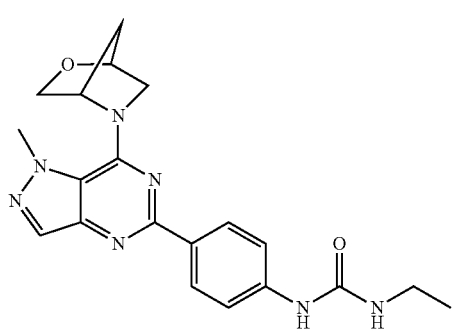 [SMILES: CCNC(=O)Nc1ccc(-c2nc(N3CC4CC3CO4)c3c(cnn3C)n2)cc1] | 1-(4-(7-((1S,4S)-2-oxa-5-azabicyclo[2.2.1]heptan-5-yl)-1-methyl-1H-pyrazolo[4,3-d]pyrimidin-5-yl)phenyl)-3-ethylurea |
| 110 | 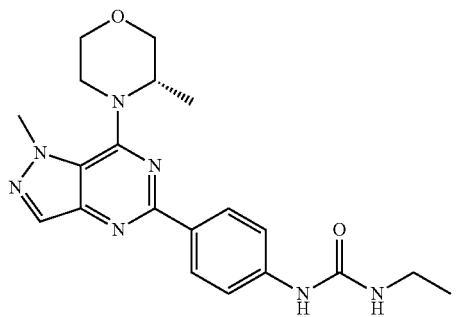 [SMILES: CCNC(=O)Nc1ccc(-c2nc(N3CCOC[C@@H]3C)c3c(cnn3C)n2)cc1] | (S)-1-ethyl-3-(4-(1-methyl-7-(3-methylmorpholino)-1H-pyrazolo[4,3-d]pyrimidin-5-yl)phenyl)urea |

TABLE 1-continued

| No | Structure | Name |
|---|---|---|
| 111 | 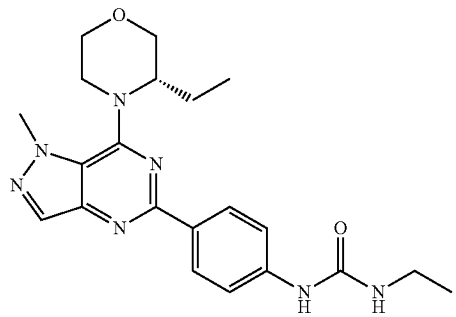 [SMILES: CCNC(=O)Nc1ccc(-c2nc(N3CCOC[C@@H]3CC)c3c(cnn3C)n2)cc1] | (S)-1-ethyl-3-(4-(7-(3-ethylmorpholino)-1-methyl-1H-pyrazolo[4,3-d]pyrimidin-5-yl)phenyl)urea |
| 112 | 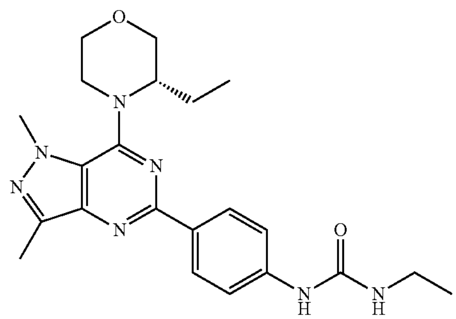 [SMILES: CCNC(=O)Nc1ccc(-c2nc(N3CCOC[C@@H]3CC)c3c(n2)c(C)nn3C)cc1] | (S)-1-ethyl-3-(4-(7-(3-ethylmorpholino)-1,3-dimethyl-1H-pyrazolo[4,3-d]pyrimidin-5-yl)phenyl)urea |
| 113 | 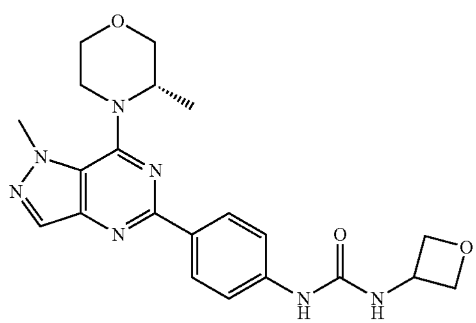 [SMILES: C[C@H]1COCCN1c1nc(-c2ccc(NC(=O)NC3COC3)cc2)nc2cnn(C)c12] | (S)-1-(4-(1-methyl-7-(3-methylmorpholino)-1H-pyrazolo[4,3-d]pyrimidin-5-yl)phenyl)-3-(oxetan-3-yl)urea |
| 114 | 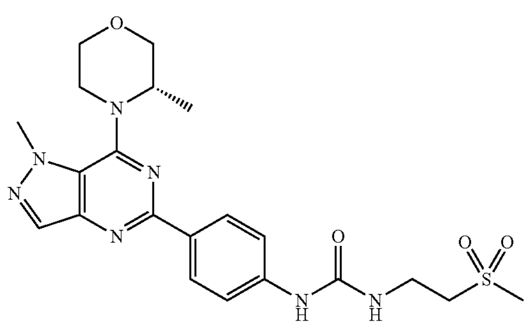 [SMILES: C[C@H]1COCCN1c1nc(-c2ccc(NC(=O)NCCS(C)(=O)=O)cc2)nc2cnn(C)c12] | (S)-1-(4-(1-methyl-7-(3-methylmorpholino)-1H-pyrazolo[4,3-d]pyrimidin-5-yl)phenyl)-3-(2-(methylsulfonyl)ethyl)urea |

I.B SYNTHESIS OF COMPOUNDS

As shown in the Examples section below, there are a variety of synthetic routes by which a skilled artisan can prepare compounds of the present invention and the related intermediates used to prepare such compounds. The following schemes illustrate some general methods for the preparation of compounds of the invention and key intermediates. Unless otherwise indicated, the abbreviations used in the Schemes below have the following meanings. R, R', R", R'"=at each occurrence is independently unsubstituted or substituted alkyl, alkenyl, alkynyl, heteroalkyl, cycloalkyl, heterocycloalkyl, aryl or heteroaryl, as protected as necessary to be a non-interfering group, LG=leaving group (e.g, halide, tosylate), Cyc=carbocycle or heterocycle, H(Ar)=aryl or heteroaryl ring, LDA=lithium diisopropylamide, THF=tetrahydrofuran, X=O, NP, $CH_2$, CHR, CRR, P=protecting group (e.g., BOC), and n=1 to 6.

Scheme 1 illustrates a general synthetic method for the synthesis of 2-chloropurine intermediates useful to prepare compounds of Formula I. The substitution of the N-7 nitrogen atom in dichloropurine (i), by for example, alkylation using R-LG, followed by displacement of the C-6 chloro group with a morpholino or another amino group, produces a C-6 amino substituted compound iii. Substitution at the C-8 position of the compound iii, by for example, first halogenating compound iii, yields intermediate compound iv. Subsequent palladium mediated cross-coupling (e.g., a Suzuki coupling) of compound iv with an aryl, heteroaryl. cycloalkyl or heterocycloalkyl boronate provides the C-8 substitution product intermediates (i.e., compound v-a, or v-b). Alternatively, deprotonation of compound iii using a strong base followed by the quenching the resultant anion with an electrophile such as a cyclic ketone produces other C-8 substitution product intermediates, e.g., compound vi. Conversion of hydroxy functional group of compound vi into a fluoro group (as in compound vii) can be accomplished using a fluorinating reagent such as Diethylaminosulfur trifluoride (DAST).

compound viii. This N-7 position can also be protected with other protecting group such as ones that are removed under basic or reductive conditions, such as toxylate. Other protecting groups suitable for protecting the N-7 position are described in P. G. M. Wuts and T. W. Greene, Greene's Protective Groups in Organic Synthesis 4$^{th}$ edition, Wiley-Interscience, New York, 2006. Displacement of the C-6 chloro group with a morpholino group, or another amino group, provides a C-6 amino substituted (e.g., morpholino substituted) product ix. Alkylation of the C-8 position by deprotonation of compound ix followed by quenching with an electrophile (e.g., a cyclic ketone) provides compound x. Palladium mediated cross-coupling (e.g., Suzuki coupling) of compound x with an aryl boronate reagent provides the ary-

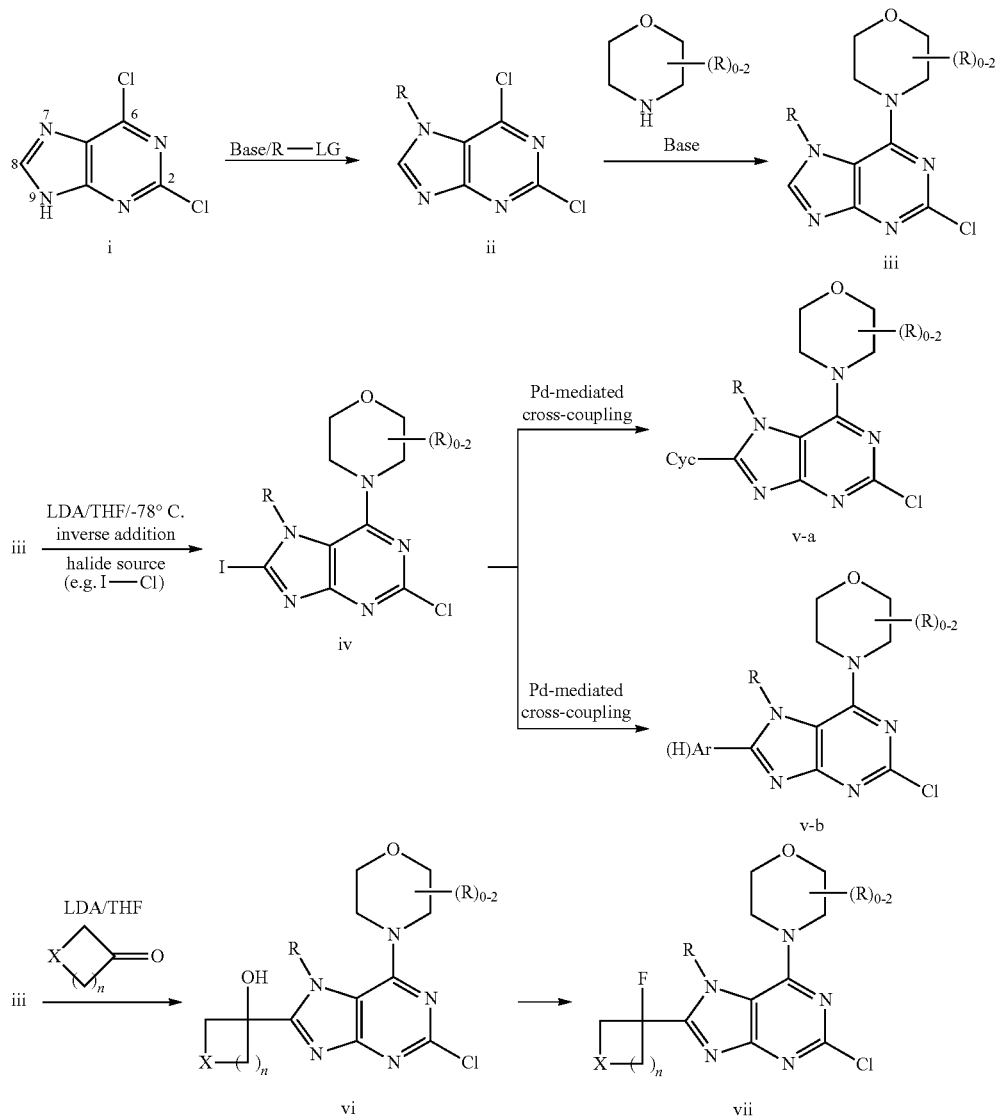

Scheme 2 illustrates a method of preparing intermediate compounds of the invention in which the order of substitution of N-7 position and C-8 position of the purine is reversed. First, the N-7 nitrogen atom of dichloropurine (i) is protected with a para-methoxybenzyl (PMB) protecting group to form lated product xi. Removal of the para-methoxy benzyl N-7 protecting group under oxidative conditions followed by substitution (e.g., alkylation using R-LG) of the resultant N-7 deprotected product xii produces compound xiii. Hydrogenation of the nitro group in compound xiii provides amino intermediate xiv which can be further elaborated into other compounds of Formula I using methods further described in the Examples section herein.

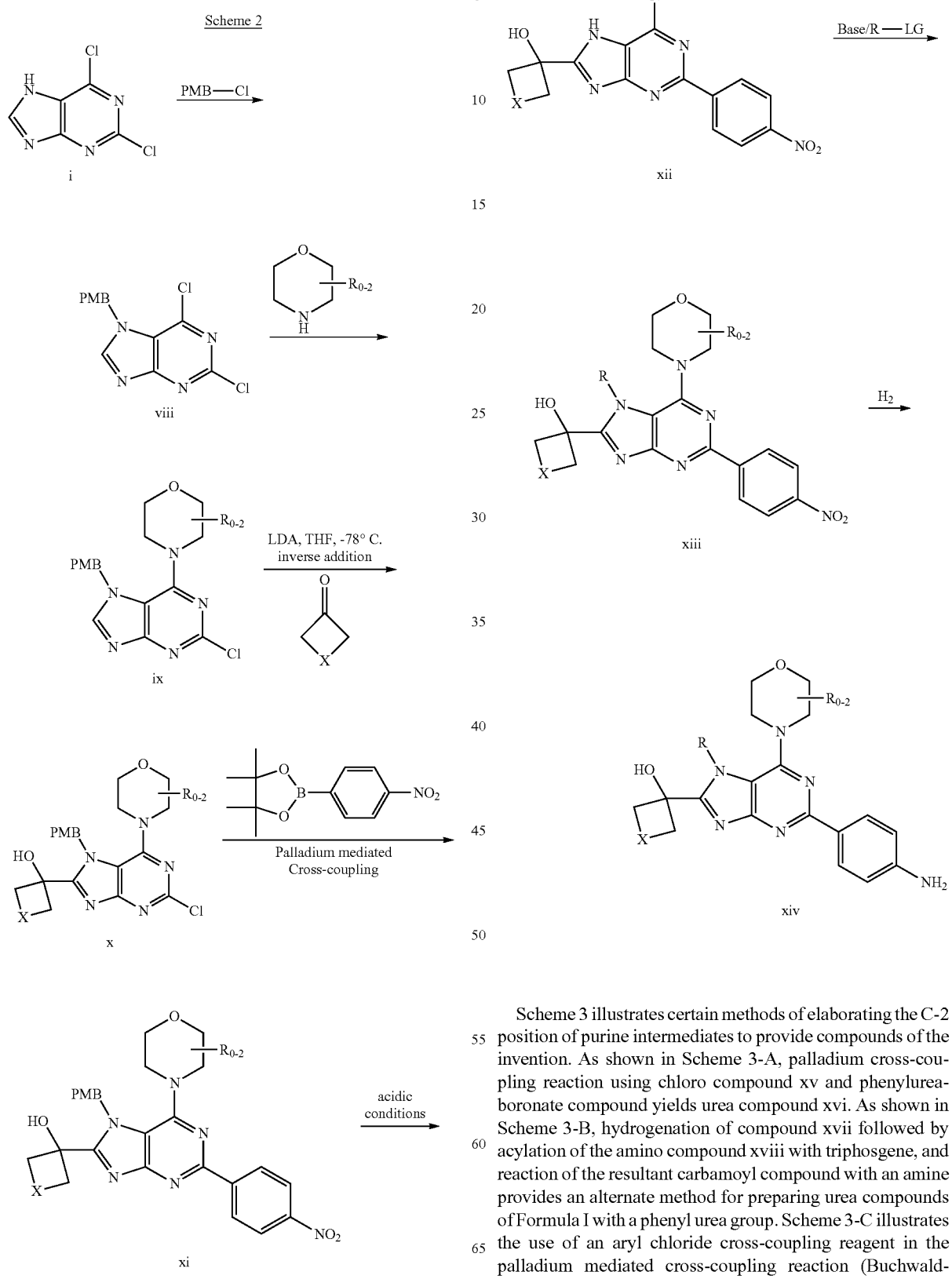

Scheme 3 illustrates certain methods of elaborating the C-2 position of purine intermediates to provide compounds of the invention. As shown in Scheme 3-A, palladium cross-coupling reaction using chloro compound xv and phenylurea-boronate compound yields urea compound xvi. As shown in Scheme 3-B, hydrogenation of compound xvii followed by acylation of the amino compound xviii with triphosgene, and reaction of the resultant carbamoyl compound with an amine provides an alternate method for preparing urea compounds of Formula I with a phenyl urea group. Scheme 3-C illustrates the use of an aryl chloride cross-coupling reagent in the palladium mediated cross-coupling reaction (Buchwald-Hartwig coupling) to prepare other compounds of Formula I.

Scheme 3
A:
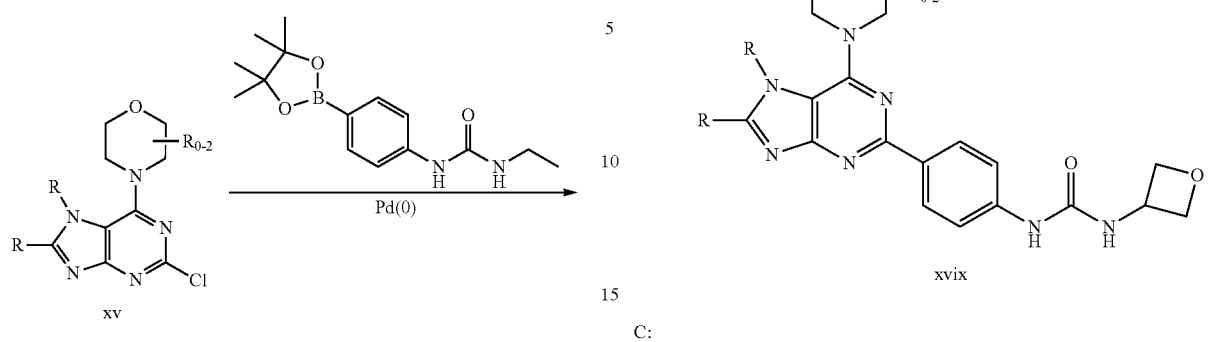
B:
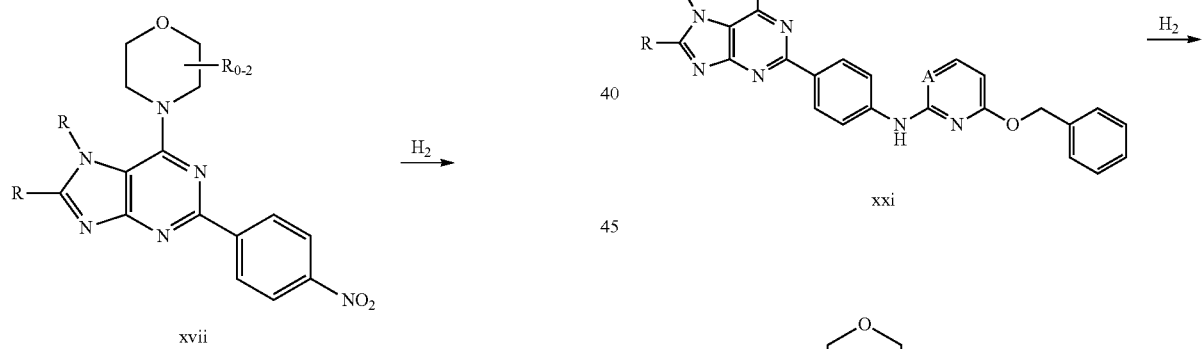
C:
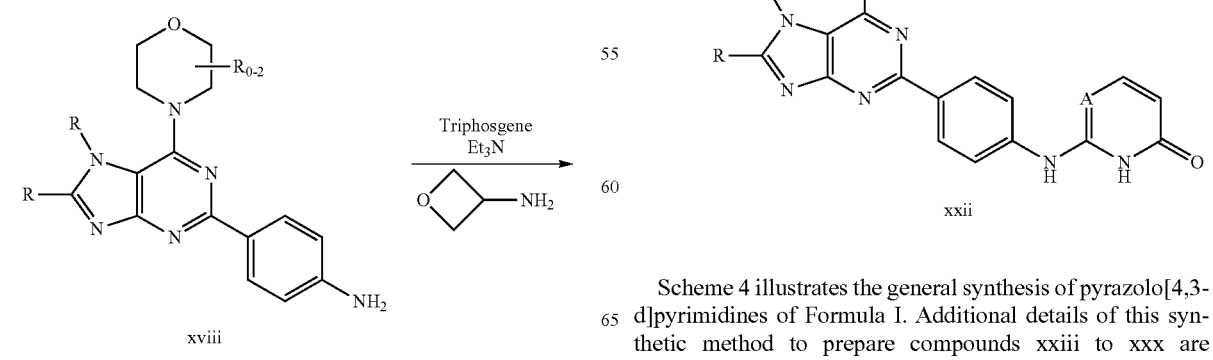
Scheme 4 illustrates the general synthesis of pyrazolo[4,3-d]pyrimidines of Formula I. Additional details of this synthetic method to prepare compounds xxiii to xxx are described in the Examples section.

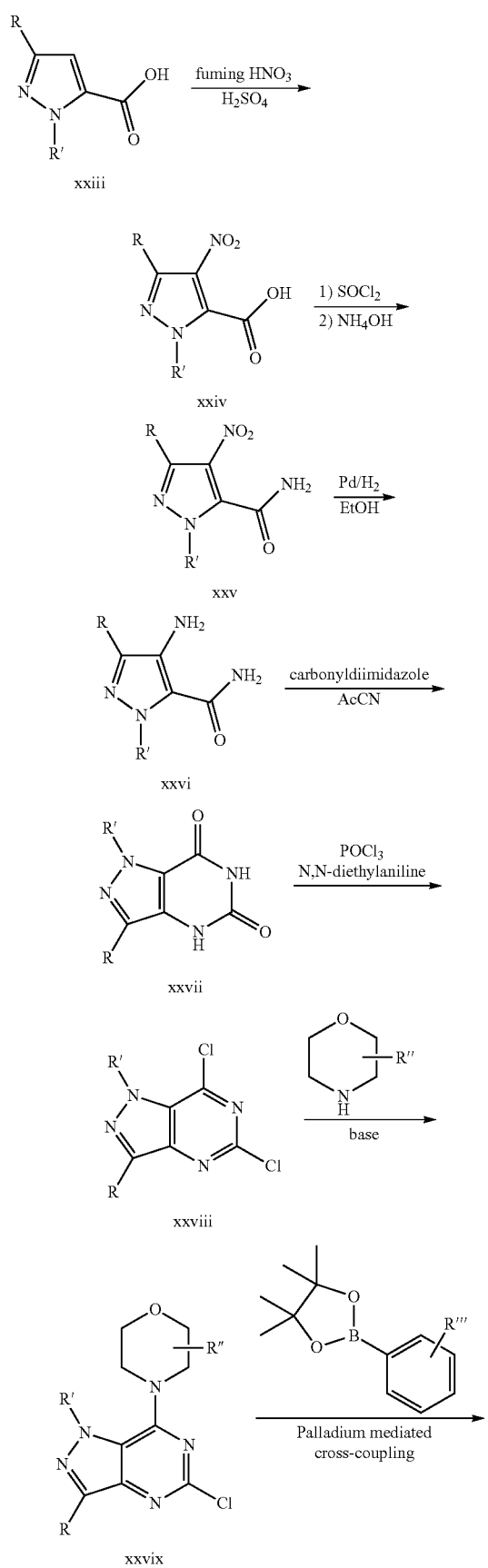

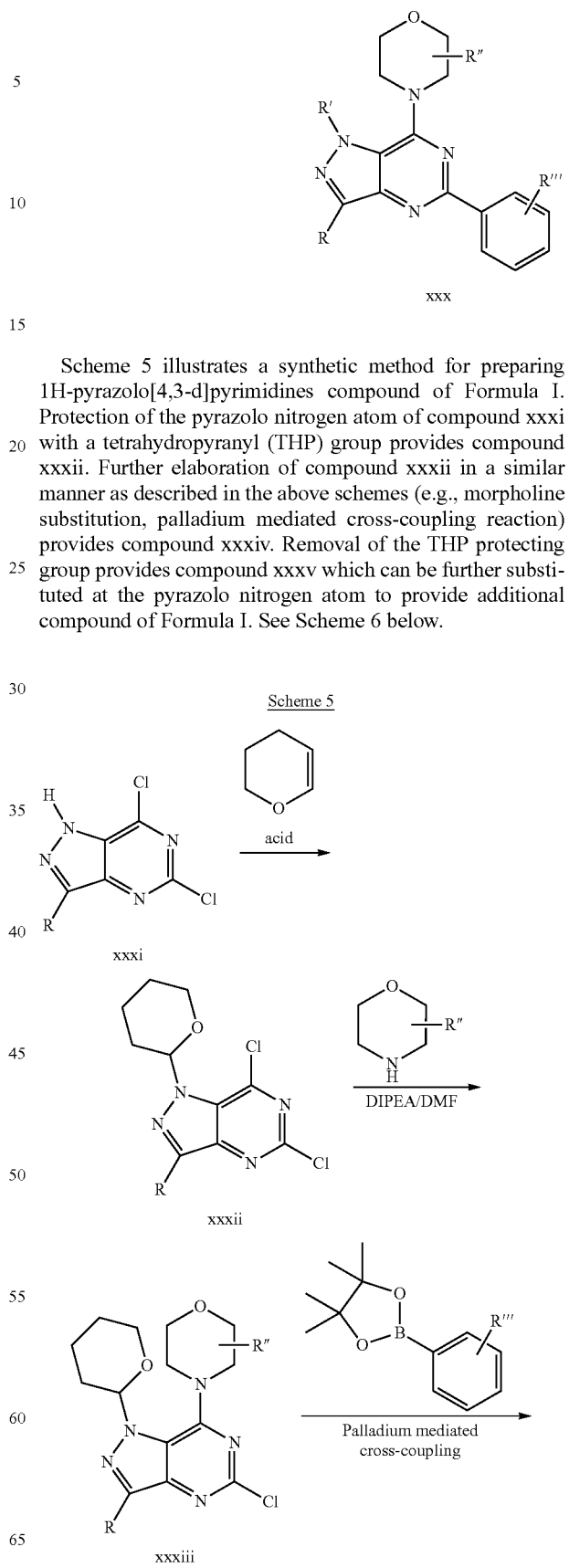

Scheme 5 illustrates a synthetic method for preparing 1H-pyrazolo[4,3-d]pyrimidines compound of Formula I. Protection of the pyrazolo nitrogen atom of compound xxxi with a tetrahydropyranyl (THP) group provides compound xxxii. Further elaboration of compound xxxii in a similar manner as described in the above schemes (e.g., morpholine substitution, palladium mediated cross-coupling reaction) provides compound xxxiv. Removal of the THP protecting group provides compound xxxv which can be further substituted at the pyrazolo nitrogen atom to provide additional compound of Formula I. See Scheme 6 below.

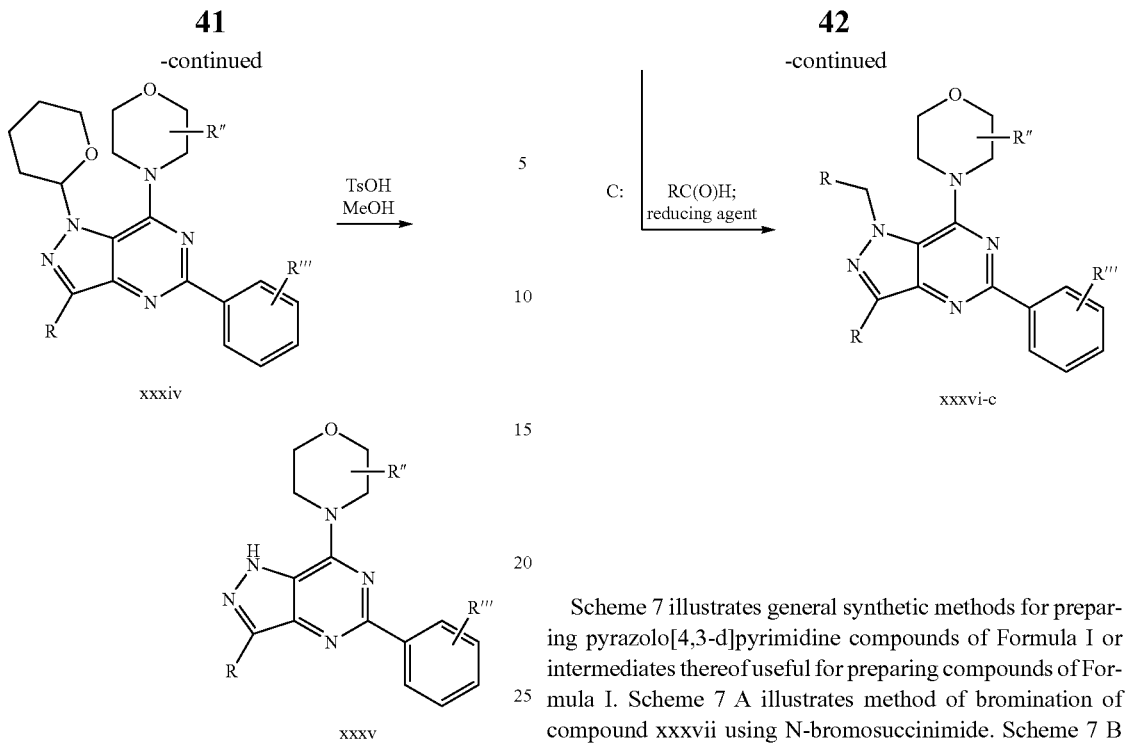

Scheme 6 illustrates some general synthetic method for substitution at the pyrazolo nitrogen atom in compounds of Formula I, for example, by alkylation (Scheme 6 A); acylation (Scheme 6 B); and reductive alkylation (Scheme 6 C).

Scheme 7 illustrates general synthetic methods for preparing pyrazolo[4,3-d]pyrimidine compounds of Formula I or intermediates thereof useful for preparing compounds of Formula I. Scheme 7 A illustrates method of bromination of compound xxxvii using N-bromosuccinimide. Scheme 7 B illustrates the reduction of ester xxxviii using a hydride reagent (LiBH$_4$) followed by toslylation of the reduction production to produce tosylate xxxviii-a. Scheme 7 C illustrates the reduction of ester xxxviii using diisobuylaluminum hydride to produce aldehyde xxxviii-b. Scheme 7 D illustrates amino acid coupling condition using N,N'-dicyclohexylcarbodiimide and hydroxybenzotriazole and an amine to form amide compound xxxvix-a.

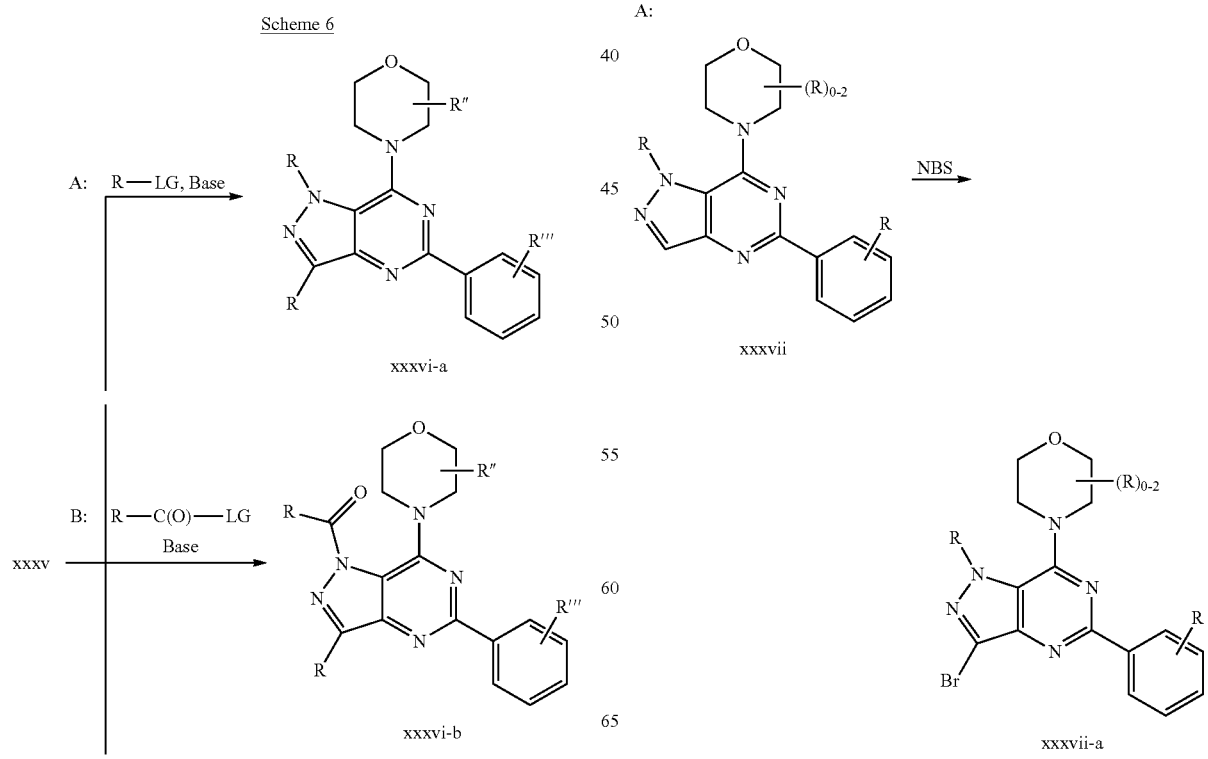

B:

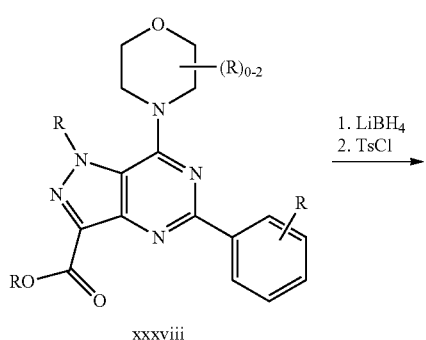

xxxviii

1. LiBH₄
2. TsCl
→

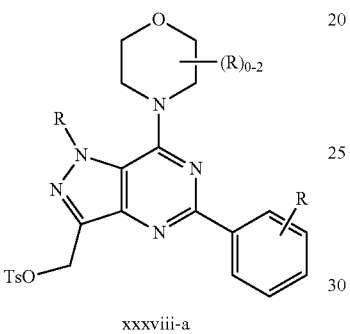

xxxviii-a

C:

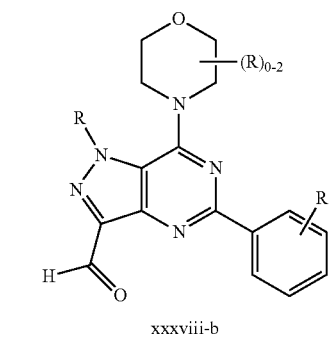

xxxviii

DIBAL →

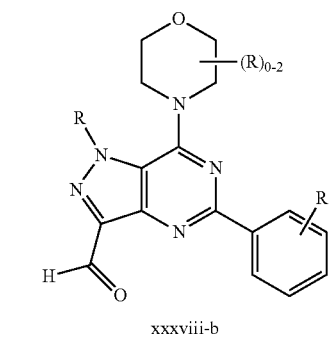

xxxviii-b

D:

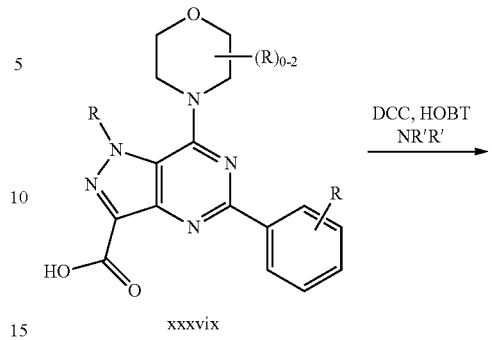

xxxvix

DCC, HOBT
NR'R'
→

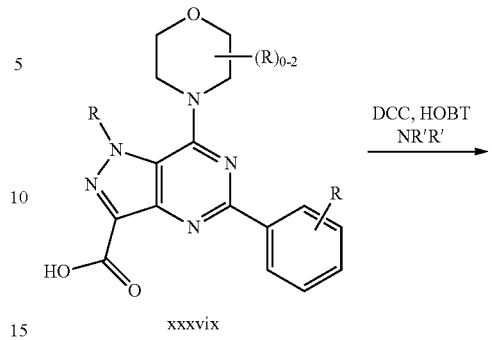

xxxvix-a

II. PHARMACEUTICAL COMPOSITIONS

In addition to one or more of the compounds provided above (or stereoisomers, geometric isomers, tautomers, solvates, metabolites or pharmaceutically acceptable salts, or prodrugs thereof), compositions for modulating mTOR activity in humans and animals will typically contain a pharmaceutically acceptable carrier, diluent or excipient.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent, carrier or excipient.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of a compound of the present invention can be prepared for various routes and types of administration. For example, a compound of the invention (e.g., a compound of Formula I) having the desired degree of purity can optionally be mixed with pharmaceutically acceptable diluents, carriers, excipients or stabilizers (see, Remington: The Science and Practice of Pharmacy: Remington the Science and Practice of Pharmacy (2005) $21^{st}$ Edition, Lippincott Williams & Wilkins, Philadelphia, Pa.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. Formulation in an acetate buffer at pH 5 is a suitable embodiment.

A compound of this invention (e.g., compound of Formula I) for use herein is preferably sterile. In particular, formulations to be used for in vivo administration must be sterile. Such sterilization is readily accomplished by filtration through sterile filtration membranes.

A compound of the invention ordinarily can be stored as a solid composition, a lyophilized formulation or as an aqueous solution.

A pharmaceutical composition of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of an inhibitor compound of the invention administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of Formula I) can be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773, 919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

A pharmaceutical composition of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient (e.g., compound of Formula I) as above defined together with a veterinary carrier therefore. Veterinary carriers are materials useful for the purpose of administering the composition and can be solid, liquid or gaseous materials which are otherwise inert or acceptable in the veterinary art and are compatible with the active ingredient. These veterinary compositions can be administered parenterally, orally or by any other desired route.

III. METHODS

In another aspect, the present invention provides for a compound of the invention (e.g., compound of Formula I), or a stereoisomer, geometric isomer, tautomer, solvate, metabolite, or pharmaceutically acceptable salt, prodrug thereof that inhibits the activity of mTOR kinase. In one embodiment, a compound of the invention (e.g., compound of Formula I), or a stereoisomer, geometric isomer, tautomer, solvate, metabolite, or pharmaceutically acceptable salt, prodrug thereof inhibits the activity of mTORC1 and mTORC2. In another embodiment, a compound of the invention (e.g., compound of Formula I), or a stereoisomer, geometric isomer, tautomer, solvate, metabolite, or pharmaceutically acceptable salt, prodrug thereof, inhibits the activity of mTORC 1. In another embodiment, a compound of the invention (e.g., compound of Formula I), or a stereoisomer, geometric isomer, tautomer, solvate, metabolite, or pharmaceutically acceptable salt, prodrug thereof, inhibits the activity of mTORC2. In certain embodiments, a compound of Formula I is 1×, 2×, 3×, 4×, 5×, 6×, 7×, 8×, 9×, 10×, 11×, 12×, 13×, 14×, 15×, 16×, 17×, 18×, 19×, 20×, 25×, 30×, 40×, 50×, 60×, 70×, 80×, 90×, 100×, 200×, 300×, 400×, 500×, 600×, 700×, 800×, 900× or 1000× more selective at inhibiting the activity of mTORC1 over mTORC2. In certain other embodiment, a compound of Formula I is 1×, 2×, 3×, 4×, 5×, 6×, 7×, 8×, 9×, 10×, 11×, 12×, 13×, 14×, 15×, 16×, 17×, 18×, 19×, 20×, 25×, 30×, 40×, 50×, 60×, 70×, 80×, 90×, 100×, 200×, 300×, 400×, 500×, 600×, 700×, 800×, 900× or 1000× more selective at inhibiting the activity of mTORC2 over mTORC 1. In certain embodiment, the compounds of the invention are more selective at inhibiting the activity of mTORC1 and/or mTORC2 over the related PI3 lipid kinases. In certain embodiments, a compound of Formula I is 1×, 2×, 3×, 4×, 5×, 6×, 7×, 8×, 9×, 10×, 11×, 12×, 13×, 14×, 15×, 16×, 17×, 18×, 19×, 20×, 25×, 30×, 40×, 50×, 60×, 70×, 80×, 90×, 100×, 200×, 300×, 400×, 500×, 600×, 700×, 800×, 900× or 1000× more selective at inhibiting the activity of and mTOR kinase (e.g., mTORC1, mTORC2) over a PI3K lipid kinase. In one aspect, compounds of the invention demonstrate surprisingly superior selectivity for the inhibition of mTOR kinase over related PI3 lipid kinases, e.g. PI3K-alpha. For example, a N-7 substituted purine compound, (S)-1-ethyl-3-(4-(7-methyl-6-(3-methylmorpholino)-7H-purin-2-yl)phenyl)urea, is 357× more selective for mTOR kinase over a related PI3 kinase (PI3K-alpha), the N-1 substituted pyrazolopyrimidine compound, (S)-1-ethyl-3-(4-(1-methyl-7-(3-methylmorpholino)-1H-pyrazolo[4,3-d]pyrimidin-5-yl)phenyl)urea, is 1250× selective for mTOR kinase over the related PI3 kinase (PI3K-alpha), and whereas the isomeric compound (S)-1-ethyl-3-(4-(9-methyl-6-(3-methylmorpholino)-9H-purin-2-yl)phenyl)urea is 29× more selective for mTOR kinase over a related PI3 kinase (PI3K-alpha). The N-7 substituted purine compound, (S)-1-ethyl-3-(4-(7-ethyl-6-(3-methylmorpholino)-7H-purin-2-yl)phenyl) urea, is 250× more selective for mTOR kinase over a related PI3 kinase (PI3K-alpha), whereas the isomeric compound (S)-1-ethyl-3-(4-(9-ethyl-6-(3-methylmorpholino)-9H-purin-2-yl)phenyl)urea is 45× more selective for mTOR kinase over the related PI3 kinase (PI3K-alpha).

In each of the above embodiment, in one particular aspect, a compound of the invention (e.g., compound of Formula I), or stereoisomer, geometric isomer, tautomer, solvate, metabolite, or pharmaceutically acceptable salt, or prodrug thereof, is formulated as a pharmaceutical composition.

The present invention further provides for a method of inhibiting the activity of mTOR kinase in a cell, comprising contacting said cell with an effective amount of an active compound of the invention (e.g., compound of Formula I), or a stereoisomer, geometric isomer, tautomer, solvate, metabolite, or pharmaceutically acceptable salt or prodrug thereof. The present invention further provides for a method of inhibiting cell proliferation comprising contacting the cell with a compound of Formula I or a subgenus thereof. Such methods can be practiced in vitro or in vivo.

A compound of the present invention, or stereoisomer, geometric isomer, tautomer, solvate, metabolite, or pharmaceutically acceptable salt, prodrug thereof, is useful for treating diseases, conditions and/or disorders including, but not limited to, those characterized by over expression of PIKK kinases, e.g. mTOR kinase. Accordingly, another aspect of this invention includes methods of treating diseases or conditions that can be treated by inhibiting mTOR kinase. In one embodiment, the method comprises administering to a mammal in need thereof a therapeutically effective amount of a compound of the invention (e.g., compound of Formula I), or a stereoisomer, geometric isomer, tautomer, solvate, metabolite, or pharmaceutically acceptable salt or prodrug thereof. In the above embodiment, in one particular aspect, a compound of the invention (e.g., compound of Formula I), or stereoisomer, geometric isomer, tautomer, solvate, metabolite, or pharmaceutically acceptable salt, prodrug thereof, is formulated as a pharmaceutical composition.

The compounds of the invention can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

A dose to treat mammal (e.g., human) can range from about 10 mg to about 1000 mg of a Formula I compound. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. In addition, toxicity factors can influence the dosage and administration regimen. When administered orally, the pill, capsule, or tablet can be ingested daily or less frequently for a specified period of time. The regimen can be repeated for a number of cycles of therapy.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, Peutz-Jegher syndrome, Tuberous Sclerosis, pathologic immune conditions involving T cell activation, CNS disorders in a patient, and aging. In one embodiment, a human patient is treated with a compound of a compound of the invention (e.g., compound of Formula I) and a pharmaceutically acceptable carrier, adjuvant, or vehicle, wherein a compound of the invention is present in an amount to detectably inhibit mTOR kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In certain embodiment, compounds of the invention are useful for the treatment of cancer selected from the group consisting of breast, NSCLC, small cell carcinoma, liver carcinoma, lymphoid disorders, sarcoma, colon-rectum, rectum and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of the invention, or stereoisomer, geometric isomer, tautomer, solvate, metabolite, or pharmaceutically acceptable salt, or prodrug thereof, in the treatment of the diseases or conditions described herein in a mammal, for example, a human, suffering from such disease or condition. Also provided is the use of a compound of this invention, or stereoisomer, geometric isomer, tautomer, solvate, metabolite, or pharmaceutically acceptable salt, or prodrug thereof, in the preparation of a medicament for the treatment of the diseases and conditions described herein in a mammal, for example a human, suffering from such disorder.

In one embodiment, a compound of the invention (e.g., compound of Formula I), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer. Such chemotherapy can include, but are not limited to one or more of the chemotherapeutic agents described herein.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other chemotherapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

IV. EXAMPLES

These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other mTOR inhibitors of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography-Mass Spectrometry (LCMS) experiments to determine retention times ($R_T$) and associated mass ions were performed using one of the following methods. Method A: Experiments performed on a PE Sciex API 150 EX quadrupole mass spectrometer linked to a Shimadzu LC-10AD LC system with diode array detector and 225 position autosampler using a Kromasil C18 50×4.6 mm column and a 3 ml/minute flow rate. The solvent system was a gradient starting with 100% water with 0.05% TFA (solvent A) and 0% acetonitrile with 0.0375% TFA (solvent B), ramping up to 10% solvent A and 90% solvent B over 4 minutes. The final solvent system was held constant for a further 0.50 minutes. Method B: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 1.5 ml/minute flow rate. Method B1: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 1.5 minutes. The final solvent system was held constant for a further 1 minute. Method B2: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 3.0 minutes. The final solvent system was held constant for a further 1 minute. Method C: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 0.6 ml/minute flow rate. The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 9.0 minutes. The final solvent system was held constant for a further 1 minute. The products formed in the reaction mixtures can be purified by reverse phase high pressure liquid chromatography (RP-HPLC) using the following conditions: Reverse phase HPLC was conducted on Gemini-NX column (100×30 mm, 10 micron); 5-85% ACN over 10 min. gradient either 0.1% FA or 0.1% NH$_4$OH at 60 ml/min, 254 nm, or on Zymor Pegasus column (150×21.2 mm, 5 micron); 5-60% Methanol at 70 ml/min, 254 nm.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

Example 1

Synthesis of 2,6-dichloro-7-methyl-7H-purine from 3,7 dimethyl-1H-purine 2,6(3H,7H)dione (theobromine) (a-2)

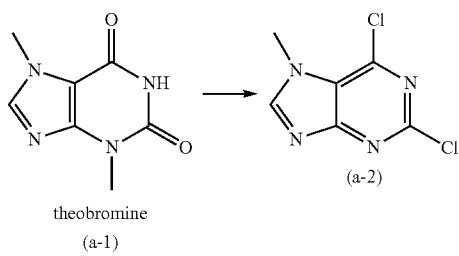

theobromine
(a-1)

2,6 dichloro-7-methyl-7H-purine was prepared from theobromine (a-1) in 10% yield following the procedure of Uretskaya, G. Ya., Rybinka, E. I., and Men'shikov, G. P. *Zh. Obshch. Ki.*, 1960, 30, 327 with the modification of N,N, diethylaniline disclosed by Stanovik, B. et at in the *Australian Journal of Chemistry*, 1981, 34, 1729. 1H NMR was identical in all respects to the material prepared by alkylation of commercially available 2,6 dichloropurine with base and iodomethane. For example, the procedure reported by Feng et al. (WO2004/087053) utilizes 60% NaH as base, dimethylformamide (DMF) as the solvent and iodomethane yielded a 1:1 mixture of the N-7/N-9 methylated products which were separated via silica chromatography. The procedure reported by Lewi et et al (WO2005/028479 A2) utilizes potassium carbonate as the base, acetonitrile as solvent (rt 70 h) and iodomethane and yielded a 2:1 isolated yield of methylated purines after silica chromatography (60% yield N9Me/30% yield N-7 Methylated). Similarly acetone can replace acetonitrile as the solvent and after refluxing with potassium carbonate and iodomethane for 24 h a 3:1 mixture of N9/N7 is obtained. The N-7 methylated product was isolated in 16.3% purified yield after silica chromatography. A report by Chi-Huey Wong et al. (see, Bioorg & Med Chem 13 (2005) 4622-4626) utilizes tetrabutylammonium fluoride as the base (1M solution THF) and iodomethane to give similarity a 3:1 ratio of the N-9/N-7 methylated purines which could be separated by silica chromatography. $^1$H NMR (400 MHz, DMSO d$_6$) 8.79 (s, 1H, H8), 4.06 (s, 3H, N7Me).

Example 2

Synthesis of 1-ethyl-3-(4-(7-methyl-6-morpholino-7H-purin-2-yl)phenyl)urea (b-2)

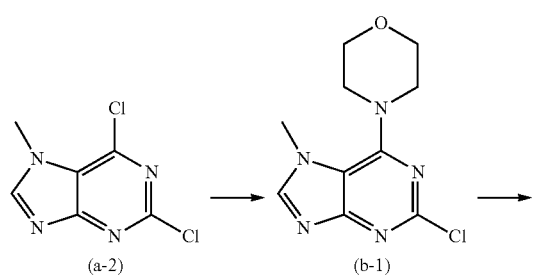

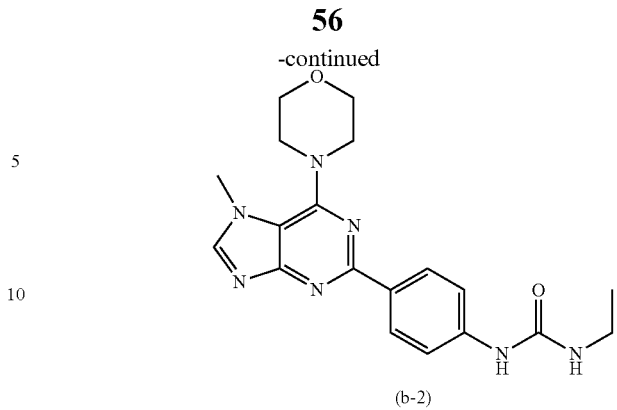

Preparation of 4-(2-chloro-7-methyl-7H-purin-6-yl)morpholine (b-1): An oven-dried 15 mL pressure tube equipped with a stir bar and septa was cooled under nitrogen, charged with 123.1 mg (0.61 mmol) of 2,6 dichloro-7-methyl-7H-purine and dissolved in anhydrous ethanol/DMF (0.5 mL/0.3 mL, 0.76M). N,N diisopropylethylamine (0.130 mL, 0.73 mmol) was added via syringe followed by morpholine (0.064 mL, 0.73 mmol). The pressure tube was flushed with nitrogen and the septa replaced by a Teflon screw cap. The reaction mixture stirred overnight at room temperature. LCMS (Method A) indicated complete consumption of a and one major uv active product (ret. time 1.17 min) which exhibited the correct M+H$^+$ for (b). Thin layer chromatograph (TLC) analysis in 20% MeOH/EA confirms one major uv active product. The reaction mixture was poured into a flask containing 30 mL of 50/50 Et$_2$O/EA and the pressure tube rinsed with 2×10 mL of 50/50 Et$_2$O/EA, then 10 mL EA. Transferred to a separatory funnel and washed 1× with 50% brine and 1× with brine. Re-extracted the combined aqueous layers additionally with 50/50 Et$_2$O/EA (diethyl ether:ethyl acetate) (2×20 mL), combined organic extracts, dried (MgSO$_4$), filtered, concentrated and dried under high vacuum to yield 119.3 mg of crude product (77.6%) which was taken directly into the next step. $^1$H NMR (400 MHz, DMSO d$_6$) 8.44 (s, 1H), 3.96 (s, 3H), 3.80-3.71 (m, 4H), 3.53-3.44 (m, 4H). LC/MS-m/z+254.5 (M+H)+.

Preparation of title compound (b-2): Nitrogen was bubbled through the water and acetonitrile overnight to degass. A 2-5 mL conical microwave tube was charged with 84 mg (0.29 mmol) of the [(4-Ethylureido)phenyl]boronic acid, pinacol ester, 17 mg (0.015 mmol) of tetrakis(triphenylphosphine) palladium(0), 39 mg (0.37 mmol) of sodium carbonate, and 40 mg (0.4 mmol) of potassium acetate. 56.8 mg (0.224 mmol) of 4-(2-chloro-7-methyl-7H-purin-6-yl)morpholine was added, followed by a stir bar and the mixture dissolved in ACN (3.0 mL)/water (0.9 mL). The microwave vial was capped and microwaved (300 watts, 130° C. 15 min). After cooling LCMS (Method A) analysis indicated complete consumption of b to give a major uv active product (ret. time 1.30 min) which exhibited correct M+H$^+$ for the urea along with triphenylphosphine as a by product (ret. time 2.24 min). The reaction mixture was diluted into 30 mL of EA and the tube rinsed with additional EA. The EA was transferred to a 125 mL separatory funnel, washed 1× with water, 1× with brine, dried (MgSO$_4$), filtered and concentrated to give 96.4 mg of crude which was purified by RP HPLC to afford 32.5 mg (38%) which was analyzed for identity and purity via LCMS (Method C). $^1$H NMR (500 MHz, DMSO d$_6$) 8.64 (s, 1H), 8.38 (s, 1H), 8.25 (d, J=8.7 Hz, 2H), 7.49 (d, J=8.7 Hz, 2H), 6.18 (t, J=5.5 Hz, 1H), 3.99 (s, 3H), 3.87-3.77 (m, 4H), 3.53-3.45 (m, 4H), 3.19-3.06 (m, 2H), 1.06 (t, J=7.2 Hz, 3H). LC/MS-m/z+382.1 (M+H)+.

Example 3

Synthesis of (S)-1-ethyl-3-(4-(7-methyl-6-(3-methyl-morpholino)-7H-purin-2-yl)phenyl)urea (c-2)

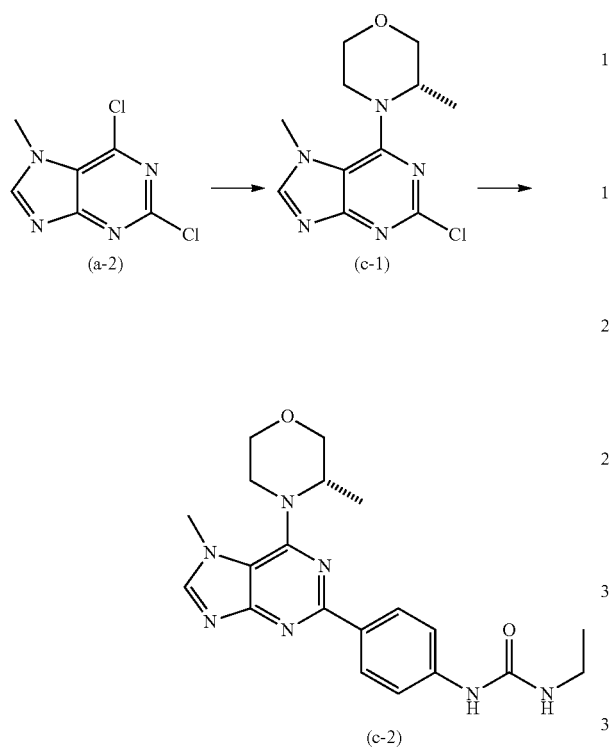

Preparation of (S)-4-(2-chloro-7-methyl-7H-purin-6-yl)-3-methylmorpholine (c-1): Compound (c-1) was prepared as described for Example 2 with the modification that (S)-3-methylmorpholine was used in place of morpholine and 1.0 mL/0.6 mL of ethanol/DMF plus gentle heating was necessary to effect dissolution of (a-2). Once solubilized, the reaction mixture remained homogeneous upon cooling to room temperature. Diisopropylethylamine (DIPEA) and (S)-3-methylmorpholine were added at room temperature. The intermediate compound (c-1) was obtained as a white foam in 85% yield after workup and was taken directly into the next step. $^1$H NMR (400 MHz, DMSO d$_6$) 8.44 (s, 1H), 4.04 (dd, J=6.7, 3.3 Hz, 1H), 3.96 (s, 3H), 3.84 (dt, J=10.8, 2.8 Hz, 1H), 3.76 (dd, J=11.3, 2.8 Hz, 1H), 3.68-3.49 (m, 3H), 3.40-3.37 (m, 1H), 1.20 (d, J=6.6 Hz, 3H). LC/MS-m/z+268.1 (M+H)+.

Preparation of title compound (c-2): (S)-1-ethyl-3-(4-(7-methyl-6-(3-methylmorpholino)-7H-purin-2-yl)phenyl)urea was prepared as described for Example 2 and purified by RP HPLC to afford 37.2 mg (48%) which was analyzed for identity and purity via LCMS (Method C). $^1$H NMR (500 MHz, DMSO d$_6$) 8.67 (s, 1H), 8.39 (s, 1H), 8.25 (d, J=8.8 Hz, 2H), 7.50 (d, J=8.8 Hz, 2H), 6.21 (t, J=5.6 Hz, 1H), 3.99 (s, 4H), 3.94-3.81 (m, 2H), 3.75 (t, J=8.4 Hz, 1H), 3.62-3.47 (m, 3H), 3.20-3.0 (m, 2H), 1.19 (d, J=6.4 Hz, 3H), 1.06 (t, J=7.2 Hz, 3H). LC/MS-m/z+396.2 (M+H)+.

Example 4

Synthesis of (R)-1-ethyl-3-(4-(7-methyl-6-(3-methylmorpholino)-7H-purin-2-yl)phenyl)urea (d-2)

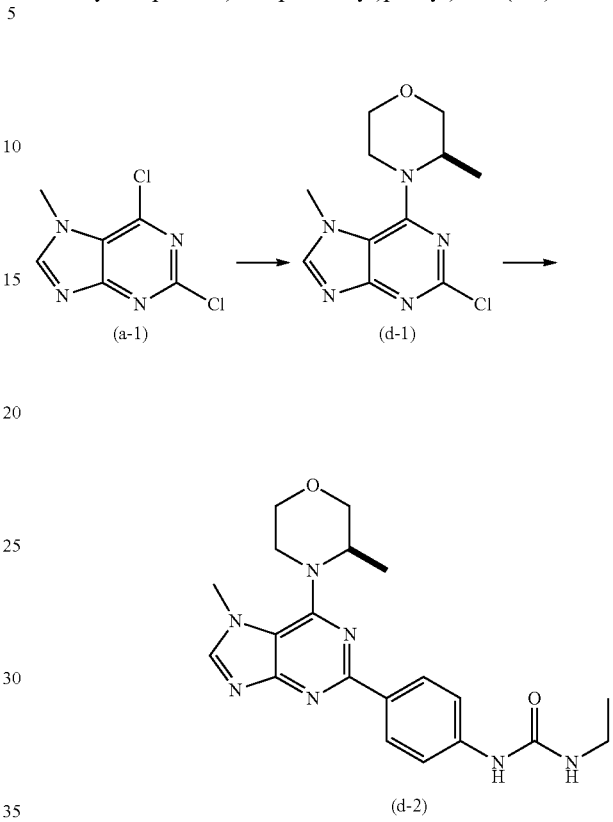

Preparation of (R)-4-(2-chloro-7-methyl-7H-purin-6-yl)-3-methylmorpholine (d-1) was prepared as described in Example 2 with the modification that (R)-3-methylmorpholine was used in place of morpholine and 2.0 mL/0.75 mL of ethanol/DMF plus gentle heating was necessary to effect dissolution of (a-1). Once solubilized, the reaction mixture remained homogeneous upon cooling to room temperature. Diisopropylamine and (R)-3-methylmorpholine were added at room temperature and the reaction heated to 50° C. for 36 h. The intermediate compound (d-1) was obtained as a waxy tan solid in 68% yield after workup and was taken directly into the next step. $^1$H NMR (400 MHz, DMSO d$_6$) 8.44 (s, 1H), 4.04 (dd, J=6.7, 3.3 Hz, 1H), 3.96 (s, 3H), 3.84 (dt, J=10.8, 2.8 Hz, 1H), 3.76 (dd, J=11.3, 2.8 Hz, 1H), 3.68-3.49 (m, 3H), 3.40-3.37 (m, 1H), 1.20 (d, J=6.6 Hz, 3H). LC/MS-m/z+268.1 (M+H)+.

Preparation of title compound (d-2): (R)-1-ethyl-3-(4-(7-methyl-6-(3-methylmorpholino)-7H-purin-2-yl)phenyl)urea (d-2) was prepared as described for Example 2 and purified by RP HPLC to afford 23.5 mg (32%) which was analyzed for identity and purity via LCMS (Method C). $^1$H NMR (500 MHz, DMSO d$_6$) 8.67 (s, 1H), 8.39 (s, 1H), 8.25 (d, J=8.8 Hz, 2H), 7.50 (d, J=8.8 Hz, 2H), 6.21 (t, J=5.6 Hz, 1H), 3.99 (s, 4H), 3.94-3.81 (m, 2H), 3.75 (t, J=8.4 Hz, 1H), 3.62-3.47 (m, 3H), 3.20-3.0 (m, 2H), 1.19 (d, J=6.4 Hz, 3H), 1.06 (t, J=7.2 Hz, 3H). LC/MS-m/z+396.2 (M+H)+.

Example 5

Synthesis of (S)-1-ethyl-3-(4-(6-(3-ethylmorpholino)-7-methyl-7H-purin-2-yl)phenyl)urea (e-2)

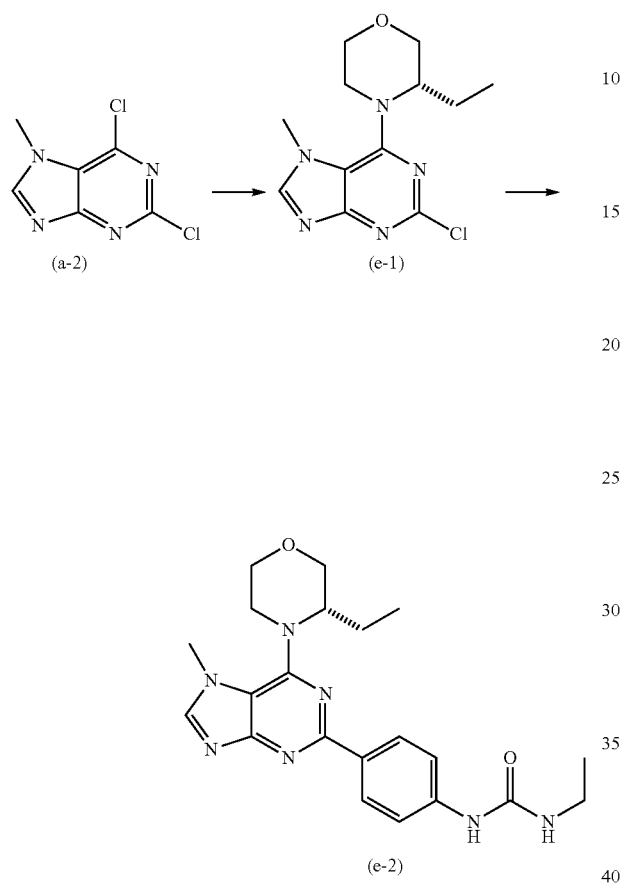

Preparation of (S)-4-(2-chloro-7-methyl-7H-purin-6-yl)-3-ethylmorpholine (e-1) was prepared as described in Example 2 with the modification that (S)-3-ethylmorpholine HCl salt was used in place of morpholine and the 3.5/1 mixture of ethanol/DMF required gentle heating was necessary to effect dissolution of (a-2). Once solubilized, the reaction mixture remained homogeneous upon cooling to room temperature. Diisopropylethylamine and (S)-3-ethylmorpholine HCl were added at room temperature and the reaction stirred for 20 h. Additional heating to 60° C. for 24 h was required for complete conversion to (e-1). The intermediate compound (e-1) was obtained as a tan solid in 87% yield after workup and was taken directly into the next step. $^1$H NMR (400 MHz, DMSO d$_6$) 8.43 (s, 1H), 4.03 (m, 1H), 3.94 (s, 3H), 3.78 (m, 3H), 3.62 (m, 1H), 3.52 (dd, J=7.3, 18.4 Hz, 2H), 1.79 (m, 2H), 0.79 (t, J=7.4 Hz, 3H). LC/MS-m/z+282.5 (M+H)+.

Preparation of title compound (e-2): (S)-1-ethyl-3-(4-(7-methyl-6-(3-methylmorpholino)-7H-purin-2-yl)phenyl)urea (e-2) was prepared as described for Example 2 and purified by RP HPLC to afford 136.5 mg (56%) which was analyzed for identity and purity via LCMS (Method C). $^1$H NMR (400 MHz, DMSO d$_6$) 8.61 (s, 1H), 8.36 (s, 1H), 8.24 (d, J=8.7 Hz, 2H), 7.49 (d, J=8.7 Hz, 2H), 6.17 (t, J=5.4 Hz, 1H), 3.97 (s+m, 4H), 3.83 (dtd, J=14.1, 11.4, 2.8 Hz, 4H), 3.63 (d, J=9 Hz, 2H), 3.45 (m, 1H), 3.14 (dd, J=14.1, 7.1 Hz, 2H), 1.79 (p, J=7.4 Hz, 2H), 1.07 (t, J=7.2 Hz, 3H), 0.83 (t, J=7.4 Hz, 3H). LC/MS-m/z+410.2 (M+H)+.

Example 6

Preparation of 1-ethyl-3-(4-(7-methyl-6-(1,4-oxazepan-4-yl)-7H-purin-2-yl)phenyl)urea (f-2)

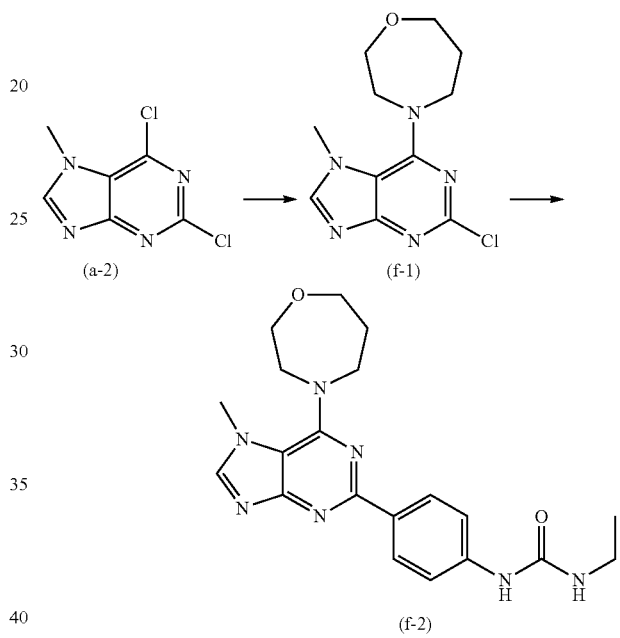

Preparation of 4-(2-chloro-7-methyl-7H-purin-6-yl)-1,4-oxazepane: Compound (f-1) was prepared as described in Example 2 with the modification that 1,4 oxazepane was used in place of morpholine and the 3/1 mixture of ethanol/DMF required gentle heating was necessary to effect dissolution of a. The reaction mixture was stirred at room temperature for 72 hours and worked up as described in Example 2. The crude product was further purified by silica chromatography (ISCO, 0-30% MeOH/EA) to give (f-1) in 40% purified yield. $^1$H NMR (400 MHz, CDCl$_3$) δ 7.86 (s, 1H), 3.96 (s, 3H), 3.92-3.87 (m, 2H), 3.86-3.78 (m, 6H), 2.15-2.05 (m, 2H). LC/MS-m/z+268.3 (M+H)+.

Preparation of title compound (f-2): The title compound was prepared as described for Example 2 and purified by RP HPLC to afford 7.5 mg (13%) which was analyzed for identity and purity via LCMS (Method C). $^1$H NMR (400 MHz, DMSO d$_6$) 8.58 (s, 1H), 8.29 (s, 1H), 8.23 (d, J=8.7 Hz, 2H), 7.47 (d, J=8.7 Hz, 2H), 6.15 (t, J=5.5 Hz, 1H), 3.98 (s, 3H), 3.87 (m, 6H), 3.74 (t, J=5.5 Hz, 2H), 3.19-3.06 (m, 2H), 2.25-1.97 (m, 2H), 1.07 (t, J=7.2 Hz, 3H). LC/MS-m/z+396.2 (M+H)+.

Example 7

Preparation of (S)-1-ethyl-3-(4-(7-ethyl-6-(3-methyl-morpholino)-7H-purin-2-yl)phenyl)urea (g-3)

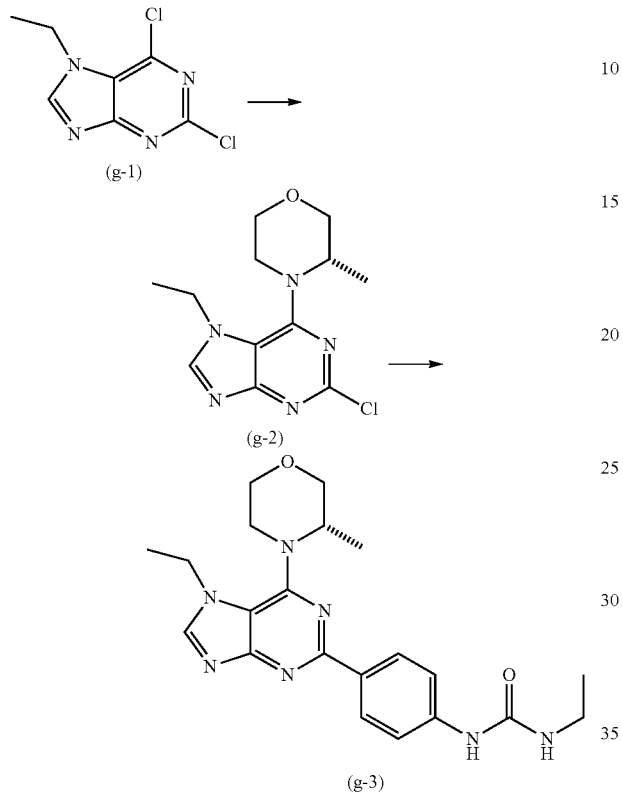

Preparation of 2,6-dichloro-7-ethyl-7H-purine (g-1): Compound (g-1) was prepared using the procedure described by Chi-Huey Wong et al. Bioorg. & Med. Chem. 13 (2005) 4622-4626 utilized tetrabutylammonium fluoride as the base (1M sol'n in THF) and iodoethane to give 2,6-dichloro-7-ethyl-7H-purine in 6.5% yield after workup and separation of the regioisomers on silica (ISCO, 10-100% EA/hexane). $^1$H NMR (500 MHz, DMSO d$_6$) 8.91 (s, 1H), 4.49 (q, J=7.2 Hz, 2H), 1.46 (t, J=7.2 Hz, 3H). LC/MS-m/z+217.2 (M+H)+.

Preparation of (S)-4-(2-chloro-7-ethyl-7H-purin-6-yl)-3-methylmorpholine (g-2): Compound (g-2) was prepared as described for Example 2 with the modification that (S)-3-methylmorpholine was used in place of morpholine. The reaction mixture was stirred at room temperature for 72 h and workup as described in Example 2 to provide (g-2) in 74% yield. The crude material was used without further purification. $^1$H NMR (400 MHz, DMSO d$_6$) 8.60 (s, 1H), 4.31 (m, 2H), 3.93 (m, 1H), 3.81 (m, 2H), 3.65 (t, J=9.0 Hz, 1H), 3.53 (m, 2H), 3.29 (m, 1H), 1.39 (t, J=7.2 Hz, 3H), 1.17 (d, J=6.5 Hz, 3H). LC/MS-m/z+282.3 (M+H)+.

Preparation of (S)-1-ethyl-3-(4-(7-ethyl-6-(3-methylmorpholino)-7H-purin-2-yl)phenyl)urea (g-3): (S)-1-ethyl-3-(4-(7-ethyl-6-(3-methylmorpholino)-7H-purin-2-yl)phenyl)urea was prepared as described for Example 2 and purified by RP HPLC to afford 61.6 mg (77.4%) which was analyzed for identity and purity via LCMS (Method C). $^1$H NMR (500 MHz, DMSO d$_6$) 8.65 (s, 1H), 8.54 (s, 1H), 8.27 (d, J=8.8 Hz, 2H), 7.51 (d, J=8.8 Hz, 2H), 6.20 (t, J=5.6 Hz, 1H), 4.36 (m, 2H), 4.02-3.71 (m, 4H), 3.60-3.44 (m, 2H), 3.18 (m, 2H), 1.44 (t, J=7.2 Hz, 3H), 1.15 (d, J=6.3 Hz, 3H), 1.07 (t, J=7.2 Hz, 3H). LC/MS-m/z+410.2 (M+H)+.

Example 8

Preparation of (S)-1-(4-(8-butyl-7-methyl-6-(3-methylmorpholino)-7H-purin-2-yl)phenyl)-3-ethylurea (h-2)

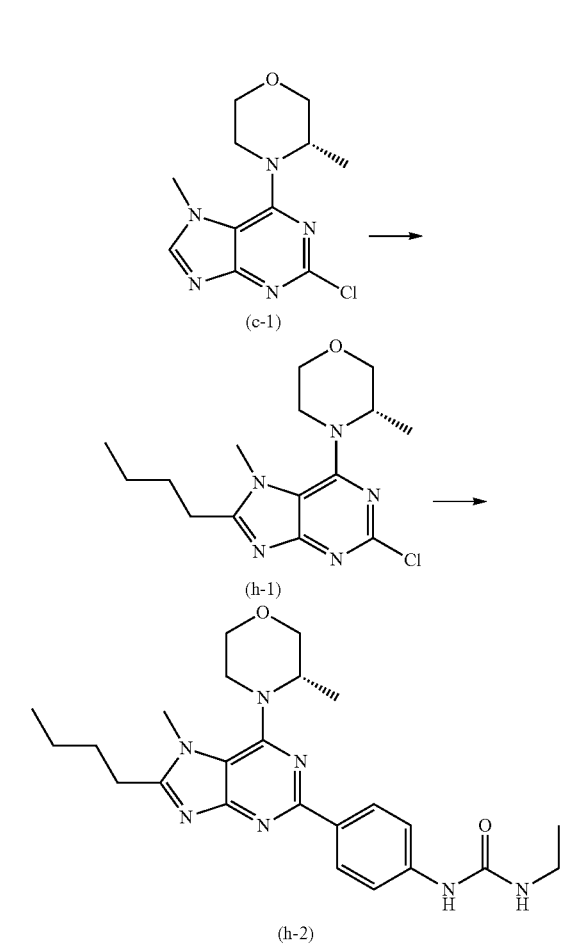

Preparation of (S)-4-(8-butyl-2-chloro-7-methyl-7H-purin-6-yl)-3-methylmorpholine (h-1: Compound (h-1) was prepared by dissolution of (S)-4-(2-chloro-7-methyl-7H-purin-6-yl)-3-methylmorpholine (c-1, 52.3 mg. 0.195 mmol) in anhydrous THF (1.6 mL) under nitrogen, cooling to −78° C. in a dry ice acetone cooling bath and at −78° C. adding nBuLi (0.23 mL of a 2.5M n-Butyllithium solution in hexane, 0.58 mmol) dropwise slowly. After vigorous stirring at −78° C. for 2 h, the reaction was quenched with excess acetone to obtain the desired tertiary alcohol. The reaction was warmed to room temperature and the solvent removed to give a waxy solid. LCMS indicated the major uv active product with a ret. time 2.30 min (Method C) present exhibited a M+H+ of 324.1 consistent with the C-8 butyl addition product. The crude product was purified by RP HPLC to afford 24 mg (20%) of (b) of >95% purity. $^1$H NMR (500 MHz, DMSO d$_6$) 3.93-3.80 (m+s, 5H), 3.66 (m, 1H), 3.54 (dd, J=11.4, 3.8 Hz, 1H), 3.52-4.42 (m, 1H), 3.21 (m, 1H), 2.86 (dd, J=8.2, 6.6 Hz, 2H), 1.81-1.69 (m, 2H), 1.42 (dq, J=14.7, 7.4 Hz, 2H), 1.13 (d, J=6.5 Hz, 3H), 0.94 (t, J=7.4 Hz, 3H). LC/MS-m/z+324.1 (M+H)+.

Preparation of (S)-1-(4-(8-butyl-7-methyl-6-(3-methylmorpholino)-7H-purin-2-yl)phenyl)-3-ethylurea (h-2): (S)-1-(4-(8-butyl-7-methyl-6-(3-methylmorpholino)-7H-purin-2-yl)phenyl)-3-ethylurea was prepared as described for Example 2 from 24 mg of (h-1) and purified by RP HPLC to afford 11.9 mg (35%) which was analyzed for identity and purity via LCMS (Method C). $^1$H NMR (500 MHz, DMSO d$_6$) 8.80 (s, 1H), 8.22 (d, J=8.8 Hz, 2H), 7.49 (d, J=8.8 Hz, 2H), 6.36 (t, J=5.3 Hz, 1H), 3.99-3.82 (m+s 5H), 3.75 (m, 2H), 3.21-3.02 (m, 5H), 2.96-2.75 (m, 2H), 1.92-1.69 (m, 2H), 1.44 (dd, J=15, 7.4 Hz, 2H), 1.12 (d, J=6.2 Hz, 3H), 1.05 (t, J=7.2 Hz, 3H), 0.95 (t, J=7.4 Hz, 3H) LC/MS-m/z+452.3 (M+H)+.

Example 9

Preparation of (S)-1-ethyl-3-(4-(8-(2-hydroxypropan-2-yl)-7-methyl-6-(3-methylmorpholino)-7H-purin-2-yl)phenyl)urea (1-2)

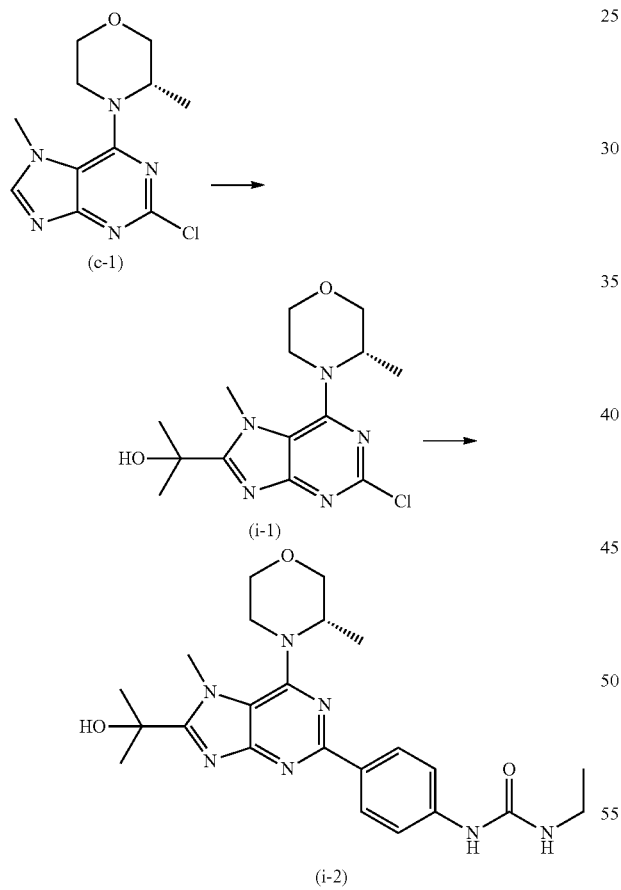

Preparation of 0.52M LDA in THF: An oven dried 100 mL round bottomed flask equipped with a stirring bar and under an atmosphere of nitrogen was charged with diisopropylamine (2.0 mL, 1.43 gm, 14.1 mmol), anhydrous DriSolv THF (26.4 mL, stabilized with ~25 ppm BHT), and cooled to 0° C. 2.5M nBuLi in THF (6.0 mL, 15 mmol, 1.06 equiv) was added dropwise at 0°. Removed from the ice bath and warmed to room temperature and stirred under nitrogen at room temperature for 2.5 h. The LDA was typically used immediately after preparation but could be stored in the refrigerator for a period of one week.

Preparation of (5)-2-(2-chloro-7-methyl-6-(3-methylmorpholino)-7H-purin-8-yl)propan-2-ol (i-1): An oven dried 25 mL round bottomed flask equipped with a stir bar and cooled under nitrogen was charged with 5.3 mL of 0.52M LDA (2.8 mmol, 5.0 equiv), cooled to −78° C. and stirred at −78° C. for 10 minutes. (5)-4-(2-chloro-7-methyl-7H-purin-6-yl)-3-methylmorpholine (c-1, 148 mg. 0.553 mmol) was dissolved in anhydrous THF (6.0 mL, 0.092M) and added dropwise slowly over 12 minutes. A color change from light yellow to orange was noted upon addition. Upon completion of addition of (a), the reaction mixture was stirred at −78° C. for 55 min at which time it was quenched with excess acetone (1.0 mL, 13.6 mmol, 25 equiv) and warmed to room temperature. LCMS analysis indicated the major uv active product exhibited the M=H+ for (i-1). The reaction was worked up by evaporation to dryness. The residue was dissolved in ethyl acetate, transferred to a separatory funnel, treated 1× with water and 1× with brine. The aqueous extract was extracted additionally with ethyl acetate, the ethyl acetate extracts combined, dried (MgSO$_4$), filtered, and concentrated to yield 152.5 mg of a crude orange/yellow solid. The crude was purified by silica chromatography (ISCO heptane/ethyl acetate 15-100%) to afford 109 mg (60%) of (b) as a white foam. $^1$H NMR (400 MHz, CDCl$_3$) 5.28 (s, 1H), 4.15 (s, 3H), 3.88 (dd, J=8.2, 3.7 Hz, 3H), 3.78 (m, 1H), 3.59 (dd, J=12, 5.0 Hz, 1H), 3.50 (ddd, J=11.7, 8.4, 3.1 Hz, 1H), 3.28 (m, 1H), 1.78 (s, 3H), 1.75 (s, 3H), 1.22 (d, J=6.7 Hz, 3H). LC/MS-m/z+326.4 (M+H)+.

Preparation of (S)-1-ethyl-3-(4-(8-(2-hydroxypropan-2-yl)-7-methyl-6-(3-methylmorpholino)-7H-purin-2-yl)phenyl)urea (i-2): Compound (1-2) was prepared as described for Example 2 from 44 mg of (i-1) and purified by RP HPLC to afford 26.7 mg (45%) which was analyzed for identity and purity via LCMS (Method C). $^1$H NMR (400 MHz, DMSO d$_6$) 8.60 (s, 1H), 8.24 (d, J=8.7 Hz, 2H), 7.49 (d, J=8.7 Hz, 2H), 6.17 (t, J=5.5 Hz, 1H), 5.69 (s, 1H), 4.18 (s, 3H), 4.02-3.67 (m 4H), 3.68-3.39 (m, 2H), 3.24-3.0 (m, 3H), 1.66 (s, 3H), 1.64 (s, 3H), 1.13 (d, J=6.4 Hz, 3H), 1.07 (t, J=7.2 Hz, 3H) LC/MS-m/z+454.2 (M+H)+.

Example 10

Synthesis of (S)-3-ethylmorpholine hydrobromide (j-1)

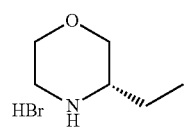

Step 1: Preparation of a (S)—N-(1-hydroxybutan-2-yl)-4-methylbenzene-sulfonamide (j-2)

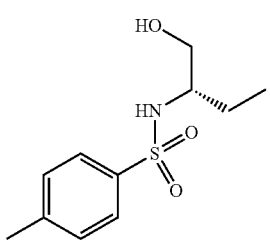

(2S)-2-Aminobutan-1-ol (2.1 mL, 22 mmol) and triethylamine (3.8 mL, 27 mmol) were dissolved in methylene chloride (30 mL, 500 mmol) and the solution was stirred at 0° C. for 5 minutes. Then, p-toluenesulfonyl chloride (4.3 g, 22 mmol) was added and the mixture was stirred while allowed to warm up to room temperature. The reaction was quenched with water and the phases were separated. The aqueous phase was extracted with 1×50 mL of DCM. The combined organic phases were washed with 1N HCl (50 mL), sat. NaHCO$_3$ (50 mL) and brine (50 mL), dried with MgSO$_4$, filtered and concentrated to give a white solid. The crude material was crystallized in ether/hexane to give(S)—N-(1-hydroxybutan-2-yl)-4-ethylbenzenesulfonamide (j-2) as a white solid: $^1$H NMR (400 MHz, DMSO) δ 7.69 (d, J=8.2 Hz, 2H), 7.38 (t, J=9.0 Hz, 3H), 4.62 (t, J=5.6 Hz, 1H), 3.24 (dd, J=10.3, 5.2 Hz, 1H), 3.18-3.02 (m, 1H), 2.92 (dd, J=7.9, 4.2 Hz, 1H), 1.61-1.39 (m, 1H), 1.19 (dd, J=14.5, 7.1 Hz, 1H), 0.63 (t, J=7.4 Hz, 3H); LC-MS: m/z=244 (M+H).

Step 2: Preparation of (S)-3-ethyl-4-tosylmorpholine (j-3)

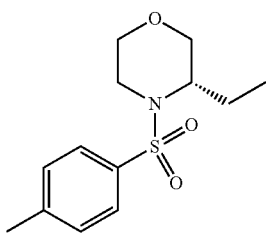

(S)—N-(1-hydroxybutan-2-yl)-4-methylbenzene-sulfonamide (800 mg, 3 mmol) was dissolved in dichloromethane (20 mL) and triethylamine (0.92 mL, 6.6 mmol) was added. The mixture was stirred at 0° C. for 10 minutes. Diphenyl(vinyl)sulfonium trifluoromethanesulfonate (1.25 g, 3.45 mmol), dissolved in dichloromethane (10 mL) was added dropwise over 5 minutes. The mixture was stirred while allowed to warm up to room temperature overnight. Saturated aqueous NH$_4$Cl was added and the phases were separated. The aqueous phase was extracted with 2×30 mL of DCM. The combined organic phases were dried with MgSO$_4$ and filtered. The filtrate was concentrated on silica gel and purified by flash chromatography (100% Hex to 60% EtOAc/Hex) to give (S)-3-ethyl-4-tosylmorpholine (j-3) as a white solid: $^1$H NMR (400 MHz, CDCl$_3$) δ 7.71 (d, J=8.3 Hz, 2H), 7.30 (t, J=8.3 Hz, 2H), 3.77-3.60 (m, 3H), 3.60-3.44 (m, 2H), 3.44-3.19 (m, 3H), 2.43 (s, 3H), 1.67 (dtd, J=28.6, 14.0, 7.4 Hz, 2H), 1.31-1.12 (m, 2H), 0.97-0.84 (m, 3H); LC-MS: m/z=270 (M+H).

Step 3: Preparation of (S)-3-ethylmorpholine hydrobromide (j-1): (S)-3-ethyl-4-tosylmorpholine (220 mg, 0.82 mmol) and phenol (150 mg, 1.6 mmol) were dissolved in 4.1 M of hydrogen bromide in acetic acid (2.4 mL) and the solution was stirred at room temperature overnight. The reaction was poured on ether and the solid was collected by filtration and washed with ether to give (S)-3-ethylmorpholine hydrobromide (j-1) as a white solid: $^1$H NMR (400 MHz, CDCl$_3$) δ 3.77-3.60 (m, 3H), 3.60-3.44 (m, 2H), 3.44-3.19 (m, 3H), 1.67 (dtd, J=28.6, 14.0, 7.4 Hz, 2H), 1.31-1.12 (m, 2H), 0.97-0.84 (m, 3H).

Example 11

Synthesis of (S)-4-(5-chloro-1-methyl-1H-pyrazolo[4,3-d]pyrimidin-7-yl)-3-methylmorpholine (k-1)

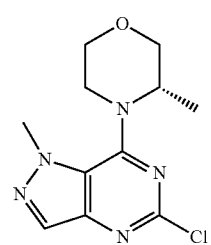

Step 1: Preparation of 1-methyl-1H-pyrazolo[4,3-d]pyrimidine-5,7(4H,6H)-dione (k-2)

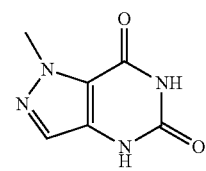

This compound was prepared following the method described in WO2008/071650. To a stirred solution of 1-methyl-4-nitro-1H-pyrazole-5-carboxamide (1.27 g, 9.06 mmol) in acetonitrile (35.6 mL) refluxed at 100° C. was added N,N-carbonyldimidazole (1.91 g, 11.78 mmol, 1.3 eq.) proportion wise over 1 hour. The reaction mixture was stirred at 100° C. under N$_2$ for 18 hours. The resultant precipitate was filtered, rinsed well with cold acetonitrile, and pumped dry on high-vac to yield 1.38 g (91.5%) of a white solid. $^1$H NMR (DMSO-d$_6$, 500 MHz) δ ppm 11.04 (broad d, 2H), 7.34 (s, 1H), 4.04 (s, 3H).

Step 2: Preparation of 5,7-dichloro-1-methyl-1H-pyrazolo[4,3-d]pyrimidine (k-3)

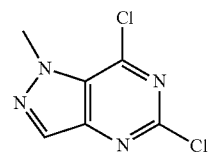

To a heterogenous mixture of 1-methyl-1H-pyrazolo[4,3-d]pyrimidine-5,7(4H,6H)-dione (k-2, 500.0 mg, 2.97 mmol) in N,N-diethylaniline (14 mL) was added phosphoryl chloride (20 mL), and the reaction mixture was stirred at 130° C. under N$_2$ for 18 hours. The reaction was cooled to 0° C. and quenched with saturated aqueous solution of sodium bicarbonate. The aqueous phase was extracted with ethyl acetate (3×), and the combined organic phase was washed with water and brine, dried over Na₂SO₄, filtered and concentrated in vacuo. The resultant residue was purified by column chromotagraphy (Si-PPC, gradient 0 to 60% DCM in heptane). Crystallization from ether-heptane afforded the desired product as a solid (435.8 mg, 72.2%). $^1$H NMR (CDCl₃, 500 MHz) δ ppm 8.17 (s, 1H), 4.41 (s, 3H); LC-MS m/z (method B2)=203/205 [M+H]⁺, $R_T$=1.55 min.

Step 3: Preparation of (S)-4-(5-chloro-1-methyl-1H-pyrazolo[4,3-d]pyrimidin-7-yl)-3-methylmorpholine (k-1): To a stirred solution of 5,7-dichloro-1-methyl-1H-pyrazolo[4,3-d]pyrimidine (200.0 mg, 0.98 mmol) in anhydrous DMF (2 mL) was added N,N-diisopropylethylamine (0.21 mL, 1.18 mmol, 1.2 eq.) followed by (S)-3-methylmorpholine (199.3 mg, 1.9 mmol, 2.0 eq.). The reaction mixture was stirred at RT under N₂ for 4 h and diluted with ether (50 mL). The organic layer was washed with saturated aqueous solution of sodium bicarbonate, water and brine, dried over Na₂SO₄, filtered, and concentrated in vacuo. The resultant residue was purified by column chromatagraphy (Si-PPC, gradient 0 to 100% ethyl acetate in heptane) to afford the desired product (k-1) as a foam (245.4 mg, 93.0%). $^1$H NMR (CDCl₃, 500 MHz) δ ppm 8.03 (s, 1H), 4.21 (broad d, J=6.2 Hz, 1H), 4.15 (s, 3H), 3.97 (d, J=10.7 Hz, 1H), 3.90 (d, J=9.8 Hz, 1H), 3.81 to 3.65 (m, 3H), 3.56 (d, J=12.4 Hz, 1H), 1.38 (d, J=6.6 Hz, 3H); LC-MS m/z (method A)=268 [M+H]⁺, $R_T$=1.71 min.

Example 12

Synthesis of (S)-4-(5-chloro-1-methyl-1H-pyrazolo[4,3-d]pyrimidin-7-yl)-3-ethylmorpholine (1-1)

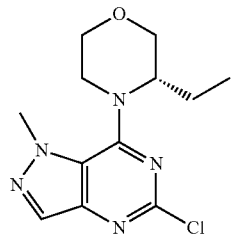

(1-1)

This compound was prepared in an analogous fashion to (S)-4-(5-chloro-1-methyl-1H-pyrazolo[4,3-d]pyrimidin-7-yl)-3-methylmorpholine, using (S)-ethyl-morpholine hydrobromide as the starting material. $^1$H NMR (CDCl₃, 500 MHz) δ ppm 8.00 (s, 1H), 4.15 to 4.07 (m, 4H), 3.92 (dd, J=11.8 Hz, 3.8 Hz, 1H), 3.88 (d, J=1.9 Hz, 2H), 3.82 to 3.71 (m, 1H), 3.67 to 3.56 (m, 2H), 2.03 to 1.82 (m, 2H), 0.90 (t, J=7.4 Hz, 3H); LC-MS m/z (method A)=282 [M+H]⁺, $R_T$=1.95 min.

Example 13

Preparation of (1S,4S)-5-(5-chloro-1-methyl-1H-pyrazolo[4,3-d]-pyrimidin-7-yl)-2-oxa-5-azabicyclo[2.2.1]heptane (m-1)

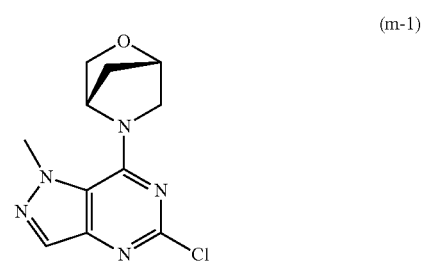 [SMILES: Cn1ncc2nc(Cl)nc(N3C[C@@H]4C[C@H]3CO4)c21]

(m-1)

This compound was prepared in an analogous fashion to (S)-4-(5-chloro-1-methyl-1H-pyrazolo[4,3-d]pyrimidin-7-yl)-3-methylmorpholine, using (1S,4S)-2-oxa-5-azabicyclo[2.2.1]heptane hydrochloride salt as the starting material. $^1$H NMR (CDCl₃, 500 MHz) δ ppm 7.96 (s, 1H), 5.15 (s, 1H), 4.76 (s, 1H), 4.20 (s, 3H), 4.13 (d, J=8.1 Hz, 1H), 3.97 (ddd, J=7.0 Hz, 4.7 Hz, 1.5 Hz, 2H), 3.69 (d, J=9.5 Hz, 1H), 2.09 to 1.94 (m, 2H); LC-MS m/z (method A)=266.1 [M+H]⁺, $R_T$=1.37 min.

Example 14

Preparation of (S)-4-(5-chloro-1,3-dimethyl-1H-pyrazolo[4,3-d]pyrimidin-7-yl)-3-ethylmorpholine (n-1)

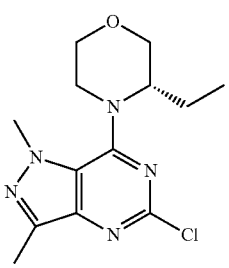

(n-1)

Step 1: Preparation of 1,3-dimethyl-4-nitro-1H-pyrazole-5-carboxylic acid (n-2)

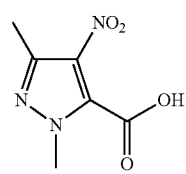

(n-2)

To fuming nitric acid (1.26 mL, 29.97 mmol, 2.0 eq.) at 0° C. was slowly added fuming sulfuric acid (9.76 mL, 104.90 mmol, 7.0 eq.) dropwise over 30 minutes. 1,3-Dimethyl-1H-pyrazole-5-carboxylic acid (2.10 g, 14.98 mmol) was then added portion wise, maintaining the internal temperature below 60° C. The reaction mixture was stirred at 60° C. under N₂ for 4 h and then cooled to room temperature (RT). The reaction mixture was poured onto ice. Once ice melted the reaction mixture was extracted with EtOAc (3×500 mL). The organic layers were combined and washed with water and brine, dried (Na₂SO₄), filtered and evaporated in vacuo to give the desired compound as a white solid (2.67 g, 96.1%). ¹H NMR (DMSO-d₆, 500 MHz) δ ppm 3.87 (s, 3H), 2.39 (s, 3H); TLC (15% MeOH/DCM): R$_f$=0.12.

Step 2: Preparation of 1,3-dimethyl-4-nitro-1H-pyrazole-5-carboxamide (n-3)

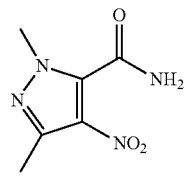

(n-3)

To 1,3-dimethyl-4-nitro-1H-pyrazole-5-carboxylic acid (1.08 g, 5.84 mmol) in anhydrous dichloromethane (DCM) (25 mL) and DMF (0.5 mL) was added dropwise oxalyl chloride (0.74 mL, 8.77 mmol, 1.5 eq.) over 10 minutes. The reaction mixture was stirred at RT under N₂ for 17 hours. Volatile solvent was evaporated in vacuo, and the crude material dissolved in anhydrous THF (20 mL) and acetone (10 mL). Concentrated aqueous ammonium hydroxide (5.0 mL, 128.4 mmol, 22 eq.) was added slowly, and the reaction mixture was stirred at RT for 16 hours. The reaction mixture was concentrated in vacuo, and the residue was diluted with ethyl acetate. The organic layer was washed with saturated aqueous solution of sodium bicarbonate, water and brine, dried (Na₂SO₄), filtered and concentrated in vacuo. Trituration from ether-heptane afforded the desired product as a white solid (550.0 mg, 51.5%). ¹H NMR (DMSO-d₆, 500 MHz) δ ppm 8.39 (broad s, 1H), 8.21 (broad s, 1H), 3.77 (s, 3H), 2.42 (s, 3H).

Step 3: Preparation of 4-amino-1,3-dimethyl-1H-pyrazole-5-carboxamide (n-4)

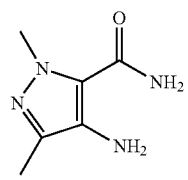

(n-4)

To a solution of 1,3-dimethyl-4-nitro-1H-pyrazole-5-carboxamide (730 mg, 3.96 mmol) in anhydrous ethanol (100 mL) and ethyl acetate (100 mL) was added 10 wt % Pd on carbon (100.0 mg). The reaction mixture was evacuated with vacuum and purged with H₂ (3×), then stirred under H₂ at 50 psi for 5 hours. The reaction mixture was then filtered through a pad of Celite®. The filtrate was concentrated in vacuo and the crude was purified by column chromatography (Si-PPC, gradient 0 to 30% methanol in dichloromethane) to get the desired product (597.0 mg, 97.7%) as a solid. ¹H NMR (DMSO-d₆, 400 MHz) δ ppm 7.26 (br s, 2H), 4.03 (br s, 2H), 3.84 (s, 3H), 2.02 (s, 3H); LC-MS m/z (method A)=155.2 [M+H]⁺, R$_T$=0.35 min.

Step 4: Preparation of 1,3-dimethyl-1H-pyrazolo[4,3-d]pyrimidine-5,7(4H,6H)-dione (n-5)

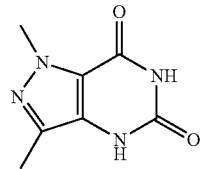

(n-5)

This compound was prepared in an analogous fashion to 1-methyl-1H-pyrazolo[4,3-d]pyrimidine-5,7(4H,6H)-dione, using 4-amino-1,3-dimethyl-1H-pyrazole-5-carboxamide as the starting material. ¹H NMR ((DMSO-d₆, 400 MHz) δ ppm 11.02 (s, 2H), 3.97 (s, 3H), 2.20 (s, 3H).

Step 5: Preparation of 5,7-dichloro-1,3-dimethyl-1H-pyrazolo[4,3-d]pyrimidine (n-6)

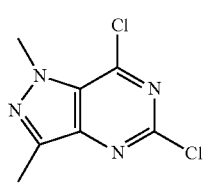

(n-6)

This compound was prepared in an analogous fashion to 5,7-dichloro-1-methyl-1H-pyrazolo[4,3-d]pyrimidine, using 1,3-dimethyl-1H-pyrazolo[4,3-d]-pyrimidine-5,7(4H,6H)-dione as the starting material. ¹H NMR (CDCl₃, 400 MHz) δ ppm 4.32 (s, 3H), 2.60 (s, 3H); LC-MS m/z (method B2)=217.2/219.2 [M+H]⁺, R$_T$=1.688 min.

Step 6: Preparation of (S)-4-(5-chloro-1,3-dimethyl-1H-pyrazolo[4,3-c]pyrimidin-7-yl)-3-ethylmorpholine (n-1): This compound was prepared in an analogous fashion to (S)-4-(5-chloro-1-methyl-1H-pyrazolo[4,3-d]pyrimidin-7-yl)-3-methylmorpholine, using 5,7-dichloro-1,3-dimethyl-1H-pyrazolo[4,3-d]pyrimidine as the starting material. ¹H NMR (CDCl₃, 400 MHz) δ ppm 4.08 (t, J=7.3 Hz, 1H), 4.01 (s, 3H), 3.96 to 3.84 (m, 3H), 3.79 to 3.67 (m, 1H), 3.67 to 3.56 (m, 2H), 2.53 (s, 3H), 2.05 to 1.78 (m, 2H), 0.89 (t, J=7.5 Hz, 3H); LC-MS m/z (method A)=296.3 [M+H]⁺, R$_T$=2.16 min.

Example 15

Synthesis of (S)-1-ethyl-3-(4-(1-methyl-7-(3-methylmorpholino)-1H-pyrazolo[4,3-d]pyrimidin-5-yl)phenyl)urea (o-1)

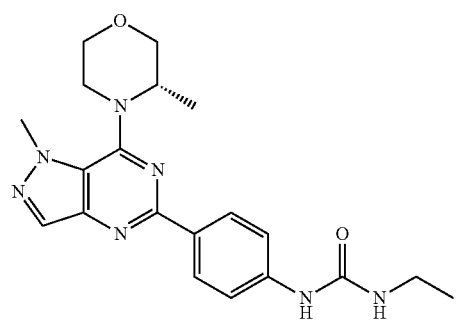

(o-1)

In a 5-mL microwave vessel equipped with a stir bar was placed (S)-4-(5-chloro-1-methyl-1H-pyrazolo[4,3-d]pyrimidin-7-yl)-3-methylmorpholine (91.5 mg, 0.34 mmol), [4-ethylureido)phenyl]boronic acid, pinacol ester (121.0 mg, 0.42 mmol, 1.22 eq.), tetrakis(triphenylphosphine)palladium (0) (24.5 mg, 0.022 mmol, 0.062 eq.), sodium carbonate (55.4 mg, 0.52 mmol, 1.53 eq.), and potassium acetate (54.7 mg, 0.56 mmol, 1.63 eq.). Degassed acetonitrile (3.5 mL) and water (1.2 mL) were added. The microwave vial was capped, and the reaction mixture was heated under microwave irradiation (300 watts, 120° C.) for 15 minutes. The reaction mixture was diluted with ethyl acetate (10 mL) and filtered through a pad of Celite®. The organic layer was washed with water and brine, then dried (Na$_2$SO$_4$), filtered and evaporated in vacuo. The resultant residue was purified by reverse phase HPLC to give the title compound as a white solid (102.6 mg, 75.9%). $^1$H NMR (DMSO-d$_6$, 400 MHz) δ ppm 8.62 (s, 1H), 8.24 (d, J=8.7 Hz, 2H), 8.20 (s, 1H), 7.50 (d, J=8.8 Hz, 2H), 6.16 (t, J=5.5 Hz, 1H), 4.25 to 4.11 (m, 4H), 3.96 to 3.83 (m, 2H), 3.73 (t, J=11.2 Hz, 1H), 3.69 to 3.59 (m, 2H), 3.50 (d, J=13.3 Hz, 1H), 3.19 to 3.06 (m, 2H), 1.27 (d, J=6.5 Hz, 3H), 1.07 (t, J=7.2 Hz, 3H); LC-MS m/z (method C1)=396.2 [M+H]$^+$, R$_T$=3.31 min.

Example 16

Synthesis of (S)-1-ethyl-3-(4-(7-(3-ethylmorpholino)-1-methyl-1H-pyrazolo[4,3-d]pyrimidin-5-yl)phenyl)urea (p-1)

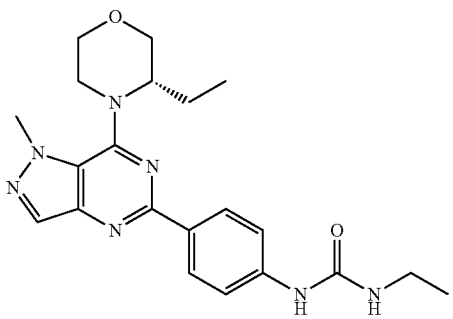

(p-1)

The title compound was prepared accordingly to the procedure described as for Example 15. Using (S)-4-(5-chloro-1-methyl-1H-pyrazolo[4,3-d]pyrimidin-7-yl)-3-ethylmorpholine, the title compound was obtained. $^1$H NMR (DMSO-d$_6$, 400 MHz) δ ppm 8.60 (s, 1H), 8.23 (d, J=8.7 Hz, 2H), 8.18 (s, 1H), 7.49 (d, J=8.7 Hz, 2H), 6.16 (t, J=5.5 Hz, 1H), 4.19 to 4.07 (m, 4H), 3.92 to 3.80 (m, 3H), 3.75 to 3.54 (m, 3H), 3.19 to 3.07 (m, 2H), 1.91 to 1.79 (m, 2H), 1.07 (t, J=7.2 Hz, 3H), 0.83 (t, J=7.4 Hz, 3H); LC-MS m/z (method C2)=410.2 [M+H]$^+$, R$_T$=9.11 min.

Example 17

Synthesis of 1-(4-(7-((1S,4S)-2-oxa-5-azabicyclo[2.2.1]heptan-5-yl)-1-methyl-1H-pyrazolo[4,3-d]pyrimidin-5-yl)phenyl)-3-ethylurea (q-1)

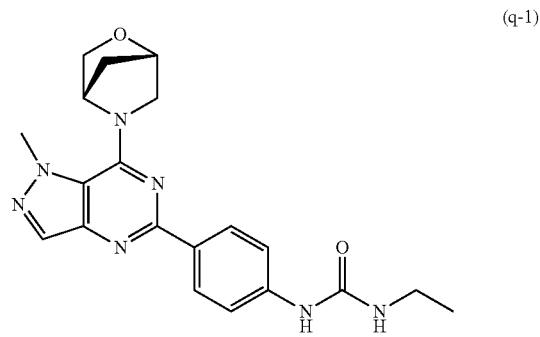 [SMILES: CCNC(=O)Nc1ccc(-c2nc(N3C[C@@H]4C[C@H]3CO4)c3c(cnn3C)n2)cc1]

(q-1)

The title compound was prepared accordingly to the procedure described as for Example 15. Using (1S,4S)-5-(5-chloro-1-methyl-1H-pyrazolo[4,3-d]-pyrimidin-7-yl)-2-oxa-5-azabicyclo[2.2.1]heptane, the title compound was obtained. $^1$H NMR (DMSO-d$_6$, 400 MHz) δ ppm 8.62 (s, 1H), 8.22 (d, J=8.7 Hz, 2H), 8.11 (s, 1H), 7.47 (d, J=8.7 Hz, 2H), 6.16 (t, J=5.5 Hz, 1H), 5.21 (s, 1H), 4.73 (s, 1H), 4.19 (s, 3H), 4.09 (d, J=9.6 Hz, 1H), 4.02 (d, J=7.6 Hz, 1H), 3.91 (d, J=7.6 Hz, 1H), 3.63 (d, J=9.8 Hz, 1H), 3.15 to 3.07 (m, 2H), 1.94 (dd, J=25.8 Hz, 9.8 Hz, 2H), 1.07 (t J=7.1 Hz, 3H); LC-MS m/z (method C)=394.2 [M+H]$^+$, R$_T$=3.07 min.

Example 18

Synthesis of (S)-1-ethyl-3-(4-(7-(3-ethylmorpholino)-1,3-dimethyl-1H-pyrazolo[4,3-d]pyrimidin-5-yl)phenyl)urea (r-1)

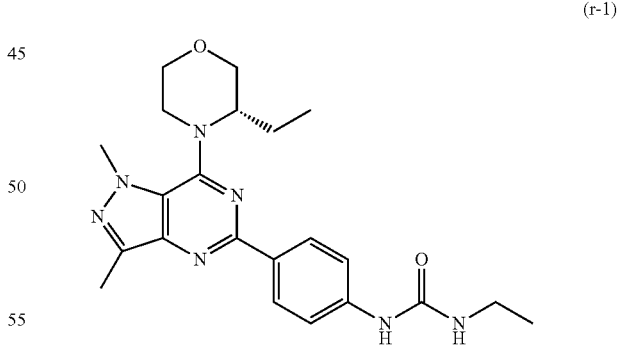

(r-1)

The title compound was prepared accordingly to the procedure described as for Example 15. Using (S)-4-(5-chloro-1,3-dimethyl-1H-pyrazolo[4,3-c]pyrimidin-7-yl)-3-ethylmorpholine, the title compound was obtained. $^1$H NMR (DMSO-d$_6$, 400 MHz) δ ppm 8.60 (s, 1H), 8.24 (d, J=8.7 Hz, 2H), 7.49 (d, J=8.7 Hz, 2H), 6.14 (t, J=5.5 Hz, 1H), 4.09 (broad s, 1H), 4.03 (s, 3H), 3.92 to 3.79 (m, 3H), 3.73 to 3.54 (m, 3H), 3.20 to 3.05 (m, 2H), 2.48 (s, 3H), 1.90 to 1.76 (m, 2H), 1.07 (t, J=7.2 Hz, 3H), 0.82 (t, J=7.4 Hz, 3H); LC-MS m/z (method C)=424.2 [M+H]$^+$, R$_T$=3.65 min.

Example 19

Synthesis of (S)-1-(4-(1-methyl-7-(3-methylmorpholino)-1H-pyrazolo[4,3-d]pyrimidin-5-yl)phenyl)-3-(oxetan-3-yl)urea (s-1)

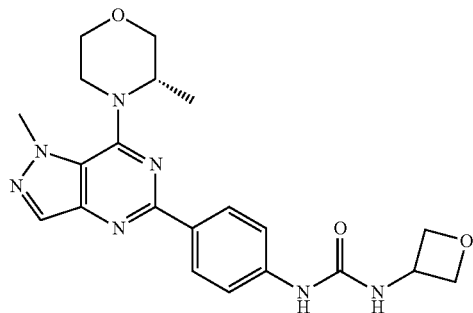

(s-1)

Step 1: Preparation of (S)-3-methyl-4-(1-methyl-5-(4-nitrophenyl)-1H-pyrazolo[4,3-d]pyrimidin-7-yl)morpholine (s-2)

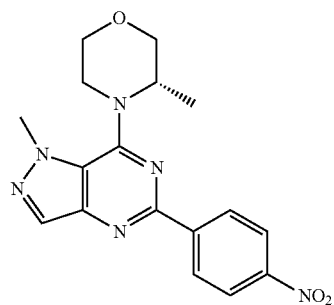

(s-2)

This compound was prepared in an analogous fashion to (S)-1-ethyl-3-(4-(1-methyl-7-(3-methylmorpholino)-1H-pyrazolo[4,3-d]pyrimidin-5-yl)phenyl)urea, using 4-nitrophenylboronic acid pinacol ester as the starting material. $^1$H NMR (CDCl$_3$, 400 MHz) δ ppm 8.62 (d, J=9.0 Hz, 2H), 8.32 (d, J=9.0 Hz, 2H), 8.22 (s, 1H), 4.27 to 4.17 (m, 4H), 4.08 to 3.95 (m, 2H), 3.93 to 3.82 (m, 1H), 3.79 to 3.67 (m, 2H), 3.60 to 3.50 (m, 1H), 1.38 (d, J=6.6 Hz, 3H).

Step 2: Preparation of (S)-4-(1-methyl-7-(3-methylmorpholino)-1H-pyrazolo[4,3-d]pyrimidin-5-yl)aniline (s-3)

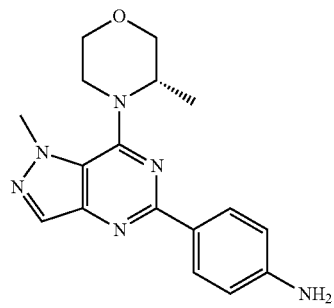

(s-3)

A solution of (S)-3-methyl-4-(1-methyl-5-(4-nitrophenyl)-1H-pyrazolo[4,3-d]pyrimidin-7-yl)morpholine (122.4 mg, 0.345 mmol) dissolved in anhydrous THF (15 mL) was subjected to a continuous flow hydrogenated apparatus (H-Cube: 10% Pd/C cartridge, 1.0 mL/min flow). The crude was concentrated in vacuo and purified by column chromotagraphy (Si-PPC, gradient 0 to 100% EtOAc in heptane) to give the desired product as a yellow foam (92.0 mg, 82.1%). LC-MS m/z (method A)=325.4 [M+H]$^+$, R$_T$=1.34 min.

Step 3: Preparation of (S)-1-(4-(1-methyl-7-(3-methylmorpholino)-1H-pyrazolo[4,3-d]pyrimidin-5-yl)phenyl)-3-(oxetan-3-yl)urea (s-1): To a stirred solution of (S)-3-methyl-4-(1-methyl-5-(4-nitrophenyl)-1H-pyrazolo[4,3-d]pyrimidin-7-yl)morpholine (50.0 mg, 0.154 mmol) in anhydrous 1,2-dichoroethane (5.0 mL) was added triethylamine (0.071 mL, 0.51 mmol, 3.3 eq.). The reaction was cooled to 0° C. and triphosgene (45.7 mg, 0.154 mmol, 1.0 eq) was added in one portion. After stirring at 0° C. under N$_2$ for 5 minutes, the reaction mixture was stirred at 70° C. for 1 h. The reaction mixture was cooled to RT, and 3-oxetanamine hydrochloride (84.4 mg, 0.77 mmol, 5.0 eq.) was then added. The reaction mixture was stirred at RT under N$_2$ for 16 h and then diluted with EtOAc (25 mL). The organic layer was washed with water and brine, dried (Na$_2$SO$_4$), filtered and concentrated in vacuo. The crude was purified by column chromotagraphy (Si-PPC, gradient 50 to 100% EtOAc in heptane, followed by 0 to 30% methanol in dichloromethane). Trituration from methanol afforded the title compound (49.3 mg, 75.5%) as a solid. $^1$H NMR (DMSO-d$_6$, 400 MHz) δ ppm 8.76 (s, 1H), 8.25 (d, J=8.8 Hz, 2H), 8.21 (s, 1H), 7.50 (d, J=8.8 Hz, 2H), 6.97 (d, J=6.7 Hz, 1H), 4.85 to 4.69 (m, 3H), 4.44 (t, J=6.0 Hz, 2H), 4.23 to 4.12 (m, 4H), 3.96 to 3.81 (m, 2H), 3.72 (dd, J=14.7 Hz, 5.8 Hz, 1H), 3.69 to 3.58 (m, 2H), 3.50 (d, J=13.3 Hz, 1H), 1.26 (d, J=6.5 Hz, 3H); LC-MS m/z (method C1)=424.2 [M+H]$^+$, R$_T$=3.12 min.

Example 20

Synthesis of (S)-1-(4-(1-methyl-7-(3-methylmorpholino)-1H-pyrazolo-[4,3-d]pyrimidin-5-yl)phenyl)-3-(2-(methylsulfonyl)ethyl)urea (t-1)

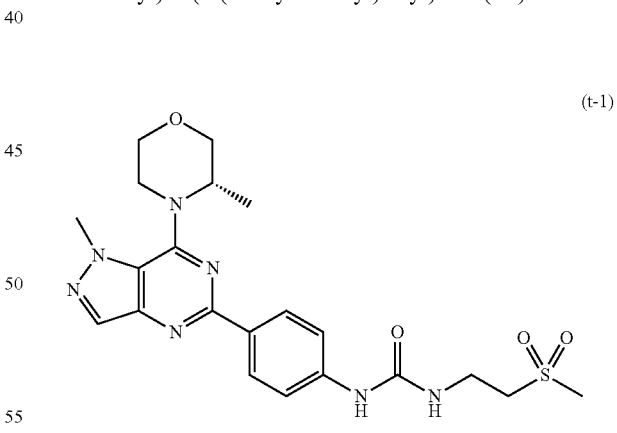

(t-1)

This compound was prepared in an analogous fashion to (S)-1-(4-(1-methyl-7-(3-methylmorpholino)-1H-pyrazolo[4,3-d]pyrimidin-5-yl)phenyl)-3-(oxetan-3-yl)urea, using 2-(methylsulfonyl)ethanamine hydrochloride as the starting material. $^1$H NMR (DMSO-d$_6$, 400 MHz) δ ppm 8.96 (s, 1H), 8.25 (d, J=8.8 Hz, 2H), 8.21 (s, 1H), 7.51 (d, J=8.8 Hz, 2H), 6.42 (t, J=5.9 Hz, 1H), 4.25 to 4.13 (m, 4H), 3.96 to 3.83 (m, 2H), 3.78 to 3.79 (m, 1H), 3.79 to 3.60 (m, 2H), 3.60 to 3.47 (m, 3H), 3.37 to 3.30 (m, 5H), 1.27 (d, J=6.5 Hz, 3H); LC-MS m/z (method C1)=474.2 [M+H]$^+$, R$_T$ =3.13 min

Example 21

Biological Evaluation of Compounds a. In Vitro mTOR Kinase Assay

The kinase activity of mTOR enzyme is assessed by incubating purified recombinant enzyme (mTOR(1360-2549)+GBL, prepared in-house) in a reaction mixture containing ATP, $MnCl_2$, and a fluorescently labeled mTOR substrate, e.g., GFP-4E-BP1 (Invitrogen, product #PR8808A). The reaction is stopped by an addition of a Terbium-labeled phospho-specific antibody, e.g., Tb-labeled anti-p4E-BP1 T37/T46, (Invitrogen, product #PR8835A), EDTA, and TR-FRET buffer solution (Invitrogen, Product #PR3756B). Product formation is detected by way of time-resolved fluorescence resonance energy transfer (TR-FRET), which occurs when the phosphorylated substrate and labeled antibody are in close proximity due to phospho-specific binding. Enzymatic activity is measured as an increase in TR-FRET signal using a Perkin Elmer Envision plate reader. The assay is performed in a 384-well Proxiplate Plus (Perkin Elmer. Product #6008269) using the following protocol:

Compound activity is tested in 10 point dose curves starting at the highest final concentration of 10 uM. They are serially diluted in 100% DMSO prior to further dilution with assay buffer. The reaction mixture (8 uls) containing 0.25 nM mTOR+GBL enzyme, 400 nM GFP-4E-BP1, 8 uM ATP, 50 mM Hepes pH 7.5, 0.01% Tween 20, 10 mM $MnCl_2$, 1 mM EGTA, 1 mM DTT, 1% DMSO (+/−compound) is incubated at room temperature for 30 minutes. 8 μL of solution containing 2 nM Tb-anti-p4E-BP1 antibody & 10 mM EDTA diluted TR-FRET buffer is then added and incubated for 30 minutes to stop the reaction. The plate is scanned with the Envision plate reader. Ki values are calculated in Assay Explorer using the Morrison ATP-competitive tight binding equation for Ki apparent determination.

Compounds of the invention (e.g., compounds of Formula I have an activity level (Ki) in the mTOR kinase assay of between about 0.0001 nM and about 5 uM, and in certain embodiments between about 0.0001 nM and about 1 uM, and in certain other embodiments less than between about 0.0001 nM and about 0.5 uM. Compounds 101-114 of the invention appearing in Table 1 have the following activity level (in uM): 0.143, 0.028, 0.069, 0.004, 0.121, 0.040, 0.053, 0.030, 0.008, 0.001, 0.028, 0.002, 0.039 and 0.145, respectively.

b. In Vitro Phospho-AKT Serine 473 Cellular Assay

The assay measures a test compound's inhibition of AKT serine-473 phosphorylation in human prostate adenocarcinoma derived PC-3 (ATCC CRL-1435) cells that have been stimulated with epidermal growth factor (EGF).

The PC-3 cell line is maintained in RPMI1640 media supplemented with 10% FBS, 2 mM Glutamine, and 10 mM HEPES pH 7.4 at 37° C. in a 5% CO2 humidified incubator.

Cells are seeded in 384-well plates at 7,000 cells/well in 50 μA growth media. After 24 hours, growth media is removed and replaced with RPMI1640 containing no FBS. Cells are treated with 10 concentrations of test compounds or DMSO alone for controls (final DMSO concentration 0.5%) and incubated at 37° C. for 30 minutes. Cells are then stimulated for 10 minutes with 100 ng/ml EGF (final concentration). One column of controls is not stimulated with EGF to observe the signal ratio between stimulated and non-stimulated cells. After 10 minutes, compounds and stimulation media are removed and replaced with 25 μl lysis buffer containing protease inhibitors and phosphatase inhibitors. This buffer contains detergent to bring about cellular disruption. Following complete cellular disruption, 20 μA lysate is transferred to a MesoScale Discovery 384 well 4-spot plate coated with an antibody to AKT (MesoScale Discovery (MSD) product K211 CAD-2) which have been previously blocked with 3% bovine serum albumin in Tris buffered saline. Following the transfer of lysate to the MSD plate, AKT in the lysate is captured on the coated antibody by incubation on a shaker at 4° C. for 16 hours. Following the capture step the plate is washed and then incubated for two hours with an antibody to S473 phosphorylated AKT which is conjugated with a Sulfo-Tag. This tag gives a signal when in proximity to the electrode on the base of the MSD plate. Binding the tagged antibody to the captured protein allow detection on a MSD reader.

The $EC_{50}$ is defined as the concentration at which a given compound achieves 50% decrease of the measured levels of S473 AKT phosphorylation. $EC_{50}$ values are calculated using MDL Assay Explorer 3.0.1.8 fitting a sigmoidal curve with a variable slope.

Compounds 101-108 described in Table 1 have an EC50 activity level of (in uM): N/A, 0.632, N/A, 0.069, N/A, 0.511, N/A and 3.5, respectively.

c. In Vitro Cell Proliferation Assay

Efficacy of Formula I compounds were measured by a cell proliferation assay employing the following protocol:

1. An aliquot of 20 μl of cell culture containing about $10^3$ cells (PC3 or MDAMB361.1) in medium was deposited in each well of a 384-well, opaque-walled plate.

2. Control wells were prepared containing medium and without cells; Cells were allowed to settle overnight.

3. The compound was added to the experimental wells and incubated for 3 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 20 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $IC_{50}$ values were calculated using a sigmoidal dose response curve fit. Compounds 101 to 114 of the invention described in Table 1 have an IC50 value of (in uM, with PC3 cells): N/A, 0.294, 10, 0.737, N/A. 4.2, 2.4, 8, 0.399, 0.131, 2.9, 0.086, 5.9, and N/A, respectively.

d. p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM Tris pH 7.5, 50 mM NaCl, 4 mM $MgCl_2$, 0.05% Chaps, and 1 mM DTT) to 10 mM $PIP_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda$ex=530 nm; $\lambda$em=590 nm) in 384-well black low volume Proxiplates (PerkinElmer, Wellesley, Mass.) Fluorescence polarization values were plotted as a function of the protein concentration, and the $EC_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110 alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda$ex=530 nm; $\lambda$em=590 nm) in 384-well black low volume proxi plates (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

We claim:
1. A compound of Formula I-A:

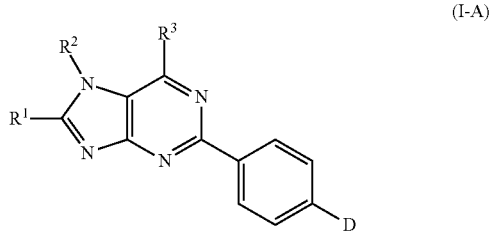

(I-A)

wherein $R^1$ is selected from the group consisting of hydrogen, $C_{1-6}$ alkyl, $C_{2-6}$ alkenyl, $C_{2-6}$ alkynyl, $C_{1-6}$ heteroalkyl, 6- to 10-membered aryl, 5- to 9-membered heteroaryl, 3- to 12-membered heterocycloalkyl, 3- to 12-membered cycloalkyl, wherein $R^1$ is substituted with from 0 to 5 $R^{R1}$ substituents selected from the group consisting of F, Cl, Br, I, $-NR^aR^b$, $-SR^a$, $-OR^a$, $-C(O)OR^a$, $-C(O)NR^aR^b$, $-C(O)R^a$, $-NR^aC(O)R^b$, $-OC(O)R^c$, $-NR^aC(O)NR^aR^b$, $-OC(O)NR^aR^b$, $-NR^aS(O)_2NR^aR^b$, $-S(O)_2R^a$, $-S(O)_2NR^aR^b$, $-R^c$, $-NO_2$, $-N_3$, $=O$, $-CN$, $R^{c1}$, $-X^1-NR^aR^b$, $-X^1-SR^a$, $-X^1-OR^a$, $-X^1-C(O)OR^a$, $-X^1-C(O)NR^aR^b$, $-X^1-C(O)R^a$, $-X^1-NR^aC(O)R^b$, $-X^1-OC(O)R^a$, $-X^1-NR^aC(O)NR^aR^b$, $-X^1-OC(O)NR^aR^b$, $-X^1-NR^aS(O)_2NR^aR^b$, $-X^1-S(O)_2R^a$, $-X^1-S(O)_2NR^aR^b$, $-X^1-NO_2$, $-X^1-N_3$, $-X^1-CN$, and $X^1-R^{c1}$; wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and $-(CH_2)_{1-4}$-phenyl, optionally $R^a$ and $R^b$, when attached to the same nitrogen atom are combined to form a 3- to 6-membered heterocyclic ring comprising 1 to 2 heteroatoms selected from N, O and S; $R^c$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and $-(CH_2)_{1-4}$-phenyl; $X^1$ is selected from the group consisting of $C_{1-4}$ alkylene, $C_{2-4}$ alkenylene and $C_{2-4}$ alkynylene; and $R^{c1}$ is selected from the group consisting of phenyl, 2-pyridyl, 3-pyridyl, 4-pyridyl, 2-imidazolyl, 2-indolyl, 1-naphthyl, 2-naphthyl, 2-thienyl, 3-thienyl, 2-pyrrolyl, 2-furanyl and 3-furanyl, and wherein $R^{c1}$ is substituted with from 0 to 3 substituents selected from F, Cl, Br, I, $-NR^aR^b$, $-SR^a$, $-OR^a$, $-S(O)_2R^a$, $-S(O)_2NR^aR^b$, $-NO_2$, $-N_3$, $=O$, $-CN$, pyridyl, $C_{1-6}$ alkyl, $C_{2-6}$ alkenyl, $C_{2-6}$ alkynyl and $C_{1-6}$ heteroalkyl;

$R^2$ is selected from the group consisting of hydrogen, $C_{1-6}$ alkyl, $C_{2-6}$ alkenyl, $C_{2-6}$ alkynyl, $C_{1-6}$ heteroalkyl, -L-$C_{6-10}$ aryl, -L-$C_{1-9}$ heteroaryl, -L-$C_{3-12}$ cycloalkyl and -L-$C_{2-12}$ heterocycloalkyl, wherein L is selected from $C_{1-6}$ alkylene, $C_{2-6}$ alkenylene, $C_{2-6}$ alkynylene and $C_{1-6}$ heteroalkylene, and wherein $R^2$ is substituted with from 0 to 5 $R^{R2}$ substituents selected from the group consisting of F, Cl, Br, I, $-NR^dR^e$, $-SR^d$, $-OR^d$, $-C(O)OR^d$, $-C(O)NR^dR^e$, $-C(O)R^d$, $-NR^dC(O)R^e$, $-OC(O)R^f$, $-NR^dC(O)NR^dR^e$, $-OC(O)NR^dR^e$, $-NR^dS(O)_2NR^dR^e$, $-S(O)_2R^d$, $-S(O)_2NR^dR^e$, $-R^f$, $-NO_2$, $-N_3$, $=O$, $-CN$, $-X^2-NR^dR^e$, $-X^2-SR^d$, $-X^2-OR^d$, $-X^2-C(O)OR^d$, $-X^2-C(O)NR^dR^e$, $-X^2-C(O)R^d$, $-X^2-NR^dC(O)R^e$, $-X^2-OC(O)R^d$, $-X^2-NR^dC(O)NR^dR^e$, $-X^2-OC(O)NR^dR^e$, $-X^2-NR^dS(O)_2NR^dR^e$, $-X^2-S(O)_2R^d$, $-X^2-S(O)_2NR^dR^e$, $-X^2-NO_2$, $-X^2-N_3$ and $-X^2-CN$; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and $-(CH_2)_{1-4}$-phenyl, optionally $R^d$ and $R^e$, when attached to the same nitrogen atom are combined to form a 3- to 6-membered heterocyclic ring comprising 1 to 2 heteroatoms selected from N, O and S; $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and $-(CH_2)_{1-4}$-phenyl; and $X^2$ is selected from the group consisting of $C_{1-4}$ alkylene, $C_{2-4}$ alkenylene and $C_{2-4}$ alkynylene;

$R^3$ is a 5- to 12-membered monocyclic or bridged heterocycloalkyl ring, wherein the $R^3$ group is substituted with from 0 to 3 $R^{R3}$ substituents selected from the group consisting of $-C(O)OR^g$, $-C(O)NR^gR^h$, $-NR^gR^h$, $-OR^g$, $-SR^g$, $-S(O)_2R^i$, $-S(O)R^i$, $-R^i$, F, Cl, Br, I, $-NO_2$, $-CN$ and $-N_3$, wherein $R^g$ and $R^h$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^g$ and $R^h$, together with the nitrogen atom to which each is attached, are combined to form a 3- to 6-membered heterocyclic ring comprising 1 to 2 heteroatoms selected from N, O and S, and $R^i$ is selected from $C_{1-6}$ alkyl, $C_{1-6}$ haloalkyl, $C_{2-6}$ alkenyl, and $C_{3-6}$ cycloalkyl; and when $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S; and D is a member selected from the group consisting of $-NR^4C(O)NR^5R^6$, wherein $R^4$ is selected from the group consisting of hydrogen, $C_{1-6}$ alkyl, $C_{1-6}$ haloalkyl and $C_{2-6}$ alkenyl; $R^5$ and $R^6$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{2-10}$ heterocycloalkyl, $C_{6-10}$ aryl and $C_{1-9}$ heteroaryl, and $R^5$ and $R^6$, when attached to the same nitrogen atom, are optionally combined to form a 5- to 7-membered heterocyclic or a 5- to 9-membered heteroaryl ring comprising 1 to 3 heteroatoms selected from N, O and S and substituted with 0-3 $R^D$ substituents; and wherein $R^4$, $R^5$ and $R^6$ are further substituted with from 0 to 3 $R^D$ substituents, wherein $R^D$ is independently selected from the group consisting of F, Cl, Br, I, —$NO_2$, —CN, —$NR^jR^k$, —$OR^j$, —$SR^j$, —$C(O)OR^j$, —$C(O)NR^jR^k$, —$NR^jC(O)R^k$, —$NR^jC(O)OR^m$, —$X^3$—$NR^jR^k$, —$X^3$—$OR^j$, —$X^3$—$SR^j$, —$X^3$—$C(O)OR^j$, —$X^3$—$C(O)NR^jR^k$, —$X^3$—$NR^jC(O)R^k$, —$X^3$—$NR^jC(O)OR^k$, —$X^3$—CN, —$X^3$—$NO_2$, —$S(O)R^m$, —$S(O)_2R^m$, =O, and —$R^m$; wherein $R^j$; and $R^k$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{1-9}$ heteroaryl; and $R^m$, at each occurrence, is independently selected from $C_{1-6}$ alkyl, $C_{1-6}$ haloalkyl, $C_{3-7}$ cycloalkyl, $C_{3-7}$ heterocycloalkyl, $C_{6-10}$ aryl and $C_{1-9}$ heteroaryl; and $X^3$ is selected from the group consisting of $C_{1-4}$ alkylene, $C_{2-4}$ alkenylene and $C_{2-4}$ alkynylene.

2. The compound of claim 1, wherein $R^3$ is selected from the group consisting of morpholin-4-yl, 3,4-dihydro-2H-pyran-4-yl, 3,6-dihydro-2H-pyran-4-yl, tetrahydro-2H-pyran-4-yl, 1,4-oxazepan-4-yl, 2-oxa-5-azabicyclo[2.2.1]heptan-5-yl, 3-oxa-8-azabicyclo[3.2.1]octan-8-yl, piperidin-1-yl, and 8-oxa-3-azabicyclo[3.2.1]octan-3-yl, wherein the $R^3$ group is substituted with from 0 to 3 $R^{R3}$ substituents selected from the group consisting of —$C(O)OR^g$, —$C(O)NR^gR^h$, —$NR^gR^h$, —$OR^g$, —$SR^g$, —$S(O)_2R^i$, —$S(O)R^i$, —$R^i$, F, Cl, Br, I, —$NO_2$, —CN and —$N_3$, wherein $R^g$ and $R^h$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^g$ and $R^h$, together with the nitrogen atom to which each is attached, are combined to form a 3- to 6-membered heterocyclic ring comprising 1 to 2 heteroatoms selected from N, O and S, and $R^i$ is selected from $C_{1-6}$ alkyl, $C_{1-6}$ haloalkyl, $C_{2-6}$ alkenyl, and $C_{3-6}$ cycloalkyl; and if $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S.

3. The compound of claim 2, wherein $R^3$ is substituted with from 0 to 2 $R^{R3}$ substituents selected from —$NR^gR^h$, —$OR^g$, and $R^i$, and when $R^3$ is a monocyclic heterocycloalkyl ring then any two $R^{R3}$ groups attached to the same atom of $R^3$ is optionally combined to form at 3- to 7-membered carbocyclic or 3- to 7-membered heterocyclic ring comprising 1 to 2 atoms selected from N, O and S.

4. The compound of claim 2, wherein $R^3$ is selected from the group consisting of morpholin-4-yl, 3(R)-methyl-morpholin-4-yl, 3(S)-methyl-morpholin-4-yl, 3(R)-ethyl-morpholin-4-yl, 3(S)-ethyl-morpholin-4-yl, 3(R)-isopropyl-morpholin-4-yl, 3(S)-isopropyl-morpholin-4-yl, 3,3-dimethyl-morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, 2-oxa-5-azabicyclo[2.2.1]heptan-5-yl, 3-oxa-8-azabicyclo[3.2.1]octan-8-yl, 4-methoxy-piperidin-1-yl and 8-oxa-3-azabicyclo[3.2.1]octan-3-yl.

5. The compound of claim 1, wherein D is —$NR^4C(O)NR^5R^6$, wherein $R^4$ is hydrogen, $R^5$ and $R^6$ are each independently an optionally substituted group selected from the group consisting of hydrogen, $C_{1-6}$ alkyl, $C_{1-6}$ haloalkyl, $C_{3-7}$ cycloalkyl, $C_{2-7}$ heterocycloalkyl, $C_{6-10}$ aryl, and $C_{1-9}$ heteroaryl, and $R^5$ and $R^6$, when attached to the same nitrogen atom, are optionally combined to form an a 5- to 7-heterocyclic ring or a 5- to 9-membered heteroaryl ring comprising 1 to 3 heteroatoms selected from N, O and S and is substituted with from 0 to 3 $R^D$ substituents.

6. The compound of claim 5 wherein D is —$NR^4C(O)NR^5R^6$, wherein $R^4$ is hydrogen; $R^5$ and $R^6$ are each independently an optionally substituted group selected from the group consisting of hydrogen, $C_{1-6}$ alkyl, $C_{1-6}$ haloalkyl, $C_{3-7}$ cycloalkyl, $C_{3-7}$ heterocycloalkyl, a 5- to 6-membered heteroaryl, and optionally substituted phenyl.

7. The compound of claim 1, wherein $R^1$ is selected from the group consisting of hydrogen, $C_{1-6}$ alkyl, $C_{2-6}$ alkenyl, $C_{2-6}$ alkynyl, $C_{1-6}$ heteroalkyl, phenyl, 5- to 6-membered heteroaryl, 3- to 7-membered heterocycloalkyl, 3- to 7-membered cycloalkyl, wherein $R^1$ is substituted with from 0 to 5 $R^{R1}$ substituents selected from the group consisting of F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^a$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$—$NO_2$, —$N_3$, =O, —CN, $R^{c1}$, —$X^1$—$NR^aR^b$, —$X^1$—$SR^a$, —$X^1$—$OR^a$, —$X^1$—$C(O)OR^a$, —$X^1$—$C(O)NR^aR^b$, —$X^1$—$C(O)R^a$, —$X^1$—$NR^aC(O)R^b$, —$X^1$—$OC(O)R^a$, —$X^1$—$NR^aC(O)NR^aR^b$, —$X^1$—$OC(O)NR^aR^b$, —$X^1$—$NR^aS(O)_2NR^aR^b$, —$X^1$—$S(O)_2R^a$, —$X^1$—$S(O)_2NR^aR^b$, —$X^1$—$NO_2$, —$X^1$—$N_3$, —$X^1$—CN, and $X^1$—$R^{c1}$; wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^a$ and $R^b$, when attached to the same nitrogen atom are combined to form a 3- to 6-membered heterocyclic ring comprising 1 to 2 heteroatoms selected from N, O and S; $R^c$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl; $X^1$ is selected from the group consisting of $C_{1-4}$ alkylene, $C_{2-4}$ alkenylene and $C_{2-4}$ alkynylene, and $R^{c1}$ is selected from the group consisting of phenyl, 2-pyridyl, 3-pyridyl, 4-pyridyl, 2-imidazolyl, 2-indolyl, 1-naphthyl, 2-naphthyl, 2-thienyl, 3-thienyl, 2-pyrrolyl, 2-furanyl and 3-furanyl, and wherein $R^{c1}$ is substituted with from 0 to 3 substituents selected from F, Cl, Br, I, —$NR^aR^b$, —$SR^a$, —$OR^a$, —$S(O)_2R^a$, —$S(O)_2NR^aR^b$, —$NO_2$, —$N_3$, =O, —CN, $C_{1-6}$ alkyl, $C_{2-6}$ alkenyl, $C_{2-6}$ alkynyl and $C_{1-6}$ heteroalkyl; and $R^2$ is selected from the group consisting of hydrogen, $C_{1-6}$ alkyl, $C_{2-6}$ alkenyl, $C_{2-6}$ alkynyl and $C_{1-6}$ heteroalkyl, and wherein $R^2$ is substituted with from 0 to 3 $R^{R2}$ substituents selected from the group consisting of F, Cl, Br, I, —$NR^dR^e$, —$SR^d$, —$OR^d$, —$C(O)OR^d$, —$C(O)NR^dR^e$, —$C(O)R^d$, —$NR^dC(O)R^e$, —$OC(O)R^e$, —$NR^dC(O)NR^dR^e$, —$OC(O)NR^dR^e$, —$NR^dS(O)_2NR^dR^e$, —$S(O)_2R^d$, —$S(O)_2NR^dR^e$, —$R^f$, —$NO_2$, —$N_3$, =O and —CN; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl, optionally $R^d$ and $R^e$, when attached to the same nitrogen atom are combined to form a 3- to 6-membered heterocyclic ring comprising 1 to 2 heteroatoms selected from N, O and S; and $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{2-7}$ heterocycloalkyl, phenyl and —$(CH_2)_{1-4}$-phenyl.

8. The compound of claim 7, wherein $R^1$ is selected from the group consisting of hydrogen, $C_{1-6}$ alkyl, $C_{2-6}$ alkenyl, $C_{2-6}$ alkynyl, $C_{1-6}$ heteroalkyl, wherein $R^1$ is substituted with from 0 to 5 $R^{R1}$ substituents selected from the group consisting of F, Cl, Br, I, —$NR^aR^b$, —$SR^a$, —$OR^a$, —$C(O)OR^a$, —$C(O)NR^aR^b$, —$C(O)R^a$, —$NR^aC(O)R^b$, —$OC(O)R^c$, —$NR^aC(O)NR^aR^b$, —$OC(O)NR^aR^b$, —$NR^aS(O)_2NR^aR^b$, —$S(O)_2R^a$, —$S(O)_2NR^aR^b$, —$R^c$, —$NO_2$, —$N_3$, =O—CN and $X^1$—$R^{c1}$; and $R^2$ is selected from the group consisting of hydrogen, $C_{1-6}$ alkyl, $C_{2-6}$ alkenyl, $C_{2-6}$ alkynyl, $C_{1-6}$ heteroalkyl and is substituted with from 0 to 3 $R^{R2}$ substituents.

9. The compound of claim 8, wherein $R^1$ is selected from the group consisting of hydrogen, methyl, ethyl, propyl, isopropyl, 2-hydroxyprop-2-yl, butyl, sec-butyl, tert-butyl, isobutyl, pentyl, dimethylaminomethyl and hexyl.

10. The compound of claim 1, wherein the compound is selected from the group consisting of: 1-ethyl-3-(4-(7-methyl-6-morpholino-7H-purin-2-yl)phenyl)urea; (S)-1-ethyl-3-(4-(7-methyl-6-(3-methylmorpholino)-7H-purin-2-yl)phenyl)urea; (R)-1-ethyl-3-(4-(7-methyl-6-(3-methylmorpholino)-7H-purin-2-yl)phenyl)urea; (S)-1-ethyl-3-(4-(6-(3-ethylmorpholino)-7-methyl-7H-purin-2-yl)phenyl)urea; 1-ethyl-3-(4-(7-methyl-6-(1,4-oxazepan-4-yl)-7H-purin-2-yl)phenyl)urea; (S)-1-ethyl-3-(4-(7-ethyl-6-(3-methylmorpholino)-7H-purin-2-yl)phenyl)urea; (S)-1-(4-(8-butyl-7-methyl-6-(3-methylmorpholino)-7H-purin-2-yl)phenyl)-3-ethylurea; and (S)-1-ethyl-3-(4-(8-(2-hydroxypropan-2-yl)-7-methyl-6-(3-methylmorpholino)-7H-purin-2-yl)phenyl)urea.

11. A pharmaceutical composition comprising a compound of Formula IA according to claim 1, and a pharmaceutically acceptable diluent, carrier or excipient.

* * * * *